(12) United States Patent
Naef et al.

(10) Patent No.: US 11,897,890 B2
(45) Date of Patent: **\*Feb. 13, 2024**

(54) 2-PHENYL-3,4-DIHYDROPYRROLO[2,1-F] [1,2,4]TRIAZINONE DERIVATIVES AS PHOSPHODIESTERASE INHIBITORS AND USES THEREOF

(71) Applicant: TOPADUR PHARMA AG, Schlieren (CH)

(72) Inventors: Reto Naef, Schlieren (CH); Hermann Tenor, Constance (DE)

(73) Assignee: TOPADUR PHARMA AG, Schlieren (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/547,983

(22) Filed: Dec. 10, 2021

(65) Prior Publication Data

US 2022/0169655 A1  Jun. 2, 2022

Related U.S. Application Data

(63) Continuation of application No. 16/774,333, filed on Jan. 28, 2020, now Pat. No. 11,242,347, which is a
(Continued)

(30) Foreign Application Priority Data

Nov. 16, 2015 (EP) .................................. 15194727

(51) Int. Cl.
| | | |
|---|---|---|
| C07D 487/04 | (2006.01) | |
| C07D 207/50 | (2006.01) | |
| C07D 401/12 | (2006.01) | |

(52) U.S. Cl.
CPC ......... *C07D 487/04* (2013.01); *C07D 207/50* (2013.01); *C07D 401/12* (2013.01)

(58) Field of Classification Search
CPC .................................................. C07D 487/04
See application file for complete search history.

(56) References Cited

U.S. PATENT DOCUMENTS 5,250,534 A  10/1993  Bell et al.
6,362,178 B1  3/2002  Ulrich

FOREIGN PATENT DOCUMENTS

EP  0463756 A1  1/1992
EP  0995751 B1  6/2005
(Continued)

OTHER PUBLICATIONS

Beedimani et al., "Current and Emerging Uses of Phosphodiesterase 5 Inhibitors," International Journal of Pharma and Bio Sciences 5(2): 530-539 (2014).
(Continued)

*Primary Examiner* — David K O'Dell
(74) *Attorney, Agent, or Firm* — MEDLER FERRO WOODHOUSE & MILLS PLLC

(57) ABSTRACT

The present invention relates to compounds of formula I

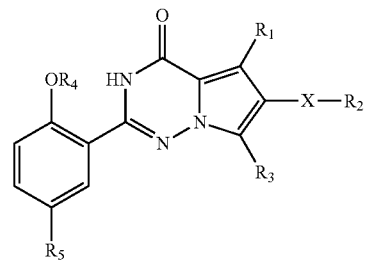

or pharmaceutically acceptable salt, solvate or hydrate thereof, wherein
$R_1$ is $C_1$-$C_3$alkyl optionally substituted with F, $C_3$-$C_6$cycloalkyl, $C_1$-$C_3$alkoxy;
X represents a bond or $C_1$-$C_3$alkylene optionally substituted with OH, ONO, $ONO_2$;
$R_2$ is H, OH, ONO, $ONO_2$, C(O)OH, C(O)O$C_1$-$C_3$alkyl, CHO, CN, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, $S(O_{0-2})C_1$-$C_3$alkyl, $CR_8$=N—$OR_9$, $CR_8$=N—$NR_{10}R_{11}$, $CR_8$=$NR_{12}$ or $CR_8$=N—$ONO_2$;
$R_3$ is $C_1$-$C_6$alkyl optionally substituted with F, OH, ONO, $ONO_2$, $C_1$-$C_3$alkoxy, $C_3$-$C_6$cycloalkyl; $C_3$-$C_6$cycloalkyl, $C_2$-$C_6$alkenyl, $C_2$-$C_6$alkynyl; $R_4$ is $C_1$-$C_6$alkyl optionally substituted with $C_3$-$C_6$cycloalkyl, $C_1$-$C_6$alkoxy, F, ONO, $ONO_2$; $C_2$-$C_6$alkenyl, $C_2$-$C_6$alkynyl, $C_3$-$C_6$cycloalkyl;
$R_5$ is H, $SO_2NR_{13}R_{14}$, $NHSO_2NR_{13}R_{14}$;
$R_6$ is H or $C_1$-$C_3$alkyl;
$R_7$ is H, $C_1$-$C_3$alkyl, $C_1$-$C_3$alkoxy, $C_1$-$C_3$alkyl substituted with phenyl, benzyl or a heterocyclic ring, wherein said phenyl, benzyl or said heterocyclic ring are independently optionally substituted by $C_1$-$C_3$alkyl, F;
$R_8$ is H, $CH_3$ or $C_2H_5$;
$R_9$: H, $C_1$-$C_3$alkyl optionally substituted with OH, ONO, $ONO_2$, CN, COOH, COO$C_1$-$C_3$alkyl, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, $S(O_{0-2})C_1$-$C_3$alkyl;
$R_{10}$ and $R_{11}$ are each independently H, $C_1$-$C_3$alkyl optionally substituted with OH, ONO, $ONO_2$, CN, COOH, COO$C_1$-$C_3$, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, $S(O_{0-2})C_1$-$C_3$alkyl; or together with
(Continued)

the nitrogen atom to which they are attached form a heterocyclic ring, wherein preferably said heterocyclic ring is selected from aziridine, azetidine, pyrollidine, piperidine, morpholine, piperazine and homopiperazine, wherein said heterocyclic ring is optionally substituted with $C_1$-$C_3$ alkyl;

$R_{12}$ is $C_1$-$C_3$ alkyl optionally substituted with OH, ONO, $ONO_2$, CN, COOH, $COOC_1$-$C_3$alkyl, $C_1$-$C_3$alkoxy, OC(O)H, OC(O)—$C_1$-$C_3$alkyl, $C(O)N(R_6)OR_7$, $OC_1$-$C_3$alkylene-C(O)OH, $OC_1$-$C_3$alkylene-C(O)$OC_1$-$C_3$alkyl, $OC_1$-$C_3$alkylene-C(O)$N(R_6)OR_7$, $S(O_{0-2})C_1$-$C_3$alkyl; $R_{13}$ and $R_{14}$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homopiperazine, 2,5-diazabicyclo[2,2,1]heptane and 3,-7-diazabicyclo[3,3,0]octane, wherein said heterocyclic ring is optionally substituted with $R_{15}$;

$R_{15}$ is $C_1$-$C_6$alkyl optionally substituted with halogen, OH, ONO, $ONO_2$, $C_1$-$C_3$alkoxy, $C_1$-$C_3$haloalkoxy, $COOR_{16}$, $NR_{17}R_{18}$, C=$NR_{19}$, or with a tetrazole group which is optionally substituted with $C_1$-$C_3$alkyl; or a heteroaryl ring which is optionally substituted with F, wherein the at least one heteroatom of said heteroaryl ring is nitrogen;

$R_{16}$ is H, or $C_1$-$C_4$alkyl optionally substituted with F, OH, ONO, $ONO_2$, $NR_{17}R_{18}$, or with a heteroaryl ring, wherein the at least one heteroatom of said heteroaryl ring is nitrogen, and wherein preferably said heteroaryl ring is selected from pyrrolidine, piperidine, piperazine, morpholine, pyrrole, and imidazole, wherein nitrogen atom is directly bound to $C_1$-$C_4$ alkyl;

$R_{17}$ and $R_{18}$ are each independently H or $C_1$-$C_4$alkyl optionally substituted with ONO, $ONO_2$;

$R_{19}$ is $C_1$-$C_4$alkyl optionally substituted with F, ONO, $ONO_2$; $C_3$-$C_6$cycloalkyl;

and their use in methods of treating or preventing a disease alleviated by inhibition of PDE-5 in a human or in a non-human mammal.

8 Claims, 5 Drawing Sheets

Related U.S. Application Data continuation of application No. 15/774,130, filed as application No. PCT/EP2016/077720 on Nov. 15, 2016, now Pat. No. 10,570,137.

(56) References Cited

FOREIGN PATENT DOCUMENTS

| EP | 2154139 A1 | 2/2010 |
|---|---|---|
| WO | 99/24433 A1 | 5/1999 |
| WO | 01/60825 A1 | 8/2001 |
| WO | 2002/074774 A1 | 9/2002 |
| WO | 03/099286 A1 | 12/2003 |
| WO | 2006/007378 A2 | 1/2006 |
| WO | 2010/081647 A2 | 6/2010 |
| WO | 2011/075655 A1 | 6/2011 |
| WO | 2013/164061 A1 | 11/2013 |

OTHER PUBLICATIONS

Corbin et al., "Vardenafil: Structural Basis for Higher Potency Over Sildenafil in Inhibiting CGMP-Specific Phosphodiesterase-5 (PDE5)," Neurochemistry International 45: 859-863 (2004).
Dobhal et al., "Current Status and Future Prospects of PDE5 Inhibitors for Various Therapeutic Implications," Critical Review in Pharmaceutical Sciences 1(3): 13-27 (2012).
Monica et al., "Modulating cGMP Levels and Therapeutic Drug Targets in Cardiovascular and Non-Cardiovascular Diseases," OA Biochemistry 2(1): 3 (2014).
Papapetropoulous et al., "Extending the Translational Potential of Targeting NO/CGMP-Regulated Pathways in the CVS," British Journal of Pharmacology 172: 1397-1414 (2015).
Registry, CAS-RN:1357569-76-6, Feb. 27, 2012.
Robinson et al., "Development and Comparison of hERG Blocker Classifiers: Assessment on Different Datasets Yields Markedly Different Results," Molecular Informatics 30(5): 443-458 (2011).
Wermuth et al., "Molecular Variation Based on Isosteric Replacements," in Chapter 13, The Practice of Medicinal Chemistry, Academic pp. 203-237 (1996).
Wronski et al., "The New Horizons of Pharmacology, Unexpected Pharmacological Actions and a New Therapeutic Strategy of Phosphodiesterase-5 Inhibitors," central European Journal of Urology 67: 314-318 (2014).
The International Search Report issued in PCT/EP2016/077720 dated Jan. 3, 2017.

2-PHENYL-3,4-DIHYDROPYRROLO[2,1-F][1,2,4]TRIAZINONE DERIVATIVES AS PHOSPHODIESTERASE INHIBITORS AND USES THEREOF

The present invention relates to pharmaceutically useful compounds, in particular to compounds which are useful in the inhibition of cyclic guanosine 3',5'-monophosphate phosphodiesterases (cGMP PDEs), and hereby in particular in the inhibition of type 5 cyclic guanosine 3',5'-monophosphate phosphodiesterase (cGMP PDE5). The compounds of the present invention have utility in a variety of therapeutic areas, including male erectile dysfunction (MED), Alzheimer's disease, pulmonary artery hypertension (PAH), endothelial dysfunction (ED), benign prostatic hyperplasia (BPH) and lower urinary tract symptoms (LUTS), priapism, cystic fibrosis, peripheral vascular disease, vascular disorders such as Raynaud's disease, systemic sclerosis (SSc), scleroderma, diabetes, and in particular for wound healing, in particular chronic wound healing, diabetic foot, diabetic foot ulcer, leg ulcer and diabetic neuropathy.

RELATED ART

Phosphodiesterases (PDEs) are enzymes that catalyzes the hydrolysis and thus the degradation of cyclic adenosine monophosphate (cAMP) and cyclic guanosine monophosphate (cGMP) and thereby regulates intracellular levels of second messengers. Inhibition of PDEs leads to increasing intracellular concentrations of endogenous cAMP/cGMP. Therefore, inhibition of PDE can mediate a variety of physiological mechanisms at different cell and organ levels.

Phosphodiesterase type 5 (PDE5) hydrolyses cyclic guanylate monophosphate (cGMP) specifically to 5' GMP. The selective inhibition of PDE5 has been validated as a relevant approach and strategies directed to promote inhibition of PDE5 activity have been applied as therapeutic tools, in particular, in neuronal and cardiovascular conditions. Moreover, the introduction of PDE5 inhibitors has revolutionized the treatment of male erectile dysfunction (MED) (Dobhal T, Kaur S, Prakash Sharma O, Hari Kumar S L, Critical Review in Pharmaceutical Sciences (2012) 1(3):13-27). Several PDE5 inhibitors are on the market and are characterized particularly for MED or pulmonary hypertension (PH), in particular PAH (Papapetropoulos A, Hobbs A J, Topouzis S, British Journal of Pharmacology (2015) 172: 1397-1414; Monica F Z, Murad F, Bian K, OA Biochemistry 2014 Mar. 11; 2(1):3; Beedimani R S, Kalmath B, Int J Pharm Bio Sci (2014) 5(2): 530-539; Wronski S, Cent European J Urol (2014) 67: 314-318; and references cited therein). Most prominent examples of PDE5 inhibitors are Sildenafil, Tadalafil and Vardenafil which have been described among others, for example, in WO 99/24433, WO 01/60825, EP 995'751 and WO 2011/075655.

Beside the success of the known PDE5 inhibitors, there is still a need for further and in particular more potent PDE5 inhibitors and their pharmaceutical compositions for use in the therapeutic treatment or prophylaxis of diseases associated with a disturbed cGMP balance. Moreover, and in general, there is still a need for compounds and their pharmaceutical compositions being beneficial for use in the therapeutic treatment or prophylaxis of diseases associated with a disturbed cGMP balance.

SUMMARY OF THE INVENTION

We have surprisingly found that the compounds of the present invention are very potent and selective inhibitors of PDE5. Furthermore, we have surprisingly found that the compounds of the present invention can be tailored to become dual-pharmacology NO-releasing PDE5 inhibitors which are believed to release NO in addition to its PDE 5 inhibition in a more than additive fashion. These dual-pharmacology NO-releasing PDE5 inhibitors are believed to be highly beneficial for the treatment of diabetic patients. Moreover, we have surprisingly found that preferred compounds of the present invention show even a significantly higher PDE5 inhibition activity as compared to known PDE5 inhibitors such as sildenafil. As a consequence, the novel pyrrolo triazine compounds of the present invention are useful in the therapy and prophylaxis of diseases which are associated with a disturbed cGMP balance. Due to the potent and selective PDE5 inhibition exhibited by compounds of the present invention, cGMP levels are elevated, which in turn can give rise to beneficial vasodilatory, anti-vasospastic, anti-platelet, anti-neutrophil, natriuretic and diuretic activities. Furthermore, the tailoring of the inventive compounds to dual-pharmacology NO-releasing PDE5 inhibitors allows the release of nitric oxide for activating the soluble guanylate cyclase as well as the PDE 5 inhibition in a more than additive fashion. Thus, the compounds of the present invention have utility in variety of therapeutic areas where a disturbed cGMP balance occurred and/or PDE5 inhibition is thought to be beneficial. Some of the preferred therapeutic areas are wound healing, in particular chronic wound healing, diabetic foot, diabetic foot ulcer, leg ulcer, Raynaud's, male erectile dysfunction, female sexual dysfunction, Alzheimer's disease, diabetes, hair loss, skin aging, vascular aging, pulmonary artery hypertension and chronic heart failure.

Thus, in a first aspect, the present invention provides for a compound of formula I

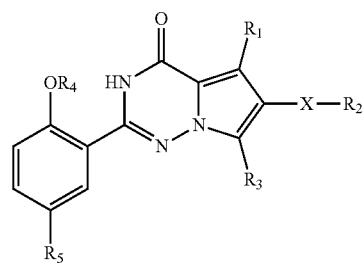

or pharmaceutically acceptable salt, solvate or hydrate thereof, wherein $R_1$ is $C_1$-$C_3$alkyl optionally substituted with F, $C_3$-$C_6$cycloalkyl, $C_1$-$C_3$alkoxy; X represents a bond or $C_1$-$C_3$alkylene optionally substituted with OH, ONO, $ONO_2$;

$R_2$ is H, OH, ONO, $ONO_2$, C(O)OH, C(O)O$C_1$-$C_3$alkyl, CHO, CN, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl, $CR_8$=N—$OR_9$, $CR_8$=N—$NR_{10}R_{11}$, $CR_8$=N$R_{12}$ or $CR_8$=N—$ONO_2$;

$R_3$ is $C_1$-$C_6$alkyl optionally substituted with F, OH, ONO, $ONO_2$, $C_1$-$C_3$alkoxy, $C_3$-$C_6$cycloalkyl; $C_3$-$C_6$cycloalkyl, $C_2$-$C_6$alkenyl, $C_2$-$C_6$alkynyl;

$R_4$ is $C_1$-$C_6$alkyl optionally substituted with $C_3$-$C_6$cycloalkyl, $C_1$-$C_6$alkoxy, F, ONO, $ONO_2$; $C_2$-$C_6$alkenyl, $C_2$-$C_6$alkynyl, $C_3$-$C_6$cycloalkyl;

$R_5$ is H, $SO_2NR_{13}R_{14}$, $NHSO_2NR_{13}R_{14}$;

$R_6$ is H or $C_1$-$C_3$alkyl;

$R_7$ is H, $C_1$-$C_3$alkyl, $C_1$-$C_3$alkoxy, $C_1$-$C_3$alkyl substituted with phenyl, benzyl or a heterocyclic ring, wherein said phenyl, benzyl or said heterocyclic ring are independently optionally substituted by $C_1$-$C_3$alkyl, F;

$R_8$ is H, $CH_3$ or $C_2H_5$;

$R_9$ is H, $C_1$-$C_3$alkyl optionally substituted with OH, ONO, $ONO_2$, CN, COOH, $COOC_1$-$C_3$alkyl, $C_1$-$C_3$alkoxy, OC(O)H, OC(O)—$C_1$-$C_3$alkyl, $C(O)N(R_6)OR_7$, $OC_1$-$C_3$alkylene-C(O)OH, $OC_1$-$C_3$alkylene-C(O)O$C_1$-$C_3$alkyl, $OC_1$-$C_3$alkylene-C(O)N($R_6$)$OR_7$, $S(O_{0-2})C_1$-$C_3$alkyl;

$R_{10}$ and $R_{11}$ are each independently H, $C_1$-$C_3$alkyl optionally substituted with OH, ONO, $ONO_2$, CN, COOH, $COOC_1$-$C_3$, $C_1$-$C_3$alkoxy, OC(O)H, OC(O)—$C_1$-$C_3$alkyl, $C(O)N(R_6)OR_7$, $OC_1$-$C_3$alkylene-C(O)OH, $OC_1$-$C_3$alkylene-C(O)O$C_1$-$C_3$alkyl, $OC_1$-$C_3$alkylene-C(O)N($R_6$)$OR_7$, $S(O_{0-2})C_1$-$C_3$alkyl; or together with the nitrogen atom to which they are attached form a heterocyclic ring, wherein preferably said heterocyclic ring is selected from aziridine, azetidine, pyrollidine, piperidine, morpholine, piperazine and homopiperazine, wherein said heterocyclic ring is optionally substituted with $C_1$-$C_3$ alkyl;

$R_{12}$ is $C_1$-$C_3$ alkyl optionally substituted with OH, ONO, $ONO_2$, CN, COOH, $COOC_1$-$C_3$alkyl, $C_1$-$C_3$alkoxy, OC(O)H, OC(O)—$C_1$-$C_3$alkyl, $C(O)N(R_6)OR_7$, $OC_1$-$C_3$alkylene-C(O)OH, $OC_1$-$C_3$alkylene-C(O)O$C_1$-$C_3$alkyl, $OC_1$-$C_3$alkylene-C(O)N($R_6$)$OR_7$, $S(O_{0-2})C_1$-$C_3$alkyl;

$R_{13}$ and $R_{14}$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homopiperazine, 2,5-diazabicyclo[2,2,1]heptane and 3,7-diazabicyclo[3,3,0]octane, wherein said heterocyclic ring is optionally substituted with $R_{15}$;

$R_{15}$ is $C_1$-$C_6$alkyl optionally substituted with halogen, OH, ONO, $ONO_2$, $C_1$-$C_3$alkoxy, $C_1$-$C_3$haloalkoxy, $COOR_{16}$, $NR_{17}R_{18}$, C=$NR_{19}$, or with a tetrazole group which is optionally substituted with $C_1$-$C_3$alkyl; or a heteroaryl ring which is optionally substituted with F, wherein the at least one heteroatom of said heteroaryl ring is nitrogen;

$R_{16}$ is H, or $C_1$-$C_4$alkyl optionally substituted with F, OH, ONO, $ONO_2$, $NR_{17}R_{18}$, or with a heteroaryl ring, wherein the at least one heteroatom of said heteroaryl ring is nitrogen, and wherein preferably said heteroaryl ring is selected from pyrrolidine, piperidine, piperazine, morpholine, pyrrole, and imidazole, wherein nitrogen atom is directly bound to $C_1$-$C_4$ alkyl;

$R_{17}$ and $R_{18}$ are each independently H or $C_1$-$C_4$alkyl optionally substituted with ONO, $ONO_2$;

$R_{19}$ is $C_1$-$C_4$alkyl optionally substituted with F, ONO, $ONO_2$; $C_3$-$C_6$cycloalkyl.

In a further aspect, the present invention provides for a pharmaceutical composition comprising at least one of the inventive compound of formula I, or a pharmaceutically acceptable salt, solvate or hydrate thereof, and a pharmaceutically acceptable excipient, adjuvant, or carrier.

In another aspect, the present invention provides for a compound of formula I, or a pharmaceutical composition, or a pharmaceutically acceptable salt, solvate or hydrate thereof, for use in a method of treating or preventing a disease alleviated by inhibition of PDE-5 in a human or in a non-human mammal, preferably in a human. Preferably, said disease is selected from wound healing, chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein further preferably said disease is selected from wound healing, chronic wound healing, diabetic foot, diabetic foot ulcer, leg ulcer, diabetic neuropathy, peripheral vascular disease, vascular disorders, Raynaud's disease, systemic sclerosis (SSc), scleroderma, diabetes, pulmonary artery hypertension, male erectile dysfunction, and wherein again further preferably said disease is selected from wound healing, chronic wound healing, diabetic foot, diabetic foot ulcer, leg ulcer and diabetic neuropathy.

In again another aspect, the present invention provides for a compound of formula IV

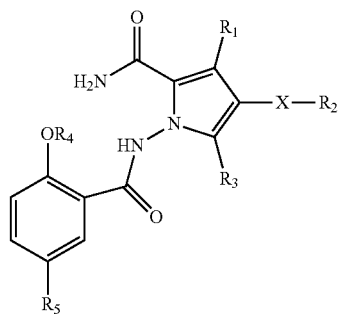

wherein X, $R_1$, $R_2$, $R_3$, $R_4$, $R_5$ are defined as for the compound of formula I.

In again another aspect, the present invention provides for a process for the preparation of a compound of formula I,

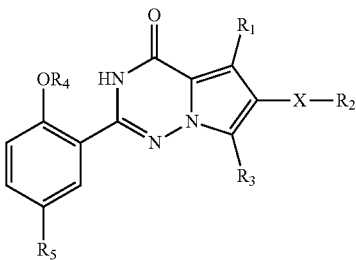

wherein said process comprises:
(a) reaction of a compound of formula II with a benzoic acid derivative of formula III in an aprotic or a protic solvent to generate a compound of formula IV

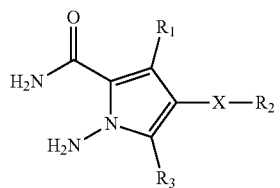

II

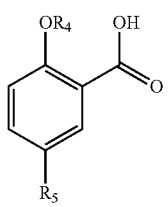

III

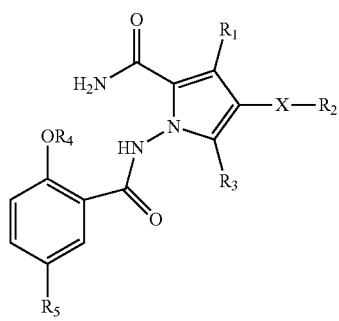

IV (b) cyclization of said compound of formula IV to yield compound of formula I, wherein X, $R_1$, $R_2$, $R_3$, $R_4$, and $R_5$ are defined as for the compound of formula I.

In again another aspect, the present invention provides for a process for the preparation of a compound of formula I, wherein said process comprises (a) reaction of a compound of formula VI with a benzoyl chloride derivative of formula VIA to generate a compound of formula VII

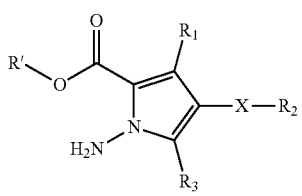

VI

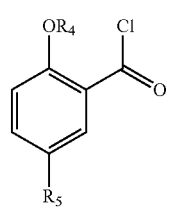

VIA

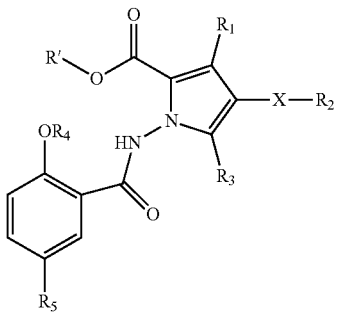

VII (b) hydrolysis of the ester compound of formula VII to an acid derivative of formula VIII

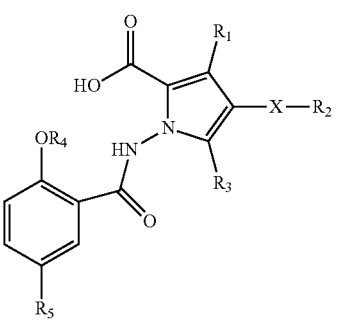

VIII (c) amination of said compound of formula VIII to yield a compound of formula IV

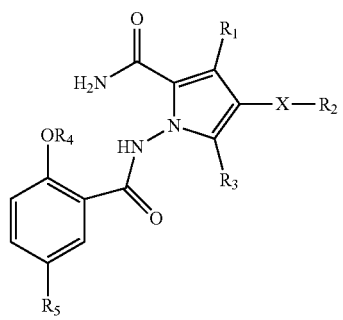

IV (d) cyclization of said compound of formula IV to yield compound of formula I, wherein X, $R_1$, $R_2$, $R_3$, $R_4$, and $R_5$ are defined as for the compound of formula I; and wherein R' is $C_1$-$C_4$ alkyl, benzyl, 4-alkoxybenzyl.

In again another aspect, the present invention provides for a process for the preparation of a compound of formula I, wherein said process comprises conversion of compound of formula IA to yield compound of formula I

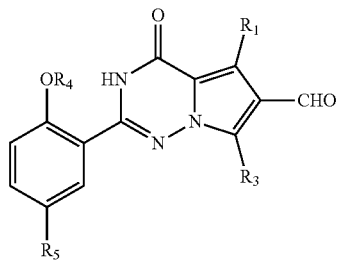

IA wherein X, $R_1$, $R_2$, $R_3$, $R_4$, and $R_5$ are defined as for the compound of formula I in any one of the claims 1 to 8.

Further aspects and embodiments of the present invention will be become apparent as this description continues.

DESCRIPTION OF THE FIGURES

FIG. 1A: Concentration dependent measurement of cGMP in hPASMC incubated for 15 min in presence of inventive compound 1r in concentrations of $1\times10^{-16}$M (0.1 fM)-$1\times10^{-7}$M (100 nM).

FIG. 1B: Concentration dependent measurement of cGMP in hPASMC incubated for 30 min in presence of inventive compound 1v in concentrations of $1\times10^{-12}$M (1 pM)-$1\times10^{-7}$ M (100 nM).

FIG. 1C: Concentration dependent measurement of cGMP in hPASMC incubated for 15 min in presence of reference PDE5 inhibitor sildenafil in concentrations of $1\times10^{-10}$M (0.1 nM)-$1\times10^{-7}$M (100 nM).

DETAILED DESCRIPTION OF THE INVENTION

Figure 1A:
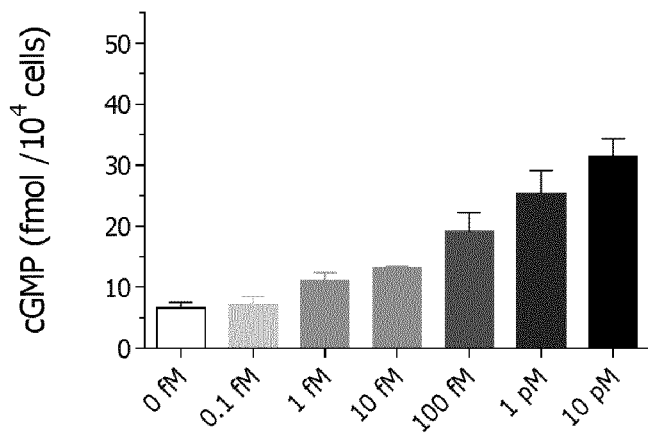
FIGS. 1A-1C: Concentration dependent measurements of cyclic guanosine 3'-5'-monophosphate (cGMP) in human pulmonary artery smooth muscle cells (hPASMC) incubated in presence of the compounds of the inventions or the reference PDE5 inhibitor sildenafil.

Unless defined otherwise, all technical and scientific terms used herein have the same meanings as commonly understood by one of ordinary skill in the art to which this invention belongs.

We have surprisingly found that the compounds of formula I of the present invention are very potent and selective inhibitors of PDE5. Furthermore, we have surprisingly found that the compounds of the present invention can be tailored to become dual-pharmacology NO-releasing PDE5 inhibitors which are believed to release NO in addition to its PDE 5 inhibition in a more than additive fashion. Moreover, preferred compounds of the present invention show even a significantly higher PDE5 inhibition activity as compared to known PDE5 inhibitors such as sildenafil.

Thus, in a first aspect, the present invention provides for a compound of formula I

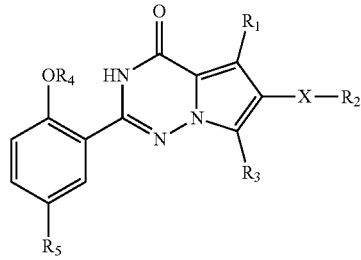

I or pharmaceutically acceptable salt, solvate or hydrate thereof, wherein
$R_1$ is $C_1$-$C_3$alkyl optionally substituted with F, $C_3$-$C_6$cycloalkyl, $C_1$-$C_3$alkoxy;
X represents a bond or $C_1$-$C_3$alkylene optionally substituted with OH, ONO, $ONO_2$;
$R_2$ is H, OH, ONO, $ONO_2$, C(O)OH, C(O)O$C_1$-$C_3$alkyl, CHO, CN, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl, C$R_8$=N—O$R_9$, C$R_8$=N—NR$_{10}$R$_{11}$, C$R_8$=NR$_{12}$ or C$R_8$=N—$ONO_2$;
$R_3$ is $C_1$-$C_6$alkyl optionally substituted with F, OH, ONO, $ONO_2$, $C_1$-$C_3$alkoxy, $C_3$-$C_6$cycloalkyl; $C_3$-$C_6$cycloalkyl, $C_2$-$C_6$alkenyl, $C_2$-$C_6$alkynyl;
$R_4$ is $C_1$-$C_6$alkyl optionally substituted with $C_3$-$C_6$cycloalkyl, $C_1$-$C_6$alkoxy, F, ONO, $ONO_2$; $C_2$-$C_6$alkenyl, $C_2$-$C_6$alkynyl, $C_3$-$C_6$cycloalkyl;
$R_5$ is H, $SO_2$NR$_{13}$R$_{14}$, NHSO$_2$NR$_{13}$R$_{14}$;
$R_6$ is H or $C_1$-$C_3$alkyl;
$R_7$ is H, $C_1$-$C_3$alkyl, $C_1$-$C_3$alkoxy, $C_1$-$C_3$alkyl substituted with phenyl, benzyl or a heterocyclic ring, wherein said phenyl, benzyl or said heterocyclic ring are independently optionally substituted by $C_1$-$C_3$alkyl, F;
$R_8$ is H, $CH_3$ or $C_2H_5$;
$R_9$ is H, $C_1$-$C_3$alkyl optionally substituted with OH, ONO, $ONO_2$, CN, COOH, COO$C_1$-$C_3$alkyl, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl;
$R_{10}$ and $R_{11}$ are each independently H, $C_1$-$C_3$alkyl optionally substituted with OH, ONO, $ONO_2$, CN, COOH, COO$C_1$-$C_3$, $C_1$-$C_3$alkoxy, OC(O)H, OC(O)—$C_1$-$C_3$alkyl, C(O)N($R_6$)O$R_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)O$R_7$, S($O_{0-2}$)$C_1$-$C_3$alkyl; or together with the nitrogen atom to which they are attached form a heterocyclic ring, wherein preferably said heterocyclic ring is selected from aziridine, azetidine, pyrollidine, piperidine, morpholine, piperazine and homopiperazine, wherein said heterocyclic ring is optionally substituted with $C_1$-$C_3$ alkyl;
$R_{12}$ is $C_1$-$C_3$ alkyl optionally substituted with OH, ONO, $ONO_2$, CN, COOH, COO$C_1$-$C_3$alkyl, $C_1$-$C_3$alkoxy, OC(O)H, OC(O)—$C_1$-$C_3$alkyl, C(O)N($R_6$)O$R_7$, O$C_1$-

$C_3$alkylene-C(O)OH, $OC_1$-$C_3$alkylene-C(O)$OC_1$-$C_3$alkyl, $OC_1$-$C_3$alkylene-C(O)N($R_6$)$OR_7$, $S(O_{0-2})C_1$-$C_3$alkyl;

$R_{13}$ and $R_{14}$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homopiperazine, 2,5-diazabicyclo[2,2,1]heptane and 3,7-diazabicyclo[3,3,0]octane, wherein said heterocyclic ring is optionally substituted with $R_{15}$;

$R_{15}$ is $C_1$-$C_6$alkyl optionally substituted with halogen, OH, ONO, $ONO_2$, $C_1$-$C_3$alkoxy, $C_1$-$C_3$haloalkoxy, $COOR_{16}$, $NR_{17}R_{18}$, C=$NR_{19}$, or with a tetrazole group which is optionally substituted with $C_1$-$C_3$alkyl; or a heteroaryl ring which is optionally substituted with F, wherein the at least one heteroatom of said heteroaryl ring is nitrogen;

$R_{16}$ is H, or $C_1$-$C_4$alkyl optionally substituted with F, OH, ONO, $ONO_2$, $NR_{17}R_{18}$, or with a heteroaryl ring, wherein the at least one heteroatom of said heteroaryl ring is nitrogen, and wherein preferably said heteroaryl ring is selected from pyrrolidine, piperidine, piperazine, morpholine, pyrrole, and imidazole, wherein nitrogen atom is directly bound to $C_1$-$C_4$ alkyl;

$R_{17}$ and $R_{18}$ are each independently H or $C_1$-$C_4$alkyl optionally substituted with ONO, $ONO_2$;

$R_{19}$ is $C_1$-$C_4$alkyl optionally substituted with F, ONO, $ONO_2$; $C_3$-$C_6$cycloalkyl.

Thus, in a further aspect, the present invention provides for a compound of formula I

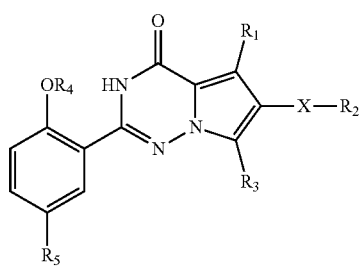

I or pharmaceutically acceptable salt, solvate or hydrate thereof, wherein $R_1$ is $C_1$-$C_3$alkyl optionally substituted with F, $C_3$-$C_6$cycloalkyl, $C_1$-$C_3$alkoxy;

X represents a bond or $C_1$-$C_3$alkylene optionally substituted with OH, ONO, $ONO_2$;

$R_2$ is OH, ONO, $ONO_2$, C(O)OH, C(O)$OC_1$-$C_3$alkyl, CHO, CN, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$, $S(O_{0-2})C_1$-$C_3$alkyl, $CR_8$=N—$OR_9$, $CR_8$=N—$NR_{10}R_{11}$, $CR_8$=$NR_{12}$ or $CR_8$=N—$ONO_2$;

$R_3$ is $C_1$-$C_6$alkyl optionally substituted with F, OH, ONO, $ONO_2$, $C_1$-$C_3$alkoxy, $C_3$-$C_6$cycloalkyl; $C_3$-$C_6$cycloalkyl, $C_2$-$C_6$alkenyl, $C_2$-$C_6$alkynyl;

$R_4$ is $C_1$-$C_6$alkyl optionally substituted with $C_3$-$C_6$cycloalkyl, $C_1$-$C_6$alkoxy, F, ONO, $ONO_2$; $C_2$-$C_6$alkenyl, $C_2$-$C_6$alkynyl, $C_3$-$C_6$cycloalkyl;

$R_5$ is H, $SO_2NR_{13}R_{14}$, $NHSO_2NR_{13}R_{14}$;

$R_6$ is H or $C_1$-$C_3$alkyl;

$R_7$ is H, $C_1$-$C_3$alkyl, $C_1$-$C_3$alkoxy, $C_1$-$C_3$alkyl substituted with phenyl, benzyl or a heterocyclic ring, wherein said phenyl, benzyl or said heterocyclic ring are independently optionally substituted by $C_1$-$C_3$alkyl, F;

$R_8$ is H, $CH_3$ or $C_2H_5$;

$R_9$ is H, $C_1$-$C_3$alkyl optionally substituted with OH, ONO, $ONO_2$, CN, COOH, $COOC_1$-$C_3$alkyl, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$, $S(O_{0-2})C_1$-$C_3$alkyl;

$R_{10}$ and $R_{11}$ are each independently H, $C_1$-$C_3$alkyl optionally substituted with OH, ONO, $ONO_2$, CN, COOH, $COOC_1$-$C_3$, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$, $S(O_{0-2})C_1$-$C_3$alkyl; or together with the nitrogen atom to which they are attached form a heterocyclic ring, wherein preferably said heterocyclic ring is selected from aziridine, azetidine, pyrollidine, piperidine, morpholine, piperazine and homopiperazine, wherein said heterocyclic ring is optionally substituted with $C_1$-$C_3$ alkyl;

$R_{12}$ is $C_1$-$C_3$ alkyl optionally substituted with OH, ONO, $ONO_2$, CN, COOH, $COOC_1$-$C_3$alkyl, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$, $S(O_{0-2})C_1$-$C_3$alkyl;

$R_{13}$ and $R_{14}$ are each independently H or $C_1$-$C_6$alkyl optionally substituted with F, OH, ONO, $ONO_2$, COOH, $C_1$-$C_3$alkoxy, $C_3$-$C_6$cycloalkyl; or together with the nitrogen atom to which they are attached form a heterocyclic ring, wherein preferably said heterocyclic ring is selected from aziridine, azetidine, pyrollidine, piperidine, morpholine, piperazine, homopiperazine, 2,5-diazabicyclo[2,2,1]heptane and 3,7-diazabicyclo[3,3,0]octane, wherein said heterocyclic ring is optionally substituted with $R_{15}$;

$R_{15}$ is $C_1$-$C_6$alkyl optionally substituted with halogen, OH, ONO, $ONO_2$, $C_1$-$C_3$alkoxy, $C_1$-$C_3$haloalkoxy, $COOR_{16}$, $NR_{17}R_{18}$, C=$NR_{19}$, or with a tetrazole group which is optionally substituted with $C_1$-$C_3$alkyl; or a heteroaryl ring which is optionally substituted with F, wherein the at least one heteroatom of said heteroaryl ring is nitrogen;

$R_{16}$ is H, or $C_1$-$C_4$alkyl optionally substituted with F, OH, ONO, $ONO_2$, $NR_{17}R_{18}$, or with a heteroaryl ring, wherein the at least one heteroatom of said heteroaryl ring is nitrogen, and wherein preferably said heteroaryl ring is selected from pyrrolidine, piperidine, piperazine, morpholine, pyrrole, and imidazole, wherein nitrogen atom is directly bound to $C_1$-$C_4$ alkyl;

$R_{17}$ and $R_{18}$ are each independently H or $C_1$-$C_4$alkyl optionally substituted with ONO, $ONO_2$;

$R_{19}$ is $C_1$-$C_4$alkyl optionally substituted with F, ONO, $ONO_2$; $C_3$-$C_6$cycloalkyl.

Each alkyl moiety either alone or as part of a larger group such as alkoxy or alkylene is a straight or branched chain and is preferably $C_1$-$C_6$alkyl, more preferably $C_1$-$C_3$alkyl. Examples include methyl, ethyl, n-propyl, prop-2-yl, n-butyl, but-2-yl, 2-methyl-prop-1-yl or 2-methyl-prop-2-yl.

Examples of an alkoxy include methoxy, ethoxy, propoxy, iso-propoxy, n-butoxy, sec-butoxy, tert-butoxy, n-pentoxy, neo-pentoxy, n-hexoxy. As described herein, alkoxy may include further substituents such as halogen atoms leading to haloalkoxy moieties.

Each alkylene moiety is a straight or branched chain and is, for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—.

Each cycloalkyl moiety can be in mono- or bi-cyclic form, typically and preferably in mono-cyclic form, and preferably contains 3 to 8 carbon atoms, more preferably 3 to 7 carbon atoms. Examples of monocyclic cycloalkyl groups include cyclopropyl, cyclobutyl and cyclohexyl.

Each alkenyl moiety either alone or as part of a larger group such as alkenyloxy or alkenylene is a straight or branched chain and is preferably $C_2$-$C_6$alkenyl, more preferably $C_2$-$C_4$alkenyl. Each moiety can be of either the (E)- or (Z)-configuration. Examples include vinyl and allyl. A compound of the present invention comprising an alkenyl moiety thus may include, if applicable, either said compound with said alkenyl moiety in its (E)-configuration, said compound with said alkenyl moiety in its (Z)-configuration and mixtures thereof in any ratio.

Each alkynyl moiety either alone or as part of a larger group such as alkynyloxy is a straight or branched chain and is preferably $C_2$-$C_6$alkynyl, more preferably $C_2$-$C_4$alkynyl. Examples are ethynyl and propargyl.

Halogen is fluorine, chlorine, bromine, or iodine.

Each haloalkyl moiety either alone or as part of a larger group such as haloalkoxy is an alkyl group substituted by one or more of the same or different halogen atoms. Examples include difluoromethyl, trifluoromethyl, chlorodifluoromethyl and 2,2,2-trifluoro-ethyl.

The term "heterocyclic ring" refers to a saturated or partially unsaturated carbocyclic ring containing one to four heteroatoms selected from nitrogen, oxygen and sulfur as ring members. Such rings do not contain adjacent oxygen atoms, adjacent sulfur atoms, or adjacent oxygen and sulfur atoms within the ring. Preferred examples are aziridine, azetidine, pyrollidine, piperidine, morpholine, piperazine, homopiperazine, tetrahydrofurane, dioxane, 2,5-diazabicyclo[2,2,1]heptane and 3,7-diazabicyclo[3,3,0]octane, and further preferred are aziridine, azetidine, pyrollidine, piperidine, morpholine, piperazine, homopiperazine, 2,5-diazabicyclo[2,2,1]heptane and 3,7-diazabicyclo[3,3,0]octane.

The term "heteroaryl" refers to an aromatic ring system containing at least one heteroatom, and preferably up to three heteroatoms selected from nitrogen, oxygen and sulfur as ring members. Heteroaryl rings do not contain adjacent oxygen atoms, adjacent sulfur atoms, or adjacent oxygen and sulfur atoms within the ring. Preferred examples are include pyrrolidine, piperidine, piperazine, morpholine, pyridine, pyrimidine, pyrazine, pyridazine, pyrrole, pyrazole, imidazole, triazole, isoxazole, oxazole, isothiazole, thiazole, tetrazole, furane, and thiophenyl, and further preferred are pyrrolidine, piperidine, piperazine, morpholine, pyrrole, and imidazole.

Where a group is said to be optionally substituted, preferably there are optionally 1-5 substituents, more preferably optionally 1-3 substituents, again more preferably optionally 1 or 2 substituents. Where a group is said to be optionally substituted, and where there are more than one substituents for said optional substitution of said group, said more than one substituents can either be the same or different.

Certain compounds of formula I of the present invention may contain one or two or more centers of chirality and such compounds may be provided as pure enantiomers or pure diastereoisomers as well as mixtures thereof in any ratio. The compounds of the invention also include all tautomeric forms of the compounds of formula I. The compounds of formula I may also be solvated, especially hydrated, which are also included in the compounds of formula I. Solvation and hydration may take place during the preparation process.

As a consequence, the compounds of the present invention and, thus, the compounds of formula I include stereoisomers, geometric isomers and tautomers. Furthermore, the compounds of the present invention and, thus, the compounds of formula I include solvates or hydrates, pharmaceutically acceptable salts, and solvates or hydrates of the salts thereof.

Compounds of formula I of the present invention include pharmaceutically acceptable salts of said compounds. In particular, the term "pharmaceutically acceptable salt" as used herein, refers to pharmaceutically acceptable organic or inorganic salts of a compound of the present invention, in particular acid addition salts. Exemplary salts include, but are not limited to, salts of physiologically acceptable mineral acids, such as hydrochloric acid, sulfuric acid, nitric acid and phosphoric acid, or salts of organic acids, such as methane-sulfonic acid, p-toluenesulfonic acid, lactic acid, malic acid, tartaric acid, acetic acid, trifluoroacetic acid, citric acid, succinic acid, fumaric acid, maleic acid and salicylic acid. Further examples of pharmacologically acceptable salts of the compounds of formula I are alkali metal and alkaline earth metal salts such as, for example, sodium, potassium, lithium, calcium or magnesium salts, ammonium salts or salts of organic bases such as, for example, methylamine, dimethylamine, triethylamine, piperidine, ethylenediamine, lysine, choline hydroxide, meglumine, morpholine or arginine salts. Further examples of pharmaceutically acceptable salts of the compounds of formula I include the hydrochloride, hydrobromide, sulfate, bisulfate, phosphate, hydrogen phosphate, nitrate, acetate, benzoate, succinate, fumarate, maleate, lactate, citrate, benzenesulphonate, p-toluenesulphonate or the like.

A "solvate" refers to an association or complex of one or more solvent molecules and a compound of the present invention. Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

In a preferred embodiment of the present invention, $R_1$ is $C_1$-$C_3$alkyl. In a further preferred embodiment, $R_1$ is $CH_3$ or $C_2H_5$, and again further preferably $R_1$ is $CH_3$.

In another preferred embodiment, $R_3$ is $C_1$-$C_6$alkyl optionally substituted with F, OH, ONO, $ONO_2$, $C_1$-$C_3$alkoxy, $C_3$-$C_6$cycloalkyl, $C_2$-$C_4$alkenyl. In a further preferred embodiment, $R_3$ is $C_1$-$C_4$alkyl optionally substituted with F, OH, ONO, $ONO_2$, $C_1$-$C_3$alkoxy, $C_3$-$C_6$cycloalkyl, $C_2$-$C_4$alkenyl. In a further preferred embodiment, $R_3$ is $C_1$-$C_4$alkyl optionally substituted with ONO, $ONO_2$ or $C_3$-$C_5$cycloalkyl. In a further preferred embodiment, $R_3$ is $C_1$-$C_4$alkyl optionally substituted with $ONO_2$ or $C_3$-$C_5$cycloalkyl. In a further preferred embodiment, $R_3$ is $C_1$-$C_6$alkyl, preferably $R_3$ is $C_1$-$C_4$alkyl. In a very preferred embodiment, $R_3$ is n-propyl.

In another preferred embodiment, $R_4$ is $C_1$-$C_4$alkyl optionally substituted with $C_3$-$C_6$cycloalkyl, $C_1$-$C_6$alkoxy, F, ONO, $ONO_2$; $C_2$-$C_4$alkenyl. In a further preferred embodiment, $R_4$ is $C_1$-$C_4$alkyl optionally substituted with ONO, $ONO_2$, $C_1$-$C_6$alkoxy, or $C_3$-$C_5$cycloalkyl. In a further preferred embodiment, $R_4$ is $C_1$-$C_4$alkyl optionally substituted with ONO, $ONO_2$ or $C_1$-$C_6$alkoxy. In a further preferred embodiment, $R_4$ is $C_1$-$C_4$alkyl optionally substituted with $ONO_2$ or $C_1$-$C_6$alkoxy. In a further preferred embodiment, $R_4$ represents $C_1$-$C_6$alkyl, preferably $C_1$-$C_4$alky, again preferably $R_4$ represents ethyl or n-propyl.

In a further preferred embodiment, said $R_1$ is $C_1$-$C_3$alkyl; $R_3$ is $C_1$-$C_4$alkyl optionally substituted with F, OH, ONO, $ONO_2$, $C_1$-$C_3$alkoxy, $C_3$-$C_6$cycloalkyl, $C_2$-$C_4$alkenyl; and $R_4$ is $C_1$-$C_4$alkyl optionally substituted with $C_3$-$C_6$cycloalkyl, $C_1$-$C_3$alkoxy, F, ONO, $ONO_2$; $C_2$-$C_4$alkenyl.

In a further preferred embodiment, said $R_1$ is $CH_3$ or $C_2H_5$, preferably $R_1$ is $CH_3$; $R_3$ is $C_1$-$C_4$alkyl optionally substituted with $ONO_2$ or $C_3$-$C_5$cycloalkyl, preferably $R_3$ is n-propyl; and $R_4$ is $C_1$-$C_4$alkyl optionally substituted with $ONO_2$ or $C_3$-$C_5$cycloalkyl, preferably $R_4$ is ethyl or n-propyl.

In a further preferred embodiment, said $R_{13}$ and $R_{14}$ together with the nitrogen atom to which they are attached form a heterocyclic ring, wherein said heterocyclic ring is selected from aziridine, azetidine, pyrollidine, piperidine, morpholine, piperazine, homopiperazine, 2,5-diazabicyclo-[2,2,1]heptane and 3,7-diazabicyclo[3,3,0]octane, wherein said heterocyclic ring is optionally substituted with $R_{15}$; $R_{15}$ is $C_1$-$C_4$alkyl optionally substituted with halogen, OH, ONO, $ONO_2$, $C_1$-$C_3$alkoxy, $C_1$-$C_3$haloalkoxy, $COOR_{16}$, $NR_{17}R_{18}$, C=$NR_{19}$; $R_{16}$ is H, or $C_1$-$C_4$alkyl optionally substituted with F, OH, ONO, $ONO_2$; $R_{17}$ and $R_{18}$ are each independently H or $C_1$-$C_4$alkyl optionally substituted with ONO, $ONO_2$, preferably $R_{17}$ and $R_{18}$ are each independently H or $C_1$-$C_4$alkyl optionally substituted with $ONO_2$; $R_{19}$ is $C_1$-$C_4$alkyl optionally substituted with F, ONO, $ONO_2$, preferably $R_{19}$ is $C_1$-$C_4$alkyl optionally substituted with $ONO_2$.

In a further preferred embodiment, said $R_5$ is $SO_2NR_{13}R_{14}$, $NHSO_2NR_{13}R_{14}$; said $R_{13}$ and $R_{14}$ together with the nitrogen atom to which they are attached form a heterocyclic ring, wherein said heterocyclic ring is selected from aziridine, azetidine, pyrollidine, piperidine, morpholine, piperazine, homopiperazine, 2,5-diazabicyclo-[2,2,1]heptane and 3,7-diazabicyclo[3,3,0]octane, wherein said heterocyclic ring is optionally substituted with $R_{15}$; $R_{15}$ is $C_1$-$C_4$alkyl optionally substituted with halogen, OH, ONO, $ONO_2$, $C_1$-$C_3$alkoxy, $COOR_{16}$, $NR_{17}R_{18}$, C=$NR_{19}$; $R_{16}$ is H, or $C_1$-$C_4$alkyl optionally substituted with F, OH, ONO, $ONO_2$; said $R_{17}$ and $R_{15}$ are each independently H or $C_1$-$C_4$alkyl optionally substituted with ONO, $ONO_2$; said $R_{19}$ is $C_1$-$C_4$alkyl optionally substituted with F, ONO, $ONO_2$.

In a further preferred embodiment, said $R_5$ is $SO_2NR_{13}R_{14}$, wherein $R_{13}$ and $R_{14}$ are each independently H or together with the nitrogen atom to which they are attached form a mono-cyclic ring selected from imidazol, aziridine, azetidine, pyrrolidine, piperidine, morpholine, piperazine and homopiperazine optionally substituted with $R_{15}$; said $R_{15}$ is $C_1$-$C_4$alkyl optionally substituted with halogen, OH, ONO, $ONO_2$, $C_1$-$C_3$alkoxy, $COOR_{16}$, $NR_{17}R_{18}$, C=$NR_{19}$; $R_{16}$ is H, or $C_1$-$C_4$alkyl optionally substituted with F, OH, ONO, $ONO_2$; said $R_{17}$ and $R_{18}$ are each independently H or $C_1$-$C_4$alkyl optionally substituted with ONO, $ONO_2$; said $R_{19}$ is $C_1$-$C_4$alkyl optionally substituted with F, ONO, $ONO_2$.

In a further preferred embodiment, said $R_5$ is $SO_2NR_{13}R_{14}$, wherein $R_{13}$ and $R_{14}$ together with the nitrogen atom to which they are attached form a mono-cyclic ring selected from imidazol, aziridine, azetidine, pyrrolidine, piperidine, morpholine, piperazine and homopiperazine optionally substituted with $R_{15}$; said $R_{15}$ is $C_1$-$C_4$alkyl optionally substituted with halogen, OH, ONO, $ONO_2$, $C_1$-$C_3$alkoxy, $COOR_{16}$, $NR_{17}R_{18}$, C=$NR_{19}$; $R_{16}$ is H, or $C_1$-$C_4$alkyl optionally substituted with OH, ONO, $ONO_2$; said $R_{17}$ and $R_{18}$ are each independently H or $C_1$-$C_4$alkyl optionally substituted with ONO, $ONO_2$; said $R_{19}$ is $C_1$-$C_4$alkyl optionally substituted with ONO, $ONO_2$.

In a further preferred embodiment, said $R_5$ is $SO_2NR_{13}R_{14}$, wherein $R_{13}$ and $R_{14}$ together with the nitrogen atom to which they are attached form a mono-cyclic ring selected from imidazol, aziridine, azetidine, pyrrolidine, piperidine, morpholine, piperazine and homopiperazine optionally substituted with $R_{15}$; said $R_{15}$ is $C_1$-$C_4$alkyl optionally substituted with halogen, OH, $ONO_2$, $C_1$-$C_3$alkoxy, $COOR_{16}$, $NR_{17}R_{18}$, C=$NR_{19}$; $R_{16}$ is H, or $C_1$-$C_4$alkyl optionally substituted with OH, $ONO_2$; said $R_{17}$ and $R_{18}$ are each independently H or $C_1$-$C_4$alkyl optionally substituted with $ONO_2$; said $R_{19}$ is $C_1$-$C_4$alkyl optionally substituted with $ONO_2$.

In a further preferred embodiment, said $R_5$ is $SO_2NR_{13}R_{14}$, wherein $R_{13}$ and $R_{14}$ together with the nitrogen atom to which they are attached form a mono-cyclic ring selected from imidazol, pyrrolidine, piperidine, morpholine, piperazine and homopiperazine optionally substituted with $R_{15}$; said $R_{15}$ is $C_1$-$C_4$alkyl optionally substituted with OH, $ONO_2$, $C_1$-$C_3$alkoxy, $COOR_{16}$, $NR_{17}R_{18}$, C=$NR_{19}$; $R_{16}$ is H, or $C_1$-$C_4$alkyl optionally substituted with OH, $ONO_2$; said $R_{17}$ and $R_{18}$ are each independently H or $C_1$-$C_4$alkyl optionally substituted with $ONO_2$; said $R_{19}$ is $C_1$-$C_4$alkyl optionally substituted with $ONO_2$.

In a further very preferred embodiment, said $R_5$ is $SO_2NR_{13}R_{14}$, wherein $R_{13}$ and $R_{14}$ together with the nitrogen atom to which they are attached form a mono-cyclic ring selected from piperidine, and piperazine optionally substituted with $R_{15}$; said $R_{15}$ is $C_1$-$C_3$alkyl optionally substituted with OH or $ONO_2$.

In a further preferred embodiment, said X represents a bond or $C_1$-$C_3$alkylene optionally substituted with OH. In a further very preferred embodiment, said X represents a bond or $C_1$-$C_2$alkylene optionally substituted with OH. In another very preferred embodiment, said X represents a bond. In another very preferred embodiment, said X represents $C_1$-$C_2$alkylene optionally substituted with OH.

In a further preferred embodiment, said $R_2$ is H, OH, C(O)OH, C(O)O$C_1$-$C_3$alkyl, CHO, CN, OC(O)H, OC(O)—$C_1$-$C_3$alkyl, C(O)N($R_6$)$OR_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)$OR_7$, S($O_{0-2}$)$C_1$-$C_3$alkyl, CH=N—$OR_9$, wherein $R_9$ is H, $C_1$-$C_3$alkyl optionally substituted with OH, ONO, $ONO_2$, CN, COOH, COO$C_1$-$C_3$alkyl, $C_1$-$C_3$alkoxy, OC(O)H, OC(O)—$C_1$-$C_3$alkyl, C(O)N($R_6$)$OR_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)$OR_7$, S($O_{0-2}$)$C_1$-$C_3$alkyl.

In a further preferred embodiment, said $R_2$ is H, OH, C(O)OH, C(O)O$C_1$-$C_3$alkyl, CHO, CN, OC(O)H, OC(O)—$C_1$-$C_3$alkyl, C(O)N($R_6$)$OR_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)$OR_7$, S($O_{0-2}$)$C_1$-$C_3$alkyl, CH=N—$OR_9$, wherein $R_7$ is H, $C_1$-$C_3$alkyl; and wherein $R_9$ is H, $C_1$-$C_3$alkyl optionally substituted with OH, ONO, $ONO_2$, CN, COOH, COO$C_1$-$C_3$alkyl, $C_1$-$C_3$alkoxy, OC(O)H, OC(O)—$C_1$-$C_3$alkyl, C(O)N($R_6$)$OR_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)$OR_7$, S($O_{0-2}$)$C_1$-$C_3$alkyl.

In a further preferred embodiment, said $R_2$ is C(O)OH, C(O)O$C_1$-$C_3$alkyl, CHO, CN, OC(O)H, OC(O)—$C_1$-$C_3$alkyl, C(O)N($R_6$)$OR_7$, O$C_1$-$C_3$alkylene-C(O)OH, O$C_1$-$C_3$alkylene-C(O)O$C_1$-$C_3$alkyl, O$C_1$-$C_3$alkylene-C(O)N($R_6$)$OR_7$, S($O_{0-2}$)$C_1$-$C_3$alkyl, CH=N—$OR_9$, wherein $R_7$ is H, $C_1$-$C_3$alkyl; and wherein $R_9$ is H, $C_1$-$C_3$alkyl optionally substituted with OH, ONO, $ONO_2$, CN, COOH, $COOC_1$-$C_3$alkyl, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$, $S(O_{0-2})C_1$-$C_3$alkyl.

In a further preferred embodiment, said $R_2$ is C(O)OH, $C(O)OC_1$-$C_3$alkyl, CHO, CN, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$, $S(O_{0-2})C_1$-$C_3$alkyl, CH=N—$OR_9$, wherein $R_7$ is H, $C_1$-$C_3$alkyl; and wherein $R_9$ is H, $C_1$-$C_3$alkyl substituted with OH, ONO, $ONO_2$, CN, COOH, $COOC_1$-$C_3$alkyl, $C_1$-$C_3$alkoxy, OC(O)H, OC(O)—$C_1$-$C_3$alkyl, C(O)N($R_6$)$OR_7$, $OC_1$-$C_3$alkylene-C(O)OH, —$OC_1$-$C_3$alkylene-C(O)$OC_1$-$C_3$alkyl, $OC_1$-$C_3$alkylene-C(O)N($R_6$)$OR_7$, —$S(O_{0-2})C_1$-$C_3$alkyl.

In a further very preferred embodiment, said $R_2$ is CHO, CN, CH=N—$OR_9$, preferably (E)-CH=N—$OR_9$, wherein $R_9$ is H, $C_1$-$C_3$alkyl optionally substituted with OH, ONO, $ONO_2$, CN, COOH, $COOC_1$-$C_3$alkyl, OC(O)H, OC(O)—$C_1$-$C_3$alkyl.

In a further very preferred embodiment, said $R_2$ is CHO, CN, CH=N—$OR_9$, preferably (E)-CH=N—$OR_9$, wherein $R_9$ is H, $C_1$-$C_3$alkyl substituted with OH, ONO, $ONO_2$, CN, COOH, $COOC_1$-$C_3$alkyl, OC(O)H, OC(O)—$C_1$-$C_3$alkyl.

In a further very preferred embodiment, said $R_2$ is CH=N—$OR_9$, preferably (E)-CH=N—$OR_9$, wherein $R_9$ is H, $C_1$-$C_3$alkyl optionally substituted with OH, ONO, $ONO_2$, CN, COOH. $COOC_1$-$C_3$alkyl, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$, $S(O_{0-2})C_1$-$C_3$alkyl.

In a further very preferred embodiment, said $R_2$ is CH=N—$OR_9$, preferably (E)-CH=N—$OR_9$, wherein $R_9$ is H, $C_1$-$C_3$alkyl optionally substituted with OH, ONO, $ONO_2$, CN, COOH, $COOC_1$-$C_3$alkyl, OC(O)H, OC(O)—$C_1$-$C_3$alkyl.

In a further very preferred embodiment, said X—$R_2$ represents $C_1$-$C_3$alkylene optionally substituted with OH, ONO, $ONO_2$, CN, C(O)OH, $C_1$-$C_2$alkoxy, $C(O)OC_1$-$C_3$alkyl, C(O)N($R_6$)$OR_7$, CHO, OC(O)H, $OC_1$-$C_3$alkylene-C(O)OH, $OC_1$-$C_3$alkylene-C(O)N($R_6$)$OR_7$, OC(O)—$C_1$-$C_3$alkyl, C(O)N($R_6$)$OR_7$, $CR_8$=N—$OR_9$; $C(O)OC_1$-$C_3$alkyl, CHO, C(O)N($R_6$)$OR_7$, $S(O_{0-2})C_1$-$C_3$alkyl, $CR_8$=N—$OR_9$, $CR_8$=N—$NR_{10}R_{11}$, $CR_8$=$NR_{12}$ or $CR_8$=N—$ONO_2$, wherein further preferably, said $R_6$ is H or $CH_3$, and said $R_8$ is H or $CH_3$.

In a further very preferred embodiment, said X—$R_2$ represents $C_1$-$C_3$alkylene substituted with OH, ONO, $ONO_2$, CN, C(O)OH, $C_1$-$C_2$alkoxy, $C(O)OC_1$-$C_3$alkyl, C(O)N($R_6$)$OR_7$, CHO, OC(O)H, $OC_1$-$C_3$alkylene-C(O)OH, $OC_1$-$C_3$alkylene-C(O)N($R_6$)$OR_7$, OC(O)—$C_1$-$C_3$alkyl, C(O)N($R_6$)$OR_7$, $CR_8$=N—$OR_9$; $C(O)OC_1$-$C_3$alkyl, CHO, C(O)N($R_6$)$OR_7$, $S(O_{0-2})C_1$-$C_3$alkyl, $CR_8$=N—$OR_9$, $CR_8$=N—$NR_{10}R_{11}$, $CR_8$=$NR_{12}$ or $CR_8$=N—$ONO_2$, wherein further preferably, said $R_6$ is H or $CH_3$, and said $R_8$ is H or $CH_3$.

In a further preferred embodiment, $R_7$ is H, $C_1$-$C_3$alkyl, $C_1$-$C_3$alkoxy, $C_1$-$C_3$alkyl substituted with phenyl, benzyl or a heterocyclic ring selected from aziridine, azetidine, pyrollidine, piperidine, morpholine, piperazine, homopiperazine, 2,5-diazabicyclo[2,2,1]heptane and –3,7-diazabicyclo[3,3,0]octane, wherein said phenyl, benzyl or said heterocyclic ring are independently optionally substituted by $C_1$-$C_3$alkyl, F. In a further preferred embodiment, $R_7$ is H, $C_1$-$C_3$alkyl, $C_1$-$C_3$alkoxy, $C_1$-$C_3$alkyl substituted with phenyl, benzyl or a heterocyclic ring selected from pyrollidine, piperidine, morpholine, piperazine, homopiperazine, wherein said phenyl, benzyl or said heterocyclic ring are independently optionally substituted by $C_1$-$C_3$alkyl.

In a further preferred embodiment, said $R_9$ is H, $C_1$-$C_3$alkyl substituted with OH, CN, COOH, $COOC_1$-$C_3$alkyl, $C_1$-$C_3$alkoxy, OC(O)H, OC(O)—$C_1$-$C_3$alkyl, C(O)N($R_6$)$OR_7$, $OC_1$-$C_3$alkylene-C(O)OH, —$OC_1$-$C_3$alkylene-C(O)$OC_1$-$C_3$alkyl, —$OC_1$-$C_3$alkylene-C(O)N($R_6$)$OR_7$, —$S(O_{0-2})C_1$-$C_3$alkyl. In a further preferred embodiment, said $R_9$ is H, $C_1$-$C_3$alkyl substituted with OH, CN, COOH, $COOC_1$-$C_3$alkyl, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$.

In a further preferred embodiment, said $R_{10}$ and $R_{11}$ are each independently H, $C_1$-$C_3$alkyl optionally substituted with OH, CN, COOH, $COOC_1$-$C_3$, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$, $S(O_{0-2})C_1$-$C_3$alkyl; or together with the nitrogen atom to which they are attached form a heterocyclic ring, wherein preferably said heterocyclic ring is selected from aziridine, azetidine, pyrollidine, piperidine, morpholine, piperazine and homopiperazine, wherein said heterocyclic ring is optionally substituted with $C_1$-$C_3$ alkyl. In a further preferred embodiment, said $R_{10}$ and $R_{11}$ are each independently H, $C_1$-$C_3$alkyl optionally substituted with OH, CN, COOH, $COOC_1$-$C_3$, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$, $S(O_{0-2})C_1$-$C_3$alkyl; or together with the nitrogen atom to which they are attached form a heterocyclic ring, wherein preferably said heterocyclic ring is selected from pyrollidine, piperidine, morpholine, piperazine and homopiperazine, wherein said heterocyclic ring is optionally substituted with $C_1$-$C_3$ alkyl.

In a further very preferred embodiment, said X—$R_2$ represents $C_1$-$C_3$alkylene substituted with CN, C(O)OH, $C(O)OC_1$-$C_3$alkyl, C(O)N($R_6$)$OR_7$, CHO, OC(O)H, $OC_1$-$C_3$alkylene-C(O)OH, $OC_1$-$C_3$alkylene-C(O)N($R_6$)$OR_7$, OC(O)—$C_1$-$C_3$alkyl, C(O)N($R_6$)$OR_7$, $CR_8$=N—$OR_9$; $C(O)OC_1$-$C_3$alkyl, CHO, C(O)N($R_6$)$OR_7$, $S(O_{0-2})C_1$-$C_3$alkyl, $CR_8$=N—$OR_9$, $CR_8$=N—$NR_{10}R_{11}$, $CR_8$=$NR_{12}$ or $CR_8$=N—$ONO_2$, wherein further preferably, said $R_6$ is H or $CH_3$; said $R_7$ is H, $C_1$-$C_3$alkyl, $C_1$-$C_3$alkoxy, $C_1$-$C_3$alkyl substituted with phenyl, benzyl or a heterocyclic ring selected from pyrollidine, piperidine, morpholine, piperazine, homopiperazine, wherein said phenyl, benzyl or said heterocyclic ring are independently optionally substituted by $C_1$-$C_3$alkyl; said $R_8$ is H or $CH_3$; said $R_9$ is H, $C_1$-$C_3$alkyl substituted with OH, CN, COOH, $COOC_1$-$C_3$alkyl, $C_1$-$C_3$alkoxy, OC(O)H, OC(O)—$C_1$-$C_3$alkyl, C(O)N($R_6$)$OR_7$, $OC_1$-$C_3$alkylene-C(O)OH, $OC_1$-$C_3$alkylene-C(O)$OC_1$-$C_3$alkyl, $OC_1$-$C_3$alkylene-C(O)N($R_6$)$OR_7$.

In a further very preferred embodiment, said X—$R_2$ represents $C_1$-$C_3$alkylene substituted with CN, C(O)OH, $C(O)OC_1$-$C_3$alkyl, C(O)N($R_6$)$OR_7$, CHO, OC(O)H, $OC_1$-$C_3$alkylene-C(O)OH, $OC_1$-$C_3$alkylene-C(O)N($R_6$)$OR_7$, OC(O)—$C_1$-$C_3$alkyl, C(O)N($R_6$)$OR_7$, $CR_8$=N—$OR_9$; $C(O)OC_1$-$C_3$alkyl, CHO, C(O)N(R)$OR_7$, $S(O_{0-2})C_1$-$C_3$alkyl, $CR_8$=N—$OR_9$, $CR_8$=N—$NR_{10}R_{11}$, wherein further preferably, said $R_6$ is H or $CH_3$; said $R_7$ is H, $C_1$-$C_3$alkyl, $C_1$-$C_3$alkoxy, $C_1$-$C_3$alkyl substituted with phenyl, benzyl or a heterocyclic ring selected from pyrollidine, piperidine, morpholine, piperazine, homopiperazine, wherein said phenyl, benzyl or said heterocyclic ring are independently optionally substituted by $C_1$-$C_3$alkyl; said $R_8$ is H or $CH_3$; said $R_9$ is H, $C_1$-$C_3$alkyl substituted with OH, CN, COOH, $COOC_1$-$C_3$alkyl, $C_1$-$C_3$alkoxy, OC(O)H, OC(O)—$C_1$-$C_3$alkyl, $C(O)N(R_6)OR_7$, $OC_1$-$C_3$alkylene-C(O)OH, $OC_1$-$C_3$alkylene-C(O)$OC_1$-$C_3$alkyl, $OC_1$-$C_3$alkylene-C(O)$N(R_6)OR_7$; said $R_{10}$ and $R_{11}$ are each independently H, $C_1$-$C_3$alkyl optionally substituted with OH, CN, COOH, $COOC_1$-$C_3$, $C_1$-$C_3$alkoxy, OC(O)H, OC(O)—$C_1$-$C_3$alkyl, $C(O)N(R_6)OR_7$, $OC_1$-$C_3$alkylene-C(O)OH, $OC_1$-$C_3$alkylene-C(O)$OC_1$-$C_3$alkyl, $OC_1$-$C_3$alkylene-C(O)$N(R_6)OR_7$, $S(O_{0-2})C_1$-$C_3$alkyl; or together with the nitrogen atom to which they are attached form a heterocyclic ring, wherein preferably said heterocyclic ring is selected from pyrollidine, piperidine, morpholine, piperazine and homopiperazine, wherein said heterocyclic ring is optionally substituted with $C_1$-$C_3$ alkyl.

In a further very preferred embodiment, said X—$R_2$ represents $C_1$-$C_3$alkylene substituted with CN, C(O)OH, $C(O)OC_1$-$C_3$alkyl, $C(O)N(R_6)OR_7$, CHO, OC(O)H, $OC_1$-$C_3$alkylene-C(O)OH, $OC_1$-$C_3$alkylene-C(O)$N(R_6)OR_7$, OC(O)—$C_1$-$C_3$alkyl, $C(O)N(R_6)OR_7$, $CR_8$=N—$OR_9$; $C(O)OC_1$-$C_3$alkyl, CHO, $C(O)N(R_6)OR_7$, $CR_8$=N—$OR_9$, wherein further preferably, said $R_6$ is H or $CH_3$; said $R_7$ is H, $C_1$-$C_3$alkyl, $C_1$-$C_3$alkoxy, $C_1$-$C_3$alkyl substituted with phenyl, benzyl or a heterocyclic ring selected from pyrollidine, piperidine, morpholine, piperazine, homopiperazine, wherein said phenyl, benzyl or said heterocyclic ring are independently optionally substituted by $C_1$-$C_3$alkyl; said $R_8$ is H or $CH_3$; said $R_9$ is H, $C_1$-$C_3$alkyl substituted with OH, CN, COOH, $COOC_1$-$C_3$alkyl, $C_1$-$C_3$alkoxy, OC(O)H, OC(O)—$C_1$-$C_3$alkyl, $C(O)N(R_6)OR_7$, $OC_1$-$C_3$alkylene-C(O)OH, $OC_1$-$C_3$alkylene-C(O)$OC_1$-$C_3$alkyl, $OC_1$-$C_3$alkylene-C(O)$N(R_6)OR_7$.

In a further very preferred embodiment, said X—$R_2$ represents $CR_8$=N—$OR_9$, preferably (E)-$CR_8$=N—$OR_9$, wherein said $R_5$ is H or $CH_3$, preferably wherein said $R_5$ is H, and wherein said $R_9$ is H or $C_1$-$C_3$ alkyl optionally substituted with OH or $C_1$-$C_3$ alkyl optionally substituted with OH.

In a further very preferred embodiment, said X—$R_2$ represents CH=N—$OR_9$, preferably (E)-CH=N—$OR_9$, wherein said $R_9$ is H or $C_1$-$C_3$ alkyl optionally substituted with OH or CN, and wherein preferably said $R_9$ is H or $C_1$-$C_3$ alkyl substituted with OH or CN; and wherein further preferably said $R_9$ is H or $C_1$-$C_3$ alkyl substituted with OH.

Without being bound this theory, it is believed that the functionalization of the group $R_2$ and thus the group X—$R_2$, allows an increased interaction with the PDE5 enzyme and thus an increased inhibition effect. In particular, $R_2$ with an oxime functionality, and hereby in particular with a trans-geometry of the oxime functionality has been found to be highly beneficial.

In a further preferred embodiment, said $R_1$ is $C_1$-$C_3$ alkyl; said $R_2$ is CH=N—$OR_9$; preferably (E)-CH=N—$OR_9$, wherein said $R_9$ is H or $C_1$-$C_3$ alkyl optionally substituted with OH or $C_1$-$C_3$ alkyl optionally substituted with OH; $R_3$ is $C_1$-$C_6$ alkyl; said $R_4$ is $C_1$-$C_6$alkoxy; said $R_5$ is $SO_2NR_{13}R_{14}$ wherein $R_{13}$ and $R_{14}$ are each independently H or together with the nitrogen atom to which they are attached form a mono-cyclic ring selected from imidazol, aziridine, azetidine, pyrrolidine, piperidine, morpholine, piperazine and homopiperazine optionally substituted with $R_{15}$; wherein said $R_{15}$ is $C_1$-$C_4$alkyl optionally substituted with halogen, OH, ONO, $ONO_2$, $C_1$-$C_3$alkoxy, $COOR_{16}$, $NR_{17}R_{18}$, C=$NR_{19}$; $R_{16}$ is H, or $C_1$-$C_4$alkyl optionally substituted with F, OH, ONO, $ONO_2$; said $R_{17}$ and $R_{18}$ are each independently H or $C_1$-$C_4$alkyl optionally substituted with ONO, $ONO_2$; said $R_{19}$ is $C_1$-$C_4$alkyl optionally substituted with F, ONO, $ONO_2$.

In a further preferred embodiment, said $R_1$ is $C_1$-$C_3$ alkyl; said $R_2$ is CH=N—$OR_9$; preferably (E)-CH=N—$OR_9$, wherein said $R_9$ is H or $C_1$-$C_3$ alkyl optionally substituted with OH or CN; $R_3$ is $C_1$-$C_6$ alkyl; said $R_4$ is $C_1$-$C_6$ alkoxy; said $R_5$ is $SO_2NR_{13}R_{14}$ wherein $R_{13}$ and $R_{14}$ are each independently H or together with the nitrogen atom to which they are attached form a mono-cyclic ring selected from imidazol, aziridine, azetidine, pyrrolidine, piperidine, morpholine, piperazine and homopiperazine optionally substituted with $R_{15}$; wherein said $R_{15}$ is $C_1$-$C_4$alkyl optionally substituted with halogen, OH, ONO, $ONO_2$, $C_1$-$C_3$alkoxy, $COOR_{16}$, $NR_{17}R_{18}$, C=$NR_{19}$; $R_{16}$ is H, or $C_1$-$C_4$alkyl optionally substituted with F, OH, ONO, $ONO_2$; said $R_{17}$ and $R_{18}$ are each independently H or $C_1$-$C_4$alkyl optionally substituted with ONO, $ONO_2$; said $R_{19}$ is $C_1$-$C_4$alkyl optionally substituted with F, ONO, $ONO_2$.

Further very preferred embodiments of the present invention are represented by individual compounds of formula I or pharmaceutically acceptable salts, solvates or hydrates thereof.

Thus, in another very preferred embodiment, said compound of formula I is selected from (E)-2-(2-ethoxy-5-((4-methylpiperazin-1-yl)sulfonyl)phenyl)-5-methyl-4-oxo-7-propyl-3,4-dihydropyrrolo[2,1-][1,2,4]triazine-6-carbaldehyde oxime

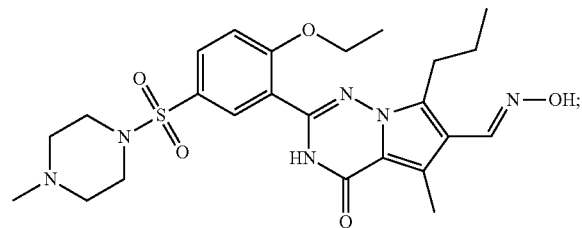

(1a)

2-(2-ethoxy-5-((4-methylpiperazin-1-yl)sulfonyl)phenyl)-6-(hydroxymethyl)-5-methyl-7-propylpyrrolo[2,1-f][1,2,4]triazin-4(3H)-one

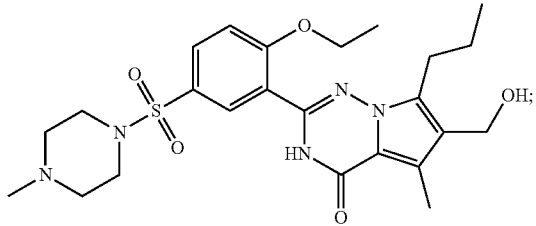

(1b)

(2-(2-ethoxy-5-((4-methylpiperazin-1-yl)sulfonyl)
phenyl)-5-methyl-4-oxo-7-propyl-3,4-dihydropyr-
rolo[2,1-f][1,2,4]triazin-6-yl)methyl acetate Methyl 2-(2-ethoxy-5-((4-methylpiperazin-1-yl)
sulfonyl)phenyl)-5-methyl-4-oxo-7-propyl-3,4-dihy-
dropyrrolo[2,1-][1,2,4]triazine-6-carboxylate

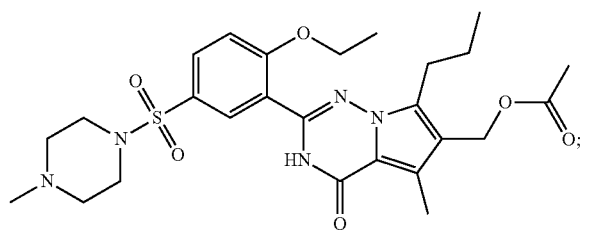

(1c)

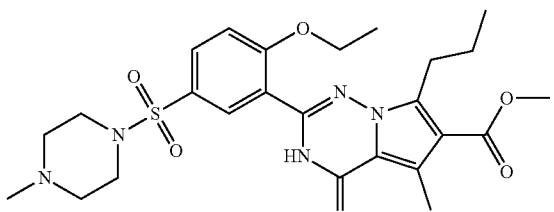

(1f)

2-(2-ethoxy-5-((4-methylpiperazin-1-yl)sulfonyl)
phenyl)-5-methyl-4-oxo-7-propyl-3,4-dihydropyr-
rolo[2,1-f][1,2,4]triazine-6-carboxylic acid 2-(2-ethoxy-5-((4-methylpiperazin-1-yl)sulfonyl)
phenyl)-N-hydroxy-5-methyl-4-oxo-7-propyl-3,4-
dihydropyrrolo[2,1-f][1,2,4]triazine-6-carboxamide

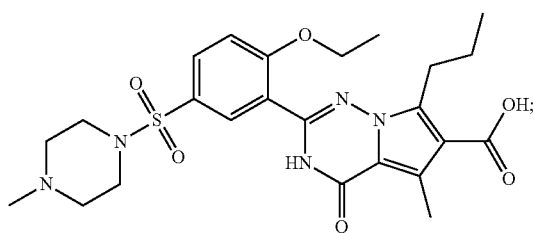

(1d)

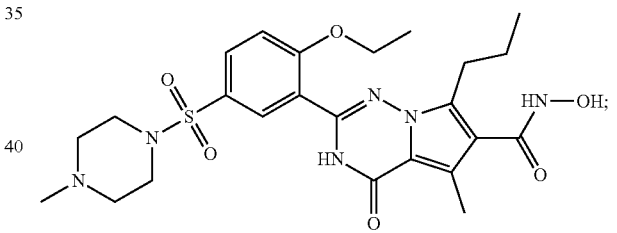

(1g)

N-(benzyloxy)-2-(2-ethoxy-5-((4-methylpiperazin-1-
yl)sulfonyl)phenyl)-5-methyl-4-oxo-7-propyl-3,4-
dihydropyrrolo[2,1-f][1,2,4]triazine-6-carboxamide 2-((2-(2-ethoxy-5-((4-methylpiperazin-1-yl)sulfonyl)
phenyl)-5-methyl-4-oxo-7-propyl-3,4-dihydropyr-
rolo[2,1-f][1,2,4]triazin-6-yl)methoxy)acetic acid

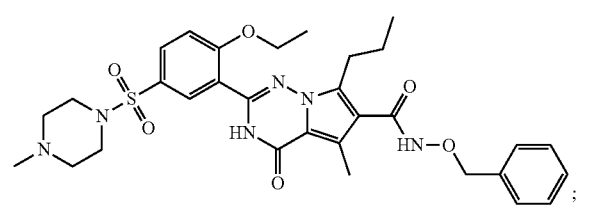

(1e)

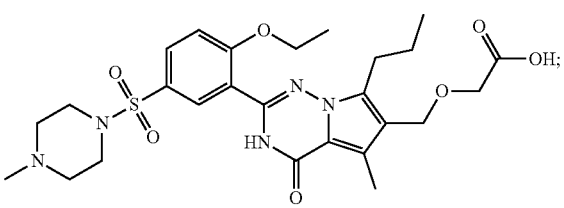

(1h)

21

2-((2-(2-ethoxy-5-((4-methylpiperazin-1-yl)sulfonyl) phenyl)-5-methyl-4-oxo-7-propyl-3,4-dihydropyrrolo[2,1-f][1,2,4]triazin-6-yl)methoxy)-N-hydroxy-N-methylacetamide

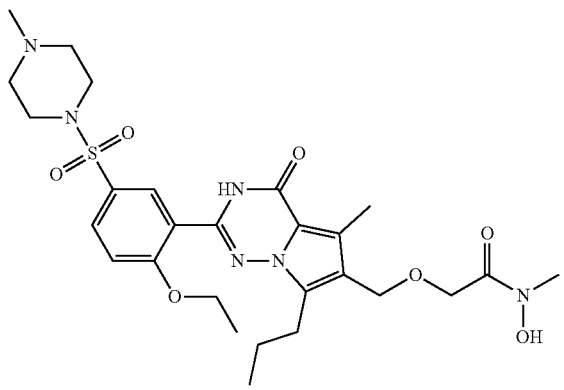
(1i)

2-(2-ethoxy-5-((4-methylpiperazin-1-yl)sulfonyl) phenyl)-5-methyl-4-oxo-7-propyl-3,4-dihydropyrrolo[2,1-f][1,2,4]triazine-6-carbaldehyde

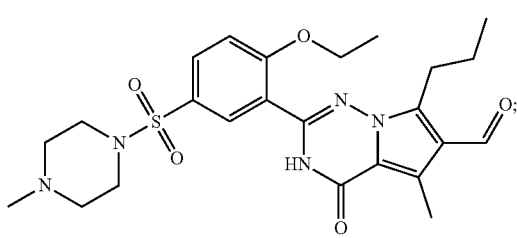
(1j)

6-(1,3-dihydroxypropyl)-2-(2-ethoxy-5-((4-methylpiperazin-1-yl)sulfonyl) phenyl)-5-methyl-7-propylpyrrolo[2,1-f][1,2,4]triazin-4(3H)-one

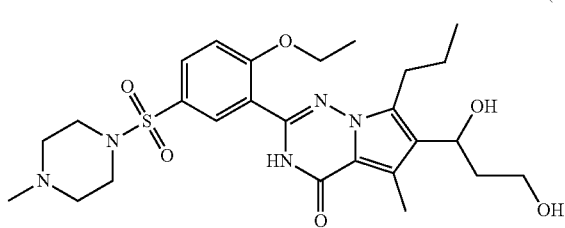
(1k)

22

5-methyl-2-(5-((4-methylpiperazin-1-yl)sulfonyl)-2-propoxyphenyl)-4-oxo-7-propyl-3,4-dihydropyrrolo[2,1-f][1,2,4]triazine-6-carbaldehyde

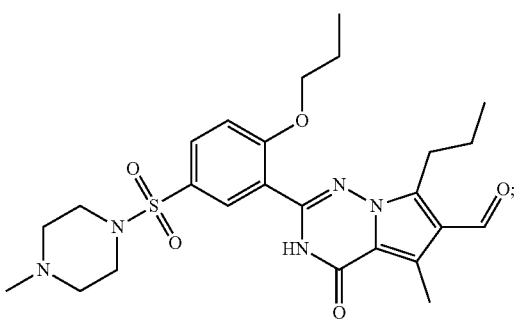
(1l)

2-(5-((4-(2-hydroxyethyl)piperazin-1-yl)sulfonyl)-2-propoxyphenyl)-5-methyl-4-oxo-7-propyl-3,4-dihydropyrrolo[2,1-f][1,2,4]triazine-6-carbaldehyde (1m)

2-(5-((4-(2-hydroxyethyl)piperazin-1-yl)sulfonyl)-2-propoxyphenyl)-6-(hydroxymethyl)-5-methyl-7-propylpyrrolo[2,1-][1,2,4]triazin-4(3H)-one

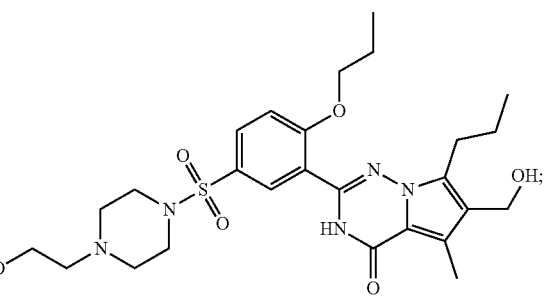
(1n)

23

(E)-5-methyl-2-(5-((4-methylpiperazin-1-yl)sulfonyl)-2-propoxyphenyl)-4-oxo-7-propyl-3,4-dihydropyrrolo[2,1-f][1,2,4]triazine-6-carbaldehyde O-methyl oxime

24

(E)-2-(5-((4-(2-hydroxyethyl)piperidin-1-yl)sulfonyl)-2-propoxyphenyl)-5-methyl-4-oxo-7-propyl-3,4-dihydropyrrolo[2,1-f][1,2,4]triazine-6-carbaldehyde oxime (1o)

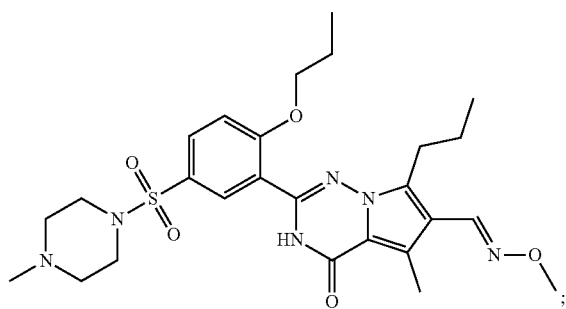

2-(5-((4-(2-hydroxyethyl)piperidin-1-yl)sulfonyl)-2-propoxyphenyl)-5-methyl-4-oxo-7-propyl-3,4-dihydropyrrolo[2,1-f][1,2,4]triazine-6-carbaldehyde (1r)

ethyl-3-(2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)-3-hydroxypropanoate (1p)

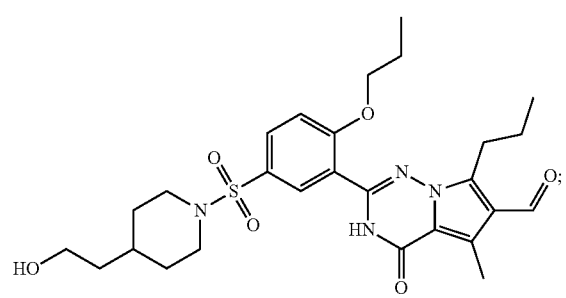

2-(1-((3-(6-formyl-5-methyl-4-oxo-7-propyl-3,4-dihydropyrrolo[2,1-f][1,2,4]triazin-2-yl)-4-propoxyphenyl)sulfonyl)piperidin-4-yl)ethyl nitrate (1s)

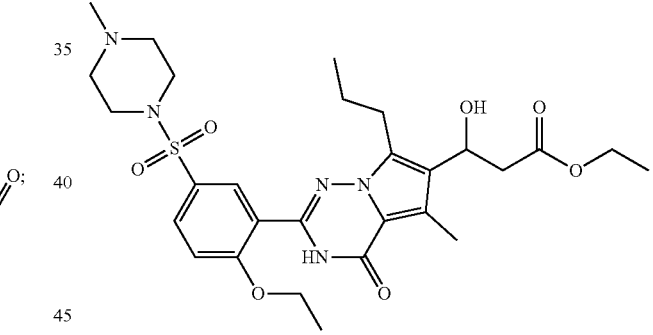

3-(2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)-N,3-dihydroxypropanamide (1q)

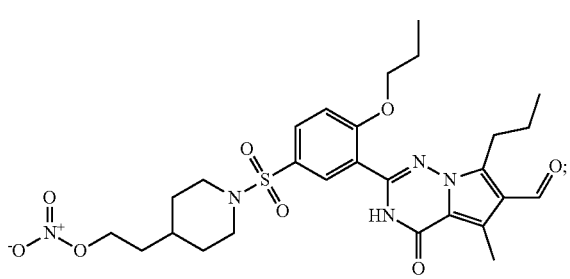

(1t)

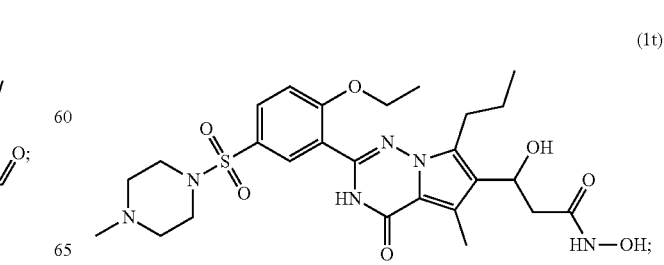

25

3-(2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)-3-hydroxypropanenitrile

26

(E)-2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde oxime

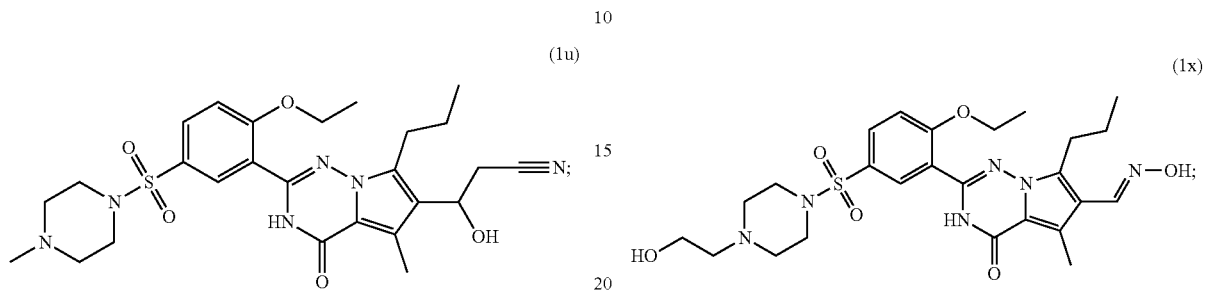

(1u)

(1x)

(E)-2-(1-((3-(6-((hydroxyimino)methyl)-5-methyl-4-oxo-7-propyl-3,4-dihydropyrrolo[2,1-f][1,2,4]triazin-2-yl)-4-propoxyphenyl)sulfonyl)piperidin-4-yl) ethyl nitrate 2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde O-methyloxime

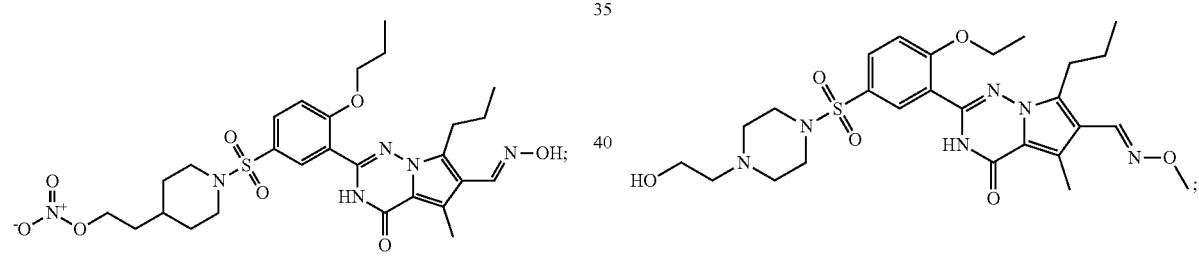

(1v)

(1y)

2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde (E)-2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde O-(2-hydroxyethyl) oxime

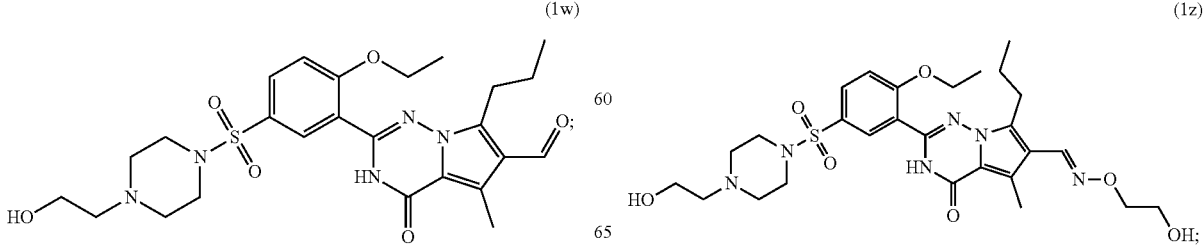

(1w)

(1z)

| 27 | 28 |
|---|---|
| 2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde | (E)-2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde O-(2-hydroxyethyl) oxime |

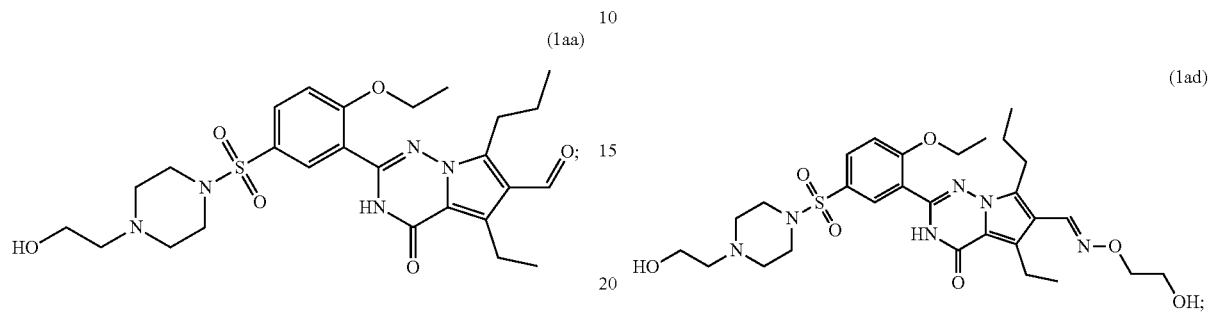

(1aa)

(E)-2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde oxime (1ad)

2-(4-((4-ethoxy-3-(6-formyl-5-methyl-4-oxo-7-propyl-3,4-dihydropyrrolo[2,1-f][1,2,4]triazin-2-yl)phenyl)sulfonyl)piperazin-1-yl)ethyl nitrate

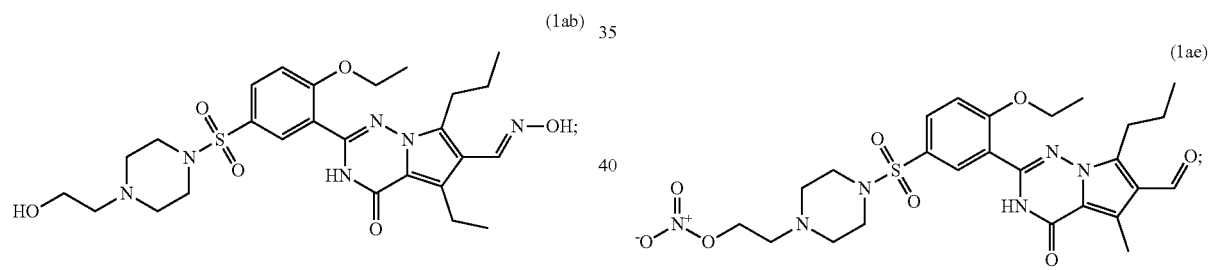

(1ab)

(E)-2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde O-methyl oxime (1ae)

(E)-2-(4-((4-ethoxy-3-(6-((hydroxyimino)methyl)-5-methyl-4-oxo-7-propyl-3,4-dihydropyrrolo[2,1-f][1,2,4]triazin-2-yl)phenyl)sulfonyl)piperazin-1-yl)ethyl nitrate

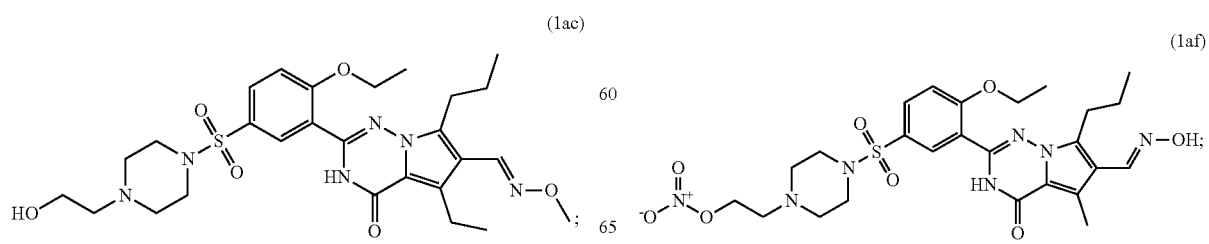

(1ac)

(1af)

29

2-(4-((4-ethoxy-3-(5-ethyl-6-formyl-4-oxo-7-propyl-3,4-dihydropyrrolo[2,1-f][1,2,4]triazin-2-yl)phenyl)sulfonyl)piperazin-1-yl)ethyl nitrate (1ag)

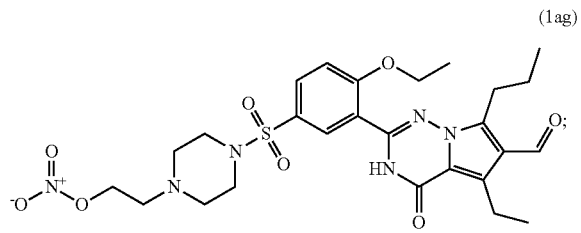

(E)-2-(4-((4-ethoxy-3-(5-ethyl-6-((hydroxyimino)methyl)-4-oxo-7-propyl-3,4-dihydropyrrolo[2,1-f][1,2,4]triazin-2-yl)phenyl)sulfonyl)piperazin-1-yl)ethyl nitrate (1ah)

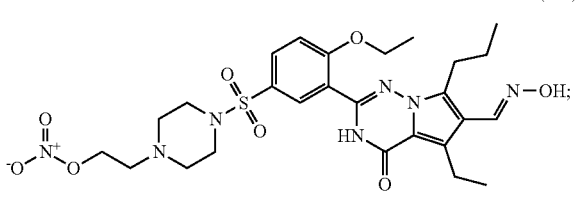

30

(E)-2-(4-((4-ethoxy-3-(6-((methoxyimino)methyl)-5-methyl-4-oxo-7-propyl-3,4-dihydropyrrolo[2,1-f][1,2,4]triazin-2-yl)phenyl)sulfonyl)piperazin-1-yl)ethyl nitrate (1ai)

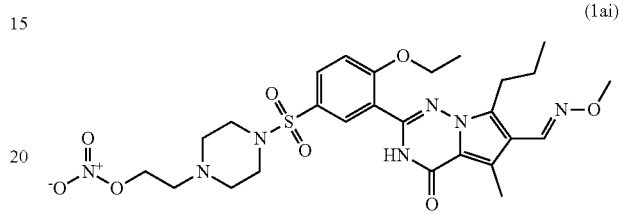

(E)-2-(4-((4-ethoxy-3-(6-(((2-hydroxyethoxy)imino)methyl)-5-methyl-4-oxo-7-propyl-3,4-dihydropyrrolo[2,1-f][1,2,4]triazin-2-yl)phenyl)sulfonyl)piperazin-1-yl)ethyl nitrate (1ak)

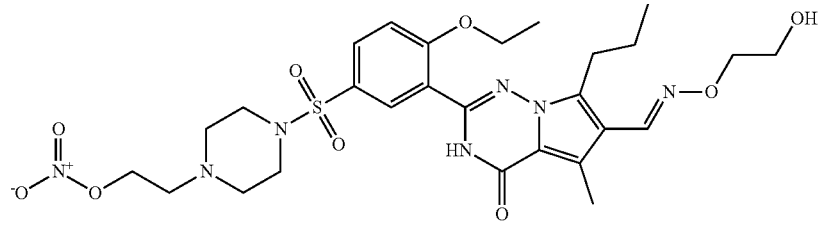

(E)-2-(2-ethoxy-5-((4-(2-hydroxyethyl)piperidin-1-yl)sulfonyl)phenyl)-5-methyl-4-oxo-7-propyl-3,4-dihydropyrrolo[2,1-f][1,2,4]triazine-6-carbaldehyde oxime (1al)

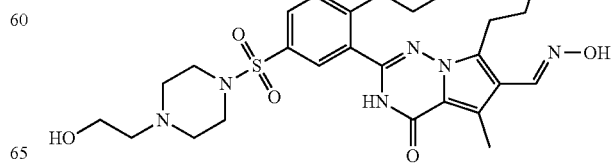

31

(E)-2-(1-((4-ethoxy-3-(6-((hydroxyimino)methyl)-5-methyl-4-oxo-7-propyl-3,4-dihydropyrrolo[2,1-f][1,2,4]triazin-2-yl)phenyl)sulfonyl)piperidin-4-yl)ethyl nitrate

32

(Z)-2-(1-((3-(6-((hydroxyimino)methyl)-5-methyl-4-oxo-7-propyl-3,4-dihydropyrrolo[2,1-f][1,2,4]triazin-2-yl)-4-propoxyphenyl)sulfonyl)piperidin-4-yl) ethyl nitrate

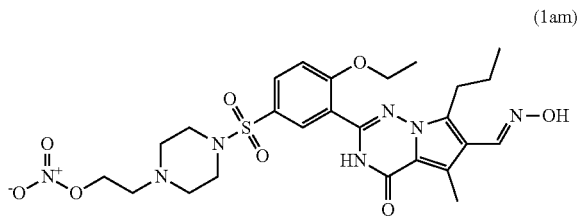

(1am)

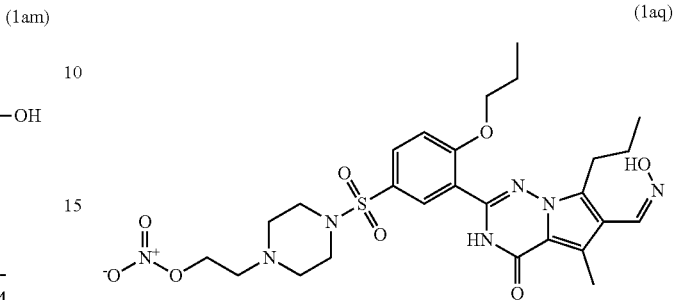

(1aq)

(E)-2-(2-ethoxy-5-((4-(3-hydroxypropyl)piperazin-1l-yl)sulfonyl)phenyl)-5-methyl-4-oxo-7-propyl-3,4-dihydropyrrolo[2,1-f][1,2,4]triazine-6-carbaldehyde oxime In another very preferred embodiment, said compound of formula I is selected from (E)-2-(5-((4-(2-hydroxyethyl)piperidin-1-yl)sulfonyl)-2-propoxyphenyl)-5-methyl-4-oxo-7-propyl-3,4-dihydropyrrolo[2,1-f][1,2,4]triazine-6-carbaldehyde oxime (1r); and (E)-2-(1-((3-(6-((hydroxyimino)methyl)-5-methyl-4-oxo-7-propyl-3,4-dihydropyrrolo[2,1-f][1,2,4]triazin-2-yl)-4-propoxyphenyl)sulfonyl)piperidin-4-yl)ethyl nitrate (1v).

In another very preferred embodiment, said compound of formula I is (E)-2-(5-((4-(2-hydroxyethyl)piperidin-1-yl)sulfonyl)-2-propoxyphenyl)-5-methyl-4-oxo-7-propyl-3,4-dihydropyrrolo[2,1-f][1,2,4]triazine-6-carbaldehyde oxime (1r).

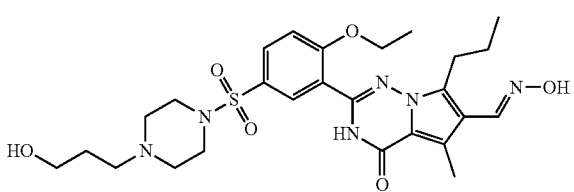

(1an)

(E)-3-(4-((4-ethoxy-3-(6-((hydroxyimino)methyl)-5-methyl-4-oxo-7-propyl-3,4-dihydropyrrolo[2,1-f][1,2,4]triazin-2-yl)phenyl)sulfonyl)piperazin-1-yl)propyl nitrate In another very preferred embodiment, said compound of formula I is (E)-2-(1-((3-(6-((hydroxyimino)methyl)-5-methyl-4-oxo-7-propyl-3,4-dihydropyrrolo[2,1-f][1,2,4]triazin-2-yl)-4-propoxyphenyl)sulfonyl)piperidin-4-yl)ethyl nitrate (1v).

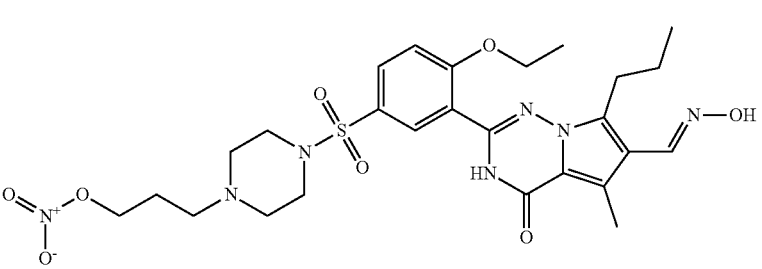

(1ao)

2-(2-ethoxy-5-((4-(3-hydroxypropyl)piperazin-1-yl)sulfonyl)phenyl)-5-methyl-7-propylpyrrolo[2,1-f][1,2,4]triazin-4(3H)-one In another very preferred embodiment, said compound of formula I is (E)-2-(2-ethoxy-5-((4-methylpiperazin-1-yl)sulfonyl)phenyl)-5-methyl-4-oxo-7-propyl-3,4-dihydropyrrolo[2,1-f][1,2,4]triazine-6-carbaldehyde oxime (1a).

In another very preferred embodiment, said compound of formula I is (E)-5-methyl-2-(5-((4-methylpiperazin-1-yl)sulfonyl)-2-propoxyphenyl)-4-oxo-7-propyl-3,4-dihydropyrrolo[2,1-f][1,2,4]triazine-6-carbaldehyde O-methyl oxime (1o).

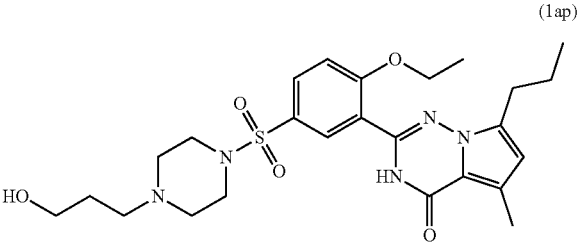 [SMILES: CCCc1cc(C)c2c(=O)[nH]c(-c3cc(S(=O)(=O)N4CCN(CCCO)CC4)ccc3OCC)nn12]

(1ap)

In another very preferred embodiment, said compound of formula I is (E)-2-(5-((4-(2-hydroxyethyl)piperidin-1-yl)sulfonyl)-2-propoxyphenyl)-5-methyl-4-oxo-7-propyl-3,4-dihydropyrrolo[2,1-f][1,2,4]triazine-6-carbaldehyde oxime (1r).

In another very preferred embodiment, said compound of formula I is ethyl-3-(2-(2-ethoxy-5-((4-methylpiperazin-1- yl)sulfonyl)phenyl)-5-methyl-4-oxo-7-propyl-3,4-dihydropyrrolo[2,1-f][1,2,4]triazin-6-yl)-3-hydroxypropanoate (1s).

In another very preferred embodiment, said compound of formula I is 3-(2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)-N,3-dihydroxypropanamide (1t).

In another very preferred embodiment, said compound of formula I is 3-(2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)-3-hydroxypropanenitrile (1u).

In another very preferred embodiment, said compound of formula I is 2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde (1w).

In another very preferred embodiment, said compound of formula I is (E)-2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde O-(2-hydroxyethyl) oxime (1z).

In another very preferred embodiment, said compound of formula I is (E)-2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde oxime (1ab).

In another very preferred embodiment, said compound of formula I is (E)-2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde O-(2-hydroxyethyl) oxime (1ad).

In another very preferred embodiment, said compound of formula I is (E)-2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde O-(2-hydroxyethyl) oxime (1ad).

In another very preferred embodiment, said compound of formula I is 2-(4-((4-ethoxy-3-(6-formyl-5-methyl-4-oxo-7-propyl-3,4-dihydropyrrolo[2,1-f][1,2,4]triazin-2-yl)phenyl)sulfonyl)piperazin-1-yl)ethyl nitrate (1ae).

In another very preferred embodiment, said compound of formula I is (E)-2-(4-((4-ethoxy-3-(6-((hydroxyimino)methyl)-5-methyl-4-oxo-7-propyl-3,4-dihydropyrrolo[2,1-f][1,2,4]triazin-2-yl)phenyl)sulfonyl)piperazin-1-yl)ethyl nitrate (1a).

In another very preferred embodiment, said compound of formula I is (E)-2-(4-((4-ethoxy-3-(5-ethyl-6-((hydroxyimino)methyl)-4-oxo-7-propyl-3,4-dihydropyrrolo[2,1-f][1,2,4]triazin-2-yl)phenyl)sulfonyl)piperazin-1-yl)ethyl nitrate (1ab).

In another very preferred embodiment, said compound of formula I is (E)-2-(4-((4-ethoxy-3-(6-(((2-hydroxyethoxy)imino)methyl)-5-methyl-4-oxo-7-propyl-3,4-dihydropyrrolo[2,1-f][1,2,4]triazin-2-yl)phenyl)sulfonyl)piperazin-1-yl)ethyl nitrate (1ak).

In another very preferred embodiment, said compound of formula I is (E)-2-(2-ethoxy-5-((4-(2-hydroxyethyl)piperidin-1-yl)sulfonyl)phenyl)-5-methyl-4-oxo-7-propyl-3,4-dihydropyrrolo[2,1-f][1,2,4]triazine-6-carbaldehyde oxime (1al).

In another very preferred embodiment, said compound of formula I is (E)-2-(1-((4-ethoxy-3-(6-((hydroxyimino)methyl)-5-methyl-4-oxo-7-propyl-3,4-dihydropyrrolo[2,1-f][1,2,4]triazin-2-yl)phenyl)sulfonyl)piperidin-4-yl)ethyl nitrate (1am).

In another very preferred embodiment, said compound of formula I is (E)-2-(2-ethoxy-5-((4-(3-hydroxypropyl)piperazin-1-yl)sulfonyl)phenyl)-5-methyl-4-oxo-7-propyl-3,4-dihydropyrrolo[2,1-f][1,2,4]triazine-6-carbaldehyde oxime (1an).

In another very preferred embodiment, said compound of formula I is (E)-3-(4-((4-ethoxy-3-(6-((hydroxyimino)methyl)-5-methyl-4-oxo-7-propyl-3,4-dihydropyrrolo[2,1-f][1,2,4]triazin-2-yl)phenyl)sulfonyl)piperazin-1-yl)propyl nitrate (1ao).

It has been shown that compounds of the present invention are potent and selective inhibitors of cGMP specific PDE. Furthermore, it has been found that the compounds of the present invention can be tailored to become dual-pharmacology NO-releasing PDE5 inhibitors which are believed to release NO in addition to its PDE 5 inhibition in a more than additive fashion. Thus, compounds of formula I are of interest for use in therapy, specifically for the treatment of a variety of conditions where inhibition of cGMP specific PDE is thought to be beneficial.

Thus, in a further aspect, the present invention provides for a pharmaceutical composition comprising at least one of the inventive compound of formula I, or a pharmaceutically acceptable salt, solvate or hydrate thereof, and a pharmaceutically acceptable excipient, adjuvant, or carrier. In another aspect, the present invention provides for a pharmaceutical composition comprising exactly one inventive compound of formula I, or a pharmaceutically acceptable salt, solvate or hydrate thereof, and a pharmaceutically acceptable excipient, adjuvant, or carrier. Pharmaceutically acceptable excipient, adjuvant, or carrier are known to the skilled person in the art.

In another aspect, the present invention provides for a compound of formula I, or a pharmaceutically acceptable salt, solvate or hydrate thereof, for use as a pharmaceutical. In again another aspect, the present invention provides for a compound of formula I, or a pharmaceutically acceptable salt, solvate or hydrate thereof, for use as an animal medicament.

It has surprisingly been found that the compounds of the present invention are very potent and selective inhibitors of PDE5. Furthermore, we have surprisingly found that the compounds of the present invention can be tailored to become dual-pharmacology NO-releasing PDE5 inhibitors which are believed to release NO in addition to its PDE 5 inhibition in a more than additive fashion. Moreover, it has surprisingly been found that preferred compounds of the present invention show even a significantly higher PDE5 inhibition activity as compared to known PDE5 inhibitors such as sildenafil. As a consequence, the novel pyrrolo triazine compounds of the present invention are useful in the therapy and prophylaxis of diseases which are associated with a disturbed cGMP balance. In particular, the compounds of the present invention are potent and selective inhibitors of cyclic guanosine 3'-5'-monophosphate specific phosphodiesterase 5 (cGMP specific PDE5) and thus have utility in variety of therapeutic areas where such inhibition is thought to be beneficial. Some of the preferred therapeutic areas are wound healing, in particular chronic wound healing, diabetic foot, diabetic foot ulcer, leg ulcer, Raynaud's, male erectile dysfunction, female sexual dysfunction, Alzheimer's disease, diabetes, hair loss, skin aging, vascular aging, pulmonary artery hypertension and chronic heart failure.

As a consequence of the selective PDE5 inhibition exhibited by compounds of the present invention, cGMP levels are expected to be elevated, which in turn can give rise to beneficial anti-platelet, anti-vasospastic, vasodilatory, natriuretic and diuretic activities as well as potentiation of the effects of endothelium-derived relaxing factor (EDRF) nitric oxide (NO), nitrovasodilators, atrial natriuretic factor (ANF), brain natriuretic peptide (BNP), C-type natriuretic peptide (CNP) and endothelium-dependent relaxing agents such as bradykinin, acetylcholine and 5-HT$_1$. The compounds of formula I therefore have utility in the treatment of a number of disorders, including stable, unstable and variant (Prinzmetal) angina, hypertension, pulmonary hypertension, congestive heart failure, renal failure, atherosclerosis, conditions of reduced blood vessel patency (e.g. post-percutaneous transluminal coronary angioplasty), peripheral vascular disease, vascular disorders such as Raynaud's disease, inflammatory diseases, stroke, bronchitis, chronic asthma, allergic asthma, allergic rhinitis, diabetes, glaucoma and diseases characterized by disorders of gut motility like irritable bowel syndrome, wound healing, in particular chronic wound healing, diabetic foot, diabetic foot ulcer, leg ulcer, Alzheimer's disease, hair loss, skin aging, vascular aging, pulmonary artery hypertension and chronic heart failure.

Thus, in another aspect, the present invention provides for a compound of formula I, or a pharmaceutical composition, or a pharmaceutically acceptable salt, solvate or hydrate thereof, for use in a method of treating or preventing a disease alleviated by inhibition of PDE-5 in a human or in a non-human mammal, preferably in a human. Preferably, said disease is selected from wound healing, chronic wound healing, diabetic foot ulcer, leg ulcer, Raynaud's disease, male erectile dysfunction, female sexual dysfunction, hair loss, skin aging, vascular aging, pulmonary artery hypertension; stable, unstable and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, diabetes, glaucoma or a disease characterized by disorders of gut motility like irritable bowel syndrome, liver fibrosis, Alzheimer's disease and chronic heart failure, wherein further preferably said disease is selected from wound healing, chronic wound healing, diabetic foot ulcer, leg ulcer, diabetic neuropathy, peripheral vascular disease, vascular disorders, Raynaud's disease, systemic sclerosis (SSc), scleroderma, pulmonary artery hypertension, diabetes, male erectile dysfunction, and wherein again further preferably said disease is selected from wound healing, chronic wound healing, diabetic foot ulcer, leg ulcer and diabetic neuropathy.

In again another aspect, the present invention provides for a compound of formula I, or a pharmaceutical composition, or a pharmaceutically acceptable salt, solvate or hydrate thereof, for use in a method of treating or preventing a disease by inhibition of PDE-5 in a human or in a non-human mammal, preferably in a human. In again another aspect, the present invention provides for a compound of formula I, or a pharmaceutical composition, or a pharmaceutically acceptable salt, solvate or hydrate thereof, for use in a method of treating a medical condition in a human or in a non-human mammal, preferably in a human, wherein for said medical condition inhibition of PDE5 is desired.

In again another aspect, the present invention provides use of a compound of formula I, or a pharmaceutical composition, or a pharmaceutically acceptable salt, solvate or hydrate thereof, for the manufacture of a medicament for the treatment or prevention of a disease by inhibition of PDE-5 in a human or in a non-human mammal, preferably in a human. In again another aspect, the present invention provides use of a compound of formula I, or a pharmaceutical composition, or a pharmaceutically acceptable salt, solvate or hydrate thereof, for the manufacture of a medicament for the treatment or prevention of a disease alleviated by inhibition of PDE-5 in a human or in a non-human mammal, preferably in a human. In again another aspect, the present invention provides use of a compound of formula I, or a pharmaceutical composition, or a pharmaceutically acceptable salt, solvate or hydrate thereof, for the manufacture of a medicament for the treatment a medical condition in a human or in a non-human mammal, preferably in a human, wherein for said medical condition inhibition of PDE5 is desired.

In again another aspect, the present invention provides for a method of treating or preventing a disease by inhibition of PDE-5 in a human or in a non-human mammal, preferably in a human, comprising administering to said human or said non-human mammal, preferably to said human an effective amount of a compound of formula I, or a pharmaceutical composition, or a pharmaceutically acceptable salt, solvate or hydrate thereof. In again another aspect, the present invention provides for a method of treating or preventing a disease alleviated by inhibition of PDE-5 in a human or in a non-human mammal, preferably in a human, comprising administering to said human or said non-human mammal, preferably to said human an effective amount of a compound of formula I, or a pharmaceutical composition, or a pharmaceutically acceptable salt, solvate or hydrate thereof. In again another aspect, the present invention provides for a method of treating a medical condition in a human or in a non-human mammal, preferably in a human, wherein for said medical condition inhibition of PDE5 is desired, comprising administering to said human or said non-human mammal, preferably to said human an effective amount of a compound of formula I, or a pharmaceutical composition, or a pharmaceutically acceptable salt, solvate or hydrate thereof.

In a preferred embodiment of the present invention, said disease or said a medical condition is selected from wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein preferably said disease is selected from wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension, diabetes, male erectile dysfunction, and wherein again further preferably said disease is selected from wound healing, preferably chronic wound healing, diabetic foot, diabetic foot ulcer, leg ulcer and diabetic neuropathy.

There is thus provided as a further aspect of the present invention a compound of formula I for use in the treatment of wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein preferably said disease is selected from wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension, diabetes, male erectile dysfunction, and wherein again further preferably said disease is selected from wound healing, preferably chronic wound healing, diabetic foot, diabetic foot ulcer, leg ulcer and diabetic neuropathy.

According to another aspect of the invention, there is provided the use of a compound of formula I for the manufacture of a medicament for the treatment of wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein preferably said disease is selected from wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension, diabetes, male erectile dysfunction, and wherein again further preferably said disease is selected from wound healing, preferably chronic wound healing, diabetic foot, diabetic foot ulcer, leg ulcer and diabetic neuropathy.

In a further aspect, the invention provides a method of treating wound healing, preferably chronic wound healing, diabetic foot, diabetic foot ulcer, leg ulcer, Raynaud's disease, male erectile dysfunction, female sexual dysfunction, diabetes, hair loss, skin aging, vascular aging, pulmonary artery hypertension; stable, unstable, and variant (Prinzmetal) angina; hypertension, pulmonary hypertension, chronic obstructive pulmonary disease, congestive heart failure, renal failure, atherosclerosis, conditions of reduced blood vessel patency, peripheral vascular disease, vascular disorders, systemic sclerosis (SSc), scleroderma, morphea, inflammatory diseases, stroke, bronchitis, chronic asthma, allergic asthma, allergic rhinitis, diabetic neuropathy, Idiopathic pulmonary fibrosis (IPF), peyronic's disease, glaucoma or a disease characterized by disorders of gut motility like irritable bowel syndrome, liver fibrosis, Alzheimer's disease and chronic heart failure, wherein preferably said disease is selected from wound healing, preferably chronic wound healing, diabetic foot, diabetic foot ulcer, leg ulcer, diabetic neuropathy, peripheral vascular disease, vascular disorders such as Raynaud's disease, systemic sclerosis (SSc), scleroderma, pulmonary artery hypertension, diabetes, male erectile dysfunction, and wherein again further preferably said disease is selected from wound healing, preferably chronic wound healing, diabetic foot, diabetic foot ulcer, leg ulcer and diabetic neuropathy in a human or in non-human mammal, preferably in a human, said method comprises administering to said human or said non-human mammal, preferably to said human, an effective amount of a compound of formula I.

In a very preferred embodiment of the present invention, said disease or said a medical condition is selected from wound healing, preferably chronic wound healing, diabetic foot, diabetic foot ulcer and leg ulcer.

Chronic, non-healing skin wounds such as in diabetes mellitus are governed by complex disease mechanisms including impaired angiogenesis, defective microcirculation, and endothelial dysfunction. Diabetic foot ulcer and chronic wounds are a major source of morbidity and is a leading cause of hospitalizations in diabetic patients. It afflicts 15% of diabetes patients (275 Mio) and is a huge burden to patients and payers (12 billion $/year). 3-4% of all diabetic patients will get lower limb amputations every year. Ultra-potent PDE5 inhibitors or compounds integrating highly potent inhibition of PDE5 and activation of nitric oxide dependent soluble guanylate cyclase as the ones of the present invention can be expected to accelerate wound healing.

As used herein, the terms "treatment", "treat", "treated" or "treating" refer to prophylaxis and/or therapy. In one embodiment, the terms "treatment", "treat", "treated" or "treating" refer to a therapeutic treatment. In another embodiment, the terms "treatment", "treat", "treated" or "treating" refer to a prophylactic treatment. Preferably, beneficial or desired clinical results of said treatment include, but are not limited to, alleviation of symptoms, diminishment of extent of disease or medical condition, stabilized (i.e., not worsening) state of disease or medical condition, delay or slowing of disease or medical condition progression, amelioration or palliation of the disease or medical condition state.

As used herein, the term "effective amount" refers to an amount necessary or sufficient to realize a desired biologic effect. Preferably, the term "effective amount" refers to an amount of a compound of formula I of the present invention that (i) treats or prevents the particular disease, medical condition, or disorder, (ii) attenuates, ameliorates, or eliminates one or more symptoms of the particular disease, medical condition, or disorder, or (iii) prevents or delays the onset of one or more symptoms of the particular disease, medical condition, or disorder described herein. An effective amount of the inventive compound of formula I, or said pharmaceutical composition, would be the amount that achieves this selected result, and such an amount could be determined as a matter of routine by a person skilled in the art. Further preferably, the term "effective amount", as used herein, refers to an amount necessary or sufficient to be effective to increase the inhibition of PDE5, typically and preferably as determined in Example 64, or to increase the formation of cGMP, typically and preferably as determined in Example 65. The effective amount can vary depending on the particular composition being administered and the size of the subject. One of ordinary skill in the art can empirically determine the effective amount of a particular composition of the present invention without necessitating undue experimentation.

The term "mammal", as used herein, includes, but is not limited to, humans, mice, rats, guinea pigs, monkeys, dogs, cats, horses, cows, pigs, and sheep. The term "mammal", as used herein, preferably refers to humans.

The compounds of formula I and the pharmaceutical compositions of the present invention may be administered by any suitable route, for example by oral, buccal, sublingual, rectal, vaginal, nasal, topical or parenteral administration, which forms another aspects of the present invention.

In again another aspect, the present invention provides for a compound of the formula II:

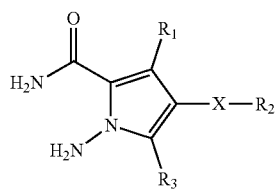

wherein $R_1$, $R_2$, $R_3$ are defined as for the compound of formula I.

In still a further aspect, the present invention provides for a compound of formula IV

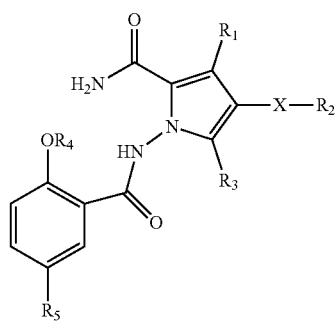

wherein X, $R_1$, $R_2$, $R_3$, $R_4$, $R_5$ are defined as for the compound of formula I.

In again another aspect, the present invention provides for a process for the preparation of a compound of formula I,

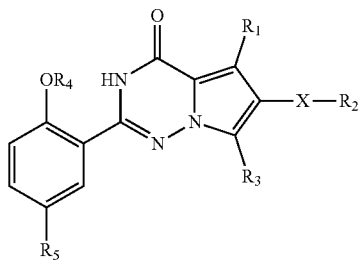

wherein said process comprises:
(a) reaction of a compound of formula II with a benzoic acid derivative of formula III in an aprotic or a protic solvent to generate a compound of formula IV

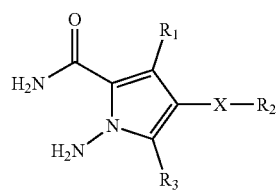

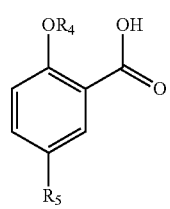

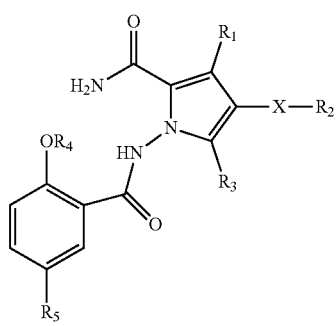

(b) cyclization of said compound of formula IV to yield compound of formula I, wherein X, $R_1$, $R_2$, $R_3$, $R_4$, and $R_5$ are defined as for the compound of formula I.

In again another aspect, the present invention provides for a process for the preparation of a compound of formula I, wherein said process comprises (a) reaction of a compound of formula VI with a benzoyl chloride derivative of formula VIA to generate a compound of formula VII

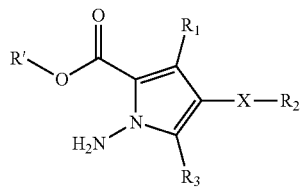

VI

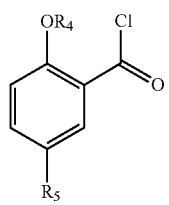

VIA

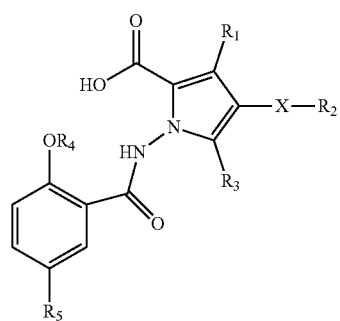

VII (b) hydrolysis of the ester compound of formula VII to an acid derivative of formula VIII

VIII (c) amination of said compound of formula VIII to yield a compound of formula IV

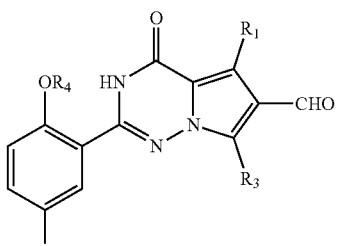

IV (d) cyclization of said compound of formula IV to yield compound of formula I, wherein X, $R_1$, $R_2$, $R_3$, $R_4$, and $R_5$ are defined as for the compound of formula I; and wherein R' is $C_1$-$C_4$ alkyl, benzyl, 4-alkoxybenzyl.

In again another aspect, the present invention provides for a process for the preparation of a compound of formula I, wherein said process comprises conversion of compound of formula IA to yield compound of formula I

IA wherein X, $R_1$, $R_2$, $R_3$, $R_4$, and $R_5$ are defined as for the compound of formula I in any one of the claims 1 to 8.

Compounds of formula I may be prepared by the following reaction SCHEME 1 and reaction SCHEME 2. These schemes represent the synthesis of generic compounds of formula I and forms part of the present invention.

SCHEME 1

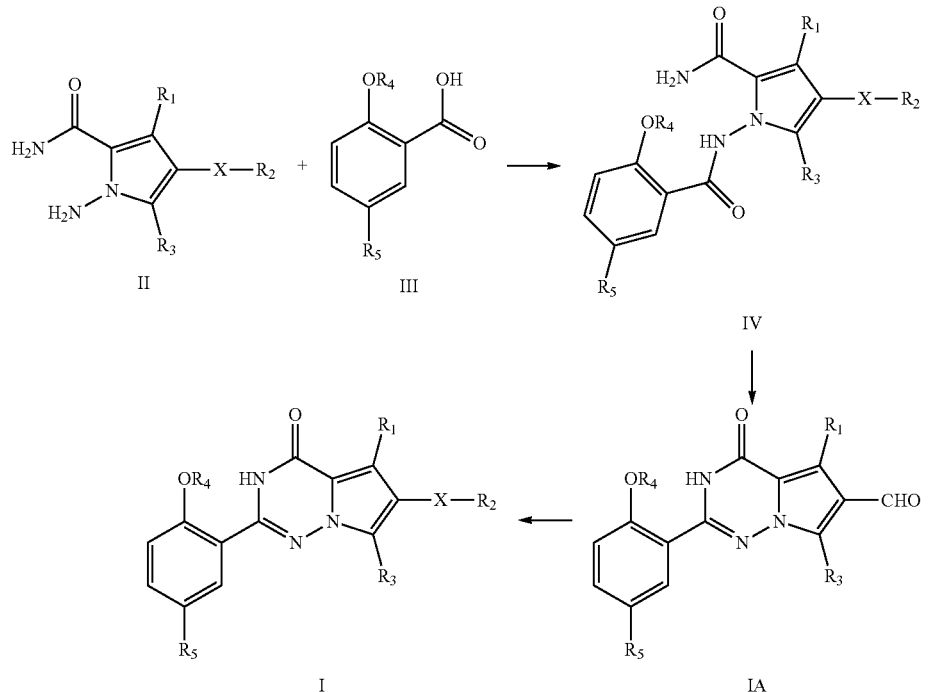

Thus, a process for preparing compounds of formula I involves synthesis of intermediate II which is a precursor to compound of formula IV which acts as a precursor to other compounds of formula I. Compound of formula IV is synthesized alternatively as shown in SCHEME 2, starting from compound of formula V, which is subsequently converted to compound of formula VI, followed by compound VII and VIII; SCHEME 2 thus forms an alternate route for the synthesis of the inventive compound of formula I.

Compound of formula II is reacted with a benzoic acid derivative of formula III in an aprotic or a protic solvent, selected from the group comprising DMF, acetonitrile, dialkylether, chlorinated hydrocarbons. The reaction is performed in the presence of a condensation reagent like e.g. thionyl chloride, phosphoroxy chloride, carbodiimide reagents like DCC, EDC or DCI, HBTU in presence or absence of bases to generate a compound of formula IV, which undergoes a reductive cyclization in the presence of bases like potassiumhydroxide, potassium tert-butoxide in solvents like butanol, poly-ethyleneglycol, DMF to generate compound of formula IA. Compound IA under various reaction conditions is converted to compounds of the type I.

SCHEME 2

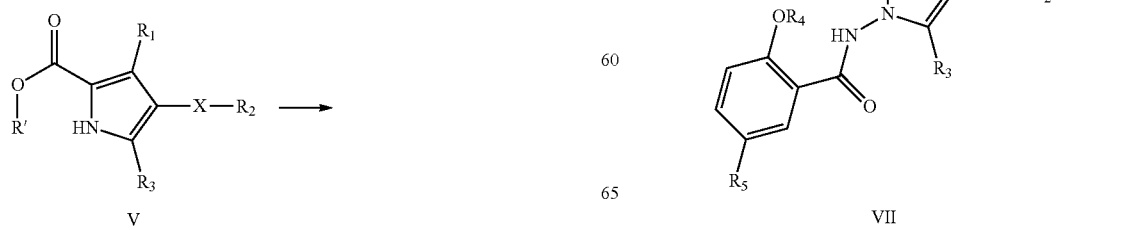

-continued

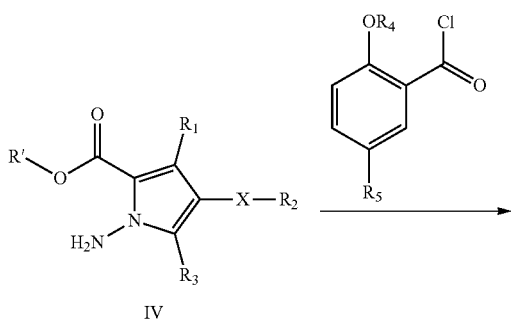

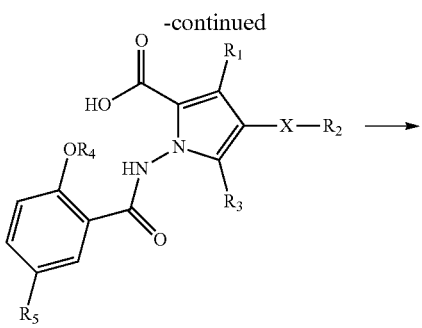

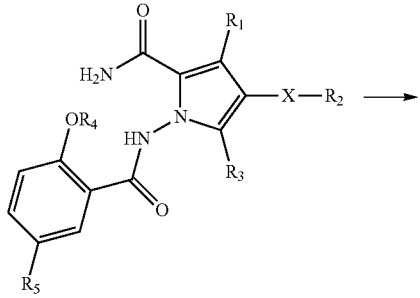

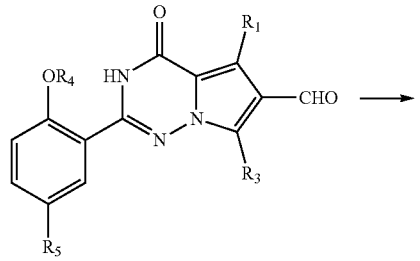

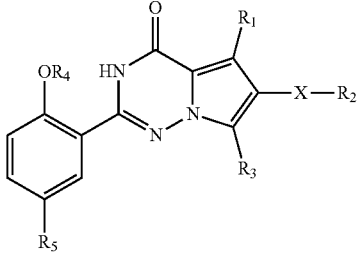

Wherein R' typically and preferably comprises: $C_1$-$C_4$ alkyl, benzyl, 4-alkoxybenzyl. The above alternate reaction sequence can be schematically represented as follows, wherein the substitutions R' is as defined above and $R_1$ is typically and preferably methyl, $R_2$ is typically and preferably formyl; $R_3$ is typically and preferably propyl, $R_4$ is typically and preferably propoxy, $R_5$ is typically and preferably hydrogen.

For the conversion of compound of formula V to VI, any amination reagent can be employed like $NH_4OH/NaOCl$ or the like. The reaction is performed in the presence of a base optionally under phase transfer conditions using phase transfer catalyst. The base that can be employed is NaOH, KOH, potassium tert-butoxide or the like. The phase transfer catalyst that can be employed for this purpose are benzyltrimethylammonium chloride, benzyltriethylammonium chloride, methyltricaprylammonium chloride, methyltributylammonium chloride, and methyltrioctylammonium chloride or the like. The reaction is performed in the presence of water and a another solvent which is typically and preferably selected from chlorinated hydrocarbon solvents like dichloromethane, 1,2 dichloroethane, ether solvents like diethyl ether, tertiary butyl ether or the like; The reaction is preferably performed at temperatures ranging from between −20 to 30° C.

The thus obtained aminated product of the formula VI is reacted with a suitable activated benzoic acid compounds, preferably benzoic acid chloride. The reaction is performed in the presence of suitable amines, tertiary amine like diisopropylethylamine being the most preferable. The reaction is carried out in the presence of aprotic cyclic hydrocarbon solvent or halo-hydrocarbons wherein toluene and methylene chloride being the most preferable. The reaction is typically and preferably performed in the temperatures ranging from −20 to 30° C. The ester moiety of the compound of VII is hydrolyzed in the presence of alkali hydroxides like NaOH, LiOH, KOH and the reaction can be performed in water, alcohols like ethanol, propanol n-butanol or the like, cyclic ethers like tetrahydrofuran.

Amination of compound of formula VIII can be carried out by any amination reagents, wherein any ammonium salt can be employed, $NH_4Cl$ or $NH_4OAc$ being the most preferable. The reaction is performed in the presence of a condensation reagent like thionyl chloride, phosphoroxy chloride, carbodiimide reagents like DCC, EDC or DCI, wherein HBTU being the most preferred. The solvents that can be employed are aprotic solvents like amides, ethers and hydrocarbons like dimethylformamide, tetrahydrofuran, methylenechloride. The reaction is typically and preferably performed at temperatures ranging from −20 to 30° C. The thus obtained compound IV is converted to I by cyclization to the triazine. The cyclization can be carried out in the presence of strong bases like potassium tert-butoxide. The reaction is preferably carried out in the presence of solvents like alcohols, wherein the preferred alcoholic solvent is tertiary butanol or PEG 400 or similar polyether solvents. The temperature of the reaction can range between 120-160° C.

Intermediate II of SCHEME 1, wherein $R_2$ is formyl is a preferred embodiment of the present invention.

Thus, for example, a specific process for preparing one of the compound falling under the group of compounds II, of formula 2a comprises treating ethyl-3-oxobutanoate with acetic acid/sodium nitrite to generate an oxime (Z)-ethyl-2-(hydroxyimino)-3-oxobutanoate (5a) by nitrosation of the active methylene group.

Compound 5a on condensation with (E)-hex-2-enal followed by cyclisation yield a pyrrole derivative, ethyl-4-formyl-1-hydroxy-3-methyl-5-propyl-1H-pyrrole-2-carboxylate (6a), which on Zinc/acetic acid reduction yield ethyl-4-formyl-3-methyl-5-propyl-1H-pyrrole-2-carboxylate (7a)

Carboxylate compound 7a was derivatized to the corresponding amide 8a which is subsequently converted to the intermediate 2a, 1-amino-4-formyl-3-methyl-5-propyl-1H-pyrrole-2-carboxamide.

SCHEME 3

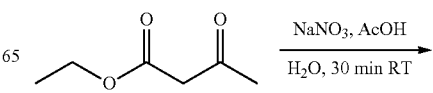

-continued

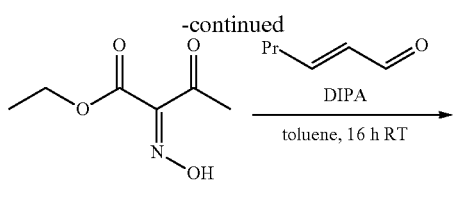
5a

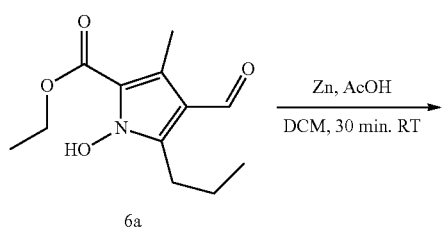
6a

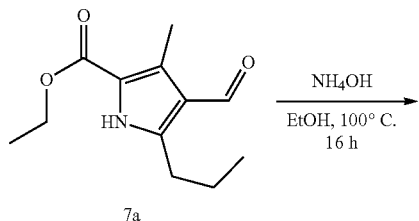
7a

+

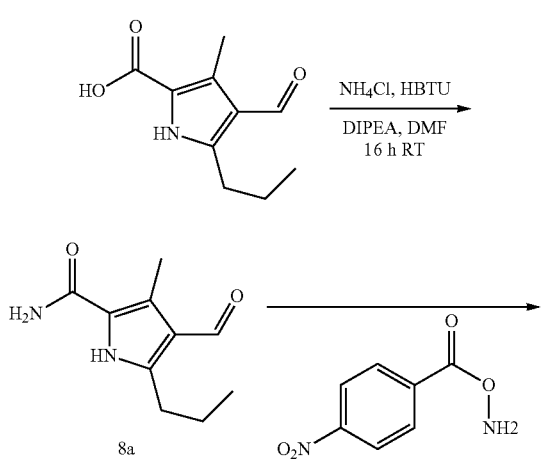
8a

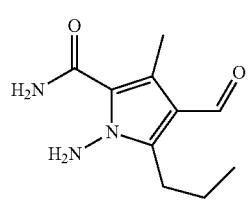
2a

Compounds of formula II are preferred intermediates for the synthesis of compounds of formula I.

Thus in accordance with the present invention, intermediate II, preferably when $R_2$=formyl, is subsequently reacted with benzoic acid derivative of the formula III

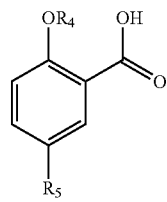
III wherein $R_4$ and $R_5$ are as defined above to generate

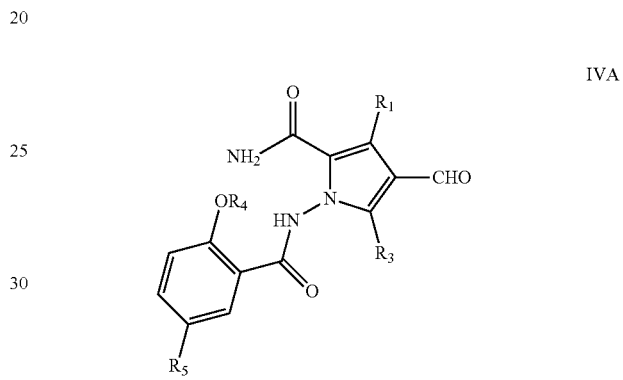
IVA which is cyclized to a pyrrolo triazine compound

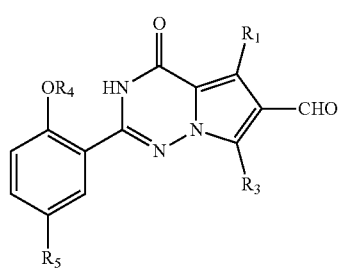
IA

Compound IA is subsequently converted to various compounds of formula I, like 1a, 1b, 1c, 1d, 1e, 1f, 1g by oxidation, reduction, condensation or the like.

As an example, compound IA, when $R_1$ is methyl, $R_2$ is CHO, $R_3$ is propyl, $R_4$ is ethoxy, $R_5$ is $SO_2NR_{10}R_{11}$, wherein $R_{10}R_{11}$ together form

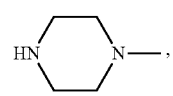

represents

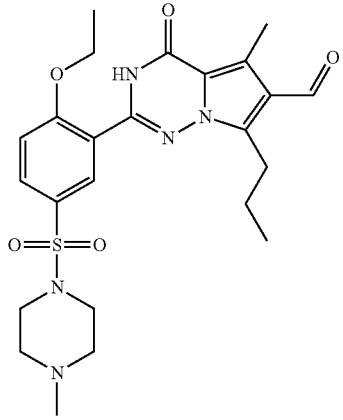

1j

Compound 1j is a novel compound and forms yet another part of the invention

Starting from compound 1j, under various reaction conditions, compounds 1a, 1b, 1c, 1d, 1e, 1f, 1g are prepared, as in SCHEME 3 and forms another part of the present invention.

Thus, compound 1j is oxidized in presence of suitable oxidizing agents like sodium chlorite, in the presence of solvents like acetonitrile, tetrahydrofurane or tert-butanol to generate compound of formula 1d. Compound 1d is converted to corresponding methyl ester 1f by treatment with methanol and thionyl chloride; 1d on the other hand is converted to an amide derivative 1e which is subsequently converted to a hydroxamic acid 1g.

Compound 1j is converted to an aldoxime of the type 1a which in turn generated a hydroxymethyl derivative 1b. Compound 1j is subsequently converted into a methylester of the type 1c.

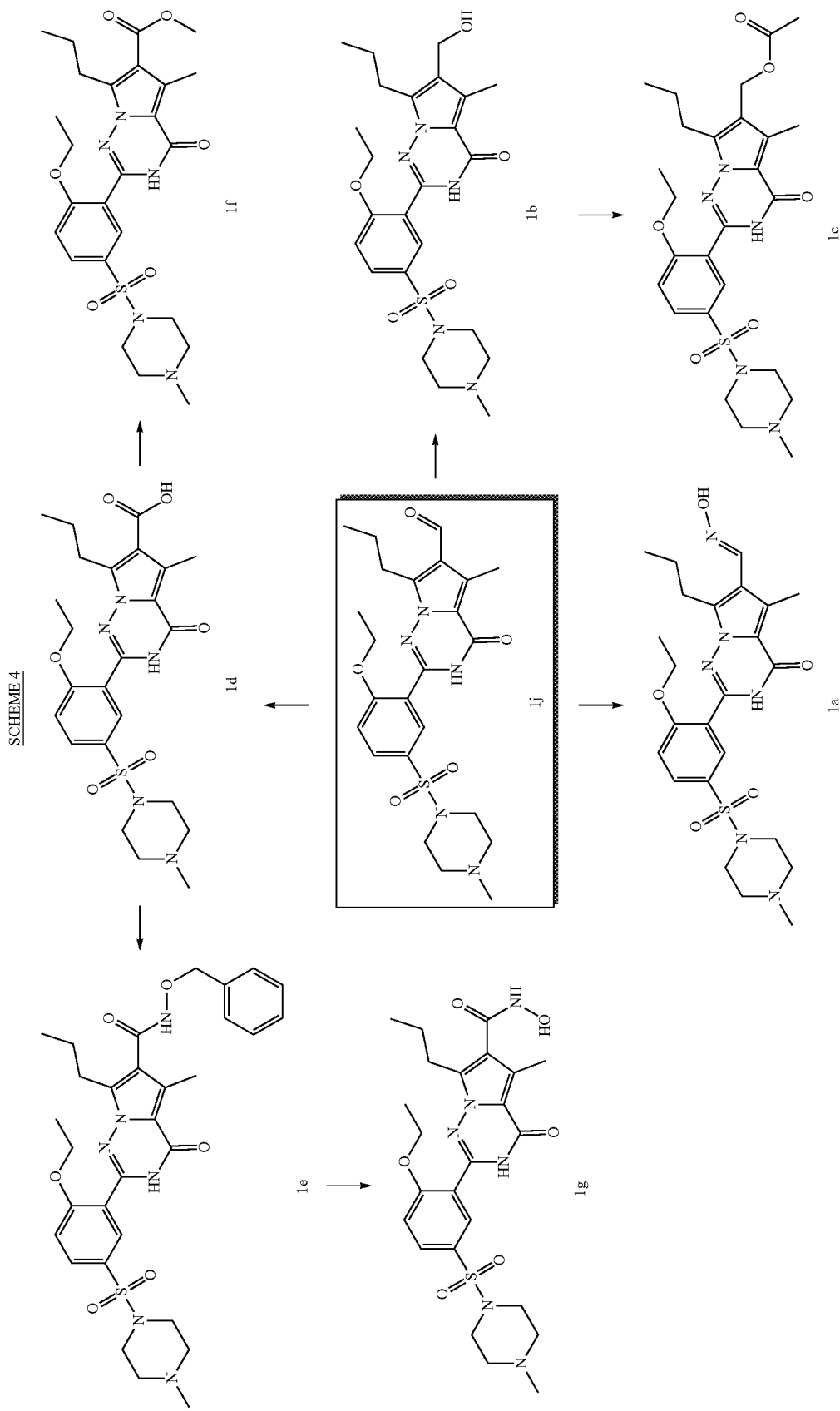
SCHEME 4

Likewise, compounds 1h and 1i are synthesized starting from 1j.

EXAMPLES

Synthesis of some of the compounds of formula I are exemplified below. The following examples further illustrate the present invention, but should not be construed in any way as to limit its scope.

Example 1

(Z)-ethyl 2-(hydroxyimino)-3-oxobutanoate (5a)

To a stirring solution of ethyl 3-oxobutanoate (500 mg, 3.84 mmol) in acetic acid (5 mL) was added sodium nitrate (330 mg, 4.50 mmol) in water (10 mL) and the resultant reaction mixture was stirred at RT for 16 h. The reaction mixture was quenched with saturated ammonium chloride solution and extracted with dichloromethane (2×20 mL). The combined dichloromethane layer was washed with brine and dried over anhydrous sodium sulfate and concentrated under reduced pressure to afford the title compound as a solid (750 mg). $^1$H NMR (300 MHz, CDCl$_3$) δ=9.09 (br s, 1H), 4.39 (q, J=7.2 Hz, 2H), 2.41 (s, 3H), 1.36 (t, J=7.3 Hz, 3H), Mass (M–H)=158.1.

Example 2

Ethyl 4-formyl-1-hydroxy-3-methyl-5-propyl-1H-pyrrole-2-carboxylate (6a)

(Z)-ethyl 2-(hydroxyimino)-3-oxobutanoate (5a) (10 g, 62.83 mmol), (E)-hex-2-enal (12.25 g, 125.7 mmol) in toluene, was added di-isopropylamine (1.26 g, 12.56 mmol) and the resultant reaction mixture was stirred at RT for 16 h. The reaction mixture was quenched with aqueous Ammonium chloride solution (100 mL) and extracted with dichloromethane (2×200 mL). The combined dichloromethane layer was washed with brine and dried over anhydrous sodium sulfate and concentrated under reduced pressure. Purification by column chromatography (100-200 mesh silica gel, 0-5% ethyl acetate in pet ether as eluent) afforded the title compound as a solid (10.5 g). $^1$H NMR (400 MHz, CDCl$_3$) δ=12.35 (d, J=1.4 Hz; 1H), 9.95 (d, J=1.4 Hz; 1H), 4.51-4.35 (m, 2H), 3.02-2.85 (m, 2H), 2.56 (d, J=1.4 Hz; 3H), 1.77-1.62 (m, 2H), 1.43 (dt, J=1.2, 7.1 Hz; 3H), 1.04-0.91 (m, 3H), Mass (M+H)=240.1.

Example 3

Ethyl 4-formyl-3-methyl-5-propyl-1H-pyrrole-2-carboxylate (7a)

To a stirring solution of ethyl 4-formyl-1-hydroxy-3-methyl-5-propyl-1H-pyrrole-2-carboxylate (6a) (18 g, 75.51 mmol) in dichloromethane (1.8 L), were added zinc dust (34 g, 527.1 mmol) and acetic acid (74 mL) and the resultant reaction mixture was stirred at RT for 30 min. The reaction mixture was quenched with saturated sodium bicarbonate solution and adjusted PH to 7 then extracted with dichloromethane (2×250 mL). The combined dichloromethane layer was washed with brine and dried over anhydrous sodium sulfate and concentrated under reduced pressure. Purification by column chromatography (100-200 mesh silica gel, 5% methanol in dichloromethane as eluent) afforded the title compound as a solid (8 g). [SM was recovered by eluting with 5% ethyl acetate in pet ether as eluent]. $^1$H NMR (300 MHz, CDCl$_3$) δ=10.01 (s, 1H), 9.04 (br s, 1H), 4.34 (q, J=7.4 Hz, 2H), 2.95-2.84 (m, 2H), 2.58 (s, 3H), 1.70 (qd, J=7.3, 14.9 Hz, 2H), 1.38 (t, J=7.0 Hz, 3H), 0.98 (t, J=7.3 Hz, 3H), LCMS (M+H)=224.1, purity=68%.

Example 4

4-formyl-3-methyl-5-propyl-1H-pyrrole-2-carboxamide (8a) and 4-formyl-3-methyl-5-propyl-1H-pyrrole-2-carboxylic acid (8b)

To a stirring solution of ethyl 4-formyl-3-methyl-5-propyl-1H-pyrrole-2-carboxylate (7a) (13 g, 58.2 mmol) in ethanol (30 mL), was added ammonium hydroxide (130 mL) and the resultant reaction mixture was heated to 100° C. for 16 h. The reaction mixture was concentrated under reduced pressure and the obtained crude compound was used in the next step reaction without further purification. MS indicates the presence of mixture of products (mixture of 8a and 8b).

Example 5

4-formyl-3-methyl-5-propyl-1H-pyrrole-2-carboxamide (8a)

The above mixture (8a+8b) in dimethylformamide (40 mL), was treated with HBTU (27.9 g, 73.84 mmol) and diisoproylamine (1.58 g, 123.08 mmol) and stirred for RT under nitrogen atmosphere. To this ammonium chloride (4.88 g, 92.22 mmol) was added and the resultant reaction mixture was stirred at RT for 16 h. The reaction mixture was diluted with ethyl acetate (300 mL) and washed with brine and dried over anhydrous sodium sulfate and concentrated under reduced pressure. Purification was done by ether washings (3×20 mL) to afford the title compound as a solid (9.2 g). $^1$H NMR (400 MHz, DMSO-d6) δ=11.61 (br s, 1H), 9.89 (s, 1H), 7.10 (br s, 2H), 2.80 (br t, J=7.4 Hz, 2H), 2.45 (s, 3H), 1.68-1.52 (m, 2H), 0.87 (br t, J=7.2 Hz, 3H), Mass (M–H)=193.3.

Example 6

1-amino-4-formyl-3-methyl-5-propyl-1H-pyrrole-2-carboxamide (2a)

To a stirring solution of 4-formyl-3-methyl-5-propyl-1H-pyrrole-2-carboxamide (8a) (3.0 g, 15.46 mmol) in NMP, was added potassium tert-butoxide (17 mL, 17.0 mmol, 1M) and stirred for 20° C. for 2 h. To this O-(4-nitrobenzoyl)-hydroxylamine (3.37 g, 18.55 mmol) in NMP was added slowly and the resultant reaction mixture was stirred at RT for 30 min. [Purple color reaction mixture indicates the formation of product]. The reaction mixture was diluted with water (50 mL) and extracted with ethyl acetate (3×70 mL). The combined ethyl acetate layer was washed with brine and dried over anhydrous sodium sulfate and concentrated under reduced pressure. Purification was done by ether washings (3×30 mL) to afford the title compound as a solid. $^1$H NMR (400 MHz, DMSO-d6) δ=11.61 (br s, 1H), 9.85 (s, 1H), 7.87 (br s, 1H), 7.43 (br s, 2H), 2.93-2.83 (m, 2H), 2.41 (s, 3H), 1.60-1.52 (m, 2H), 0.91 (br t, J=7.2 Hz, 3H), Mass (M+H)=210.3.

SCHEME 5

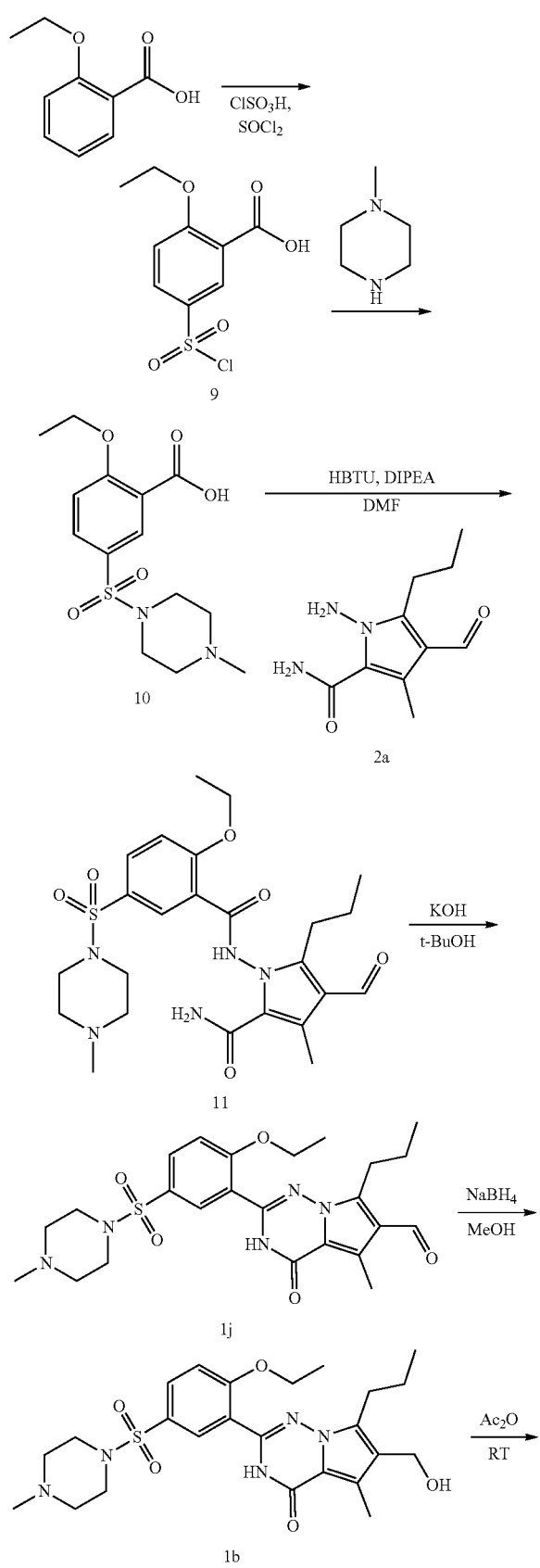

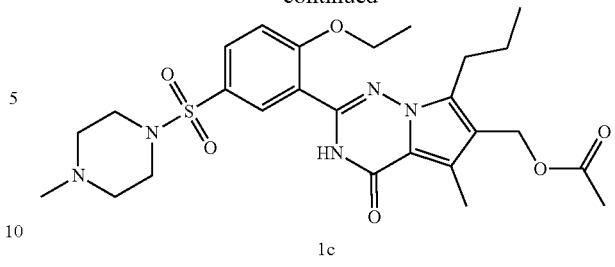

Example 7

5-(chlorosulfonyl)-2-ethoxybenzoic acid (9)

2-ethoxybenzoic acid (25 g) at 25° C. was added to a mixture of thionyl chloride (11 mL), and chlorosulfonic acid (41.3 mL) and the resultant reaction mixture was stirred at RT for 16 h. An off white solid was separated out which is stirred for 1 h. And the reaction mixture was quenched with ice (270 g) and water (60 mL). The obtained solid was separated by filtration and solid was washed with water (2×100 mL) and dried under vacuum to afford the title compound as a solid (30 g). $^1$H NMR (400 MHz, CDCl$_3$) δ=8.83 (s, 1H), 8.20 (br d, J=8.8 Hz, 1H), 7.23 (d, J=8.8 Hz, 1H), 4.45 (q, J=6.6 Hz, 2H), 1.64 (t, J=6.6 Hz, 3H), LCMS (M−H)=263.1, purity=95%.

Example 8

2-ethoxy-5-(4-methylpiperazin-1-ylsulfonyl)benzoic acid (10)

To a stirring solution of 5-(chlorosulfonyl)-2-ethoxybenzoic acid (9) (30 g) in water (124 mL) at 10° C., was added N-methyl piperazine (33.6 mL) at 15-20° C. The resultant reaction mixture was stirred at 10° C. After 5 min the title compound started to crystallize and the reaction mixture was stirred for 2 h. The solid was separated by filtration; the solid was washed with water and dried under vacuum. Purification was done by heating in acetone (100 mL) for 1 h. The suspension was cooled to RT, crystallized solid was separated by filtration and dried under vacuum to afford the title compound as a white solid (23 g). $^1$H NMR (400 MHz, DMSO-d6) δ=7.89 (br d, J=1.9 Hz, 1H), 7.81 (br dd, J=1.9, 8.8 Hz, 1H), 7.35 (br d, J=8.8 Hz, 1H), 4.21 (q, J=6.8 Hz, 2H), 2.87 (br s, 4H), 2.37 (br s, 4H), 2.14 (s, 3H), 1.36 (t, J=7.0 Hz, 3H), LCMS (M+H)=329.1, purity=88%.

Example 9

1-amino-N-(2-ethoxy-5-(4-methylpiperazin-1-ylsulfonyl)benzoyl)-4-formyl-3-methyl-5-propyl-1H-pyrrole-2-carboxamide (11)

To a stirring solution of 2-ethoxy-5-(4-methylpiperazin-1-ylsulfonyl)benzoic acid (10) (3.01g, 9.186 mmol) in DMF, was added HBTU (5.79 g, 15.3 mmol) and diisopropylethyl amine (2.46 g, 19.12 mmol) to this 1-amino-4-formyl-3-methyl-5-propyl-1H-pyrrole-2-carboxamide (2a) (1.6 g, 7.65 mmol) was added and the resultant reaction mixture was stirred at RT for 16 h. The reaction mixture was diluted with water and extracted with ethyl acetate (2×100 mL). The combined ethyl acetate layer was washed with brine, dried over anhydrous sodium sulfate and concentrated under reduced pressure. Purification by column chromatography (neutral alumina, 0.5% methanol in dichloromethane)

afforded the title compound as a solid (500 mg) [600 mg of amide (2a) was recovered]. $^1$H NMR (400 MHz, DMSO-d6) δ=11.42 (br s, 1H), 9.96 (s, 1H), 7.92-7.77 (m, 2H), 7.40 (br d, J=8.8 Hz, 2H), 7.32 (br s, 1H), 4.27 (q, J=6.8 Hz, 2H), 2.90 (br s, 4H), 2.78 (br s, 2H), 2.44-2.29 (m, 7H), 2.15 (s, 3H), 1.56 (br dd, J=7.4, 14.4 Hz, 2H), 1.40 (br t, J=6.7 Hz, 3H), 0.89 (br t, J=7.2 Hz, 3H), LCMS (M+H)=519.9.

Example 10

2-(2-ethoxy-5-(4-methylpiperazin-1-ylsulfonyl)phenyl)-5-methyl-4-oxo-7-propyl-3,4-dihydropyrrolo[1,2-f][1,2,4]triazine-6-carbaldehyde (1j)

To a stirring solution of 1-amino-N-(2-ethoxy-5-(4-methylpiperazin-1-ylsulfonyl)benzoyl)-4-formyl-3-methyl-5-propyl-1H-pyrrole-2-carboxamide (11) (1.5 g, 2.89 mmol) in t-butanol (30 vol), was added potassium hydroxide (2 g) and the resultant reaction mixture was heated to 100° C. for 2 days. The reaction mixture was cooled to RT and concentrated under reduced pressure, the obtained solid was purified by basic alumina by eluting with 0-0.5% methanol in dichloromethane to afford the title compound as a solid (500 mg) [SM was recovered by 2% methanol in dichloromethane]. $^1$H NMR (400 MHz, DMSO-d6) δ=11.78 (s, 1H), 10.12 (s, 1H), 7.94-7.76 (m, 2H), 7.39 (br d, J=9.3 Hz, 1H), 4.28-4.16 (m, 2H), 4.09 (q, J=5.1 Hz, 4H), 3.13-3.04 (m, 2H), 2.91 (br s, 4H), 2.68 (s, 3H), 2.41-2.27 (m, 4H), 2.09 (s, 3H), 1.65 (br dd, J=7.2, 14.7 Hz, 2H), 1.33 (br t, J=6.7 Hz, 3H), 0.89 (br t, J=7.2 Hz, 3H), Mass (M−H)=500.1.

Example 11

2-(2-ethoxy-5-((4-methylpiperazin-1-yl)sulfonyl)phenyl)-6-(hydroxymethyl)-5-methyl-7-propylpyrrolo[2,1-f][1,2,4]triazin-4(3H)-one (1b)

To a stirring solution of 2-(2-ethoxy-5-((4-methylpiperazin-1-yl)sulfonyl)phenyl)-5-methyl-4-oxo-7-propyl-3,4-dihydropyrrolo[2,1-f][1,2,4]triazine-6-carbaldehyde (1j) (400 mg, 0.798 mmol) in methanol, was added sodium borohydride (75 mg, 1.996 mmol) and the resultant reaction mixture was stirred at RT for 16 h. The reaction mixture was concentrated under reduced pressure and the obtained residue was diluted with dichloromethane (30 mL) and washed with brine, dried over anhydrous sodium sulfate and concentrated under reduced pressure. Purification by washings with ether (3×6 mL) afforded the title compound as a solid (320 mg). $^1$H NMR (400 MHz, DMSO-d6) δ=11.39 (br s, 1H), 7.84 (br d, J=8.8 Hz, 1H), 7.80 (d, J=1.9 Hz, 1H), 7.38 (br d, J=8.8 Hz, 1H), 4.66 (br t, J=5.1 Hz, 1H), 4.40 (s, 2H), 4.21 (q, J=6.8 Hz, 2H), 2.91 (br s, 4H), 2.79 (br t, J=7.4 Hz, 2H), 2.44 (s, 3H), 2.36 (br s, 4H), 2.14 (s, 3H), 1.70-1.49 (m, 2H), 1.33 (br t, J=7.0 Hz, 3H), 0.88 (t, J=7.2 Hz, 3H), LCMS (M+H)=504.1, purity=97.2%.

Example 12

(2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)methyl acetate (1c)

A solution of 2-(2-ethoxy-5-((4-methylpiperazin-1-yl)sulfonyl)phenyl)-6-(hydroxymethyl)-5-methyl-7-propylpyrrolo[2,1-f][1,2,4]triazin-4(3H)-one (1b) (100 mg, 0.198 mmol) in acetic anhydride (0.5 mL) was stirred at RT for 16 h. The reaction mixture was diluted with water (10 mL) and extracted with dichloromethane (3×15 mL). The combined dichloromethane layer was washed with water (5-6 times), dried over anhydrous sodium sulfate and concentrated under reduced pressure. Purification was done by washings with ether (2×2 mL) to afford the title compound as a solid (70 mg). $^1$H NMR (400 MHz, DMSO-d6) δ=11.52 (s, 1H), 7.94-7.72 (m, 2H), 7.39 (br d, J=8.8 Hz, 1H), 5.07 (s, 2H), 4.22 (q, J=6.5 Hz, 2H), 3.05-2.70 (m, 6H), 2.45 (s, 3H), 2.37 (br s, 3H), 2.15 (s, 3H), 2.01 (s, 3H), 1.70-1.53 (m, 2H), 1.34 (br t, J=6.7 Hz, 3H), 0.89 (br t, J=7.2 Hz, 3H), LCMS (M+H)=546.3, purity=99.5%.

SCHEME 6

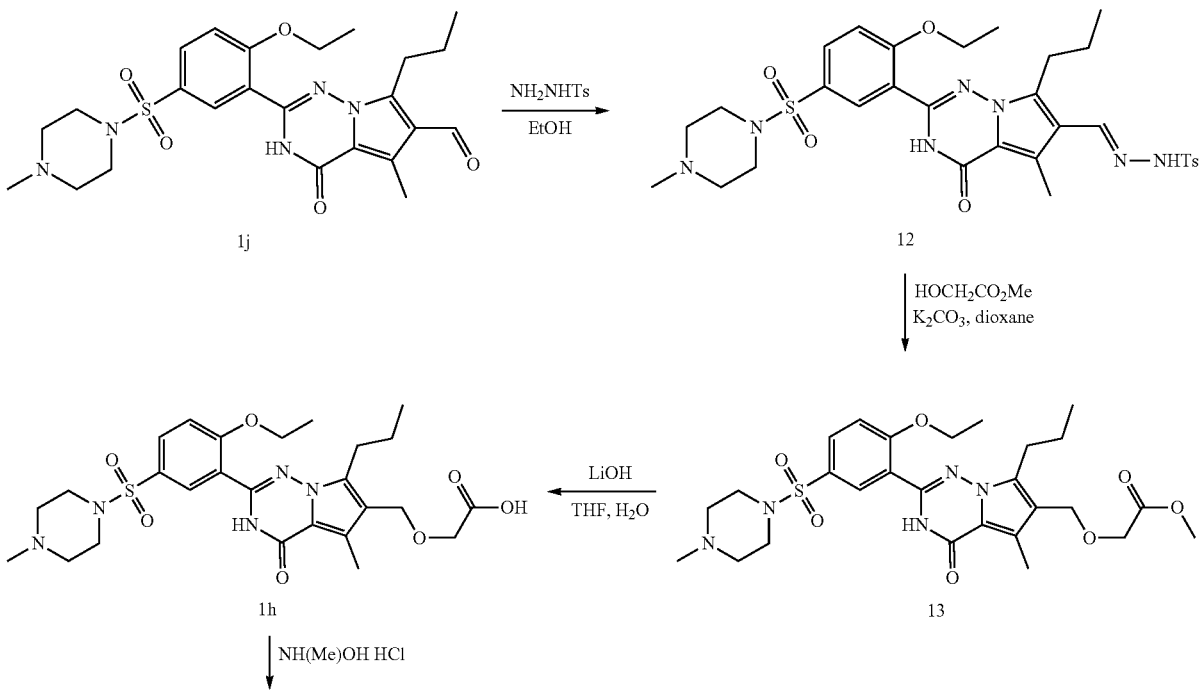

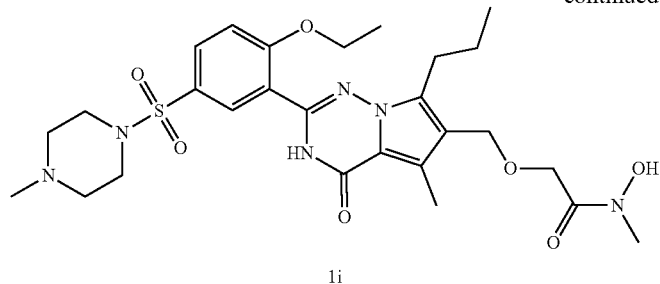

1i

Example 13

2-(2-ethoxy-5-((4-methylpiperazin-1-yl)sulfonyl)phenyl)-6-(hydroxymethyl)-5-methyl-7-propylpyrrolo[2,1-f][1,2,4]triazin-4(3H)-one (12)

To a stirring solution of 2-(2-ethoxy-5-((4-methylpiperazin-1-yl)sulfonyl)phenyl)-5-methyl-4-oxo-7-propyl-3,4-dihydropyrrolo[2,1-f][1,2,4]triazine-6-carbaldehyde (1j) (200 mg, 0.39 mol) in ethanol (5 mL), was added tosyl hydrazine (81.77 mg, 0.43 mmol) and the resultant reaction mixture was heated to 50° C. for 16 h. The reaction mixture was concentrated under reduced pressure to afford the title compound as an off white solid (250 mg). LC-MS (M+H)= 669.2, purity~94.3%.

Example 14 methyl 2-((2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)methoxy)acetate (13)

To a stirring solution of –2-(2-ethoxy-5-((4-methylpiperazin-1-yl)sulfonyl)phenyl)-6-(hydroxymethyl)-5-methyl-7-propylpyrrolo[2,1-f][1,2,4]triazin-4(3H)-one (12) (150 mg, 0.224 mmol) in dioxane (8 mL), were added potassium carbonate (108 mg, 0.784 mmol) and methylglycolate (81 mg, 0.448 mmol). The resulted mixture was heated in a microwave at 120° C. for 1 h. The reaction mixture was concentrated and the obtained crude was purified by prep TLC to afford the title compound as an off white solid (70 mg). $^1$H NMR (400 MHz, DMSO-d6) δ=11.44 (s, 1H), 7.91-7.76 (m, 2H), 7.38 (d, J=8.8 Hz, 1H), 4.51 (s, 2H), 4.21 (q, J=7.0 Hz, 2H), 4.13 (s, 2H), 3.68 (s, 3H), 2.91 (br s, 4H), 2.81 (br t, J=7.4 Hz, 2H), 2.44 (s, 3H), 2.40-2.27 (m, 4H), 2.15 (s, 3H), 1.61 (br dd, J=7.4, 14.9 Hz, 2H), 1.33 (t, J=6.7 Hz, 3H), 0.93-0.83 (m, 3H), Mass (M+H)=576.3.

Example 15

2-((2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)methoxy)acetic acid (1 h)

To a stirring solution of methyl 2-((2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)methoxy)acetate (13) (25 mg, 0.043 mmol) in 2:1 ratio of tetrahydrofuran and water (1+0.5 mL), was added lithium hydroxide (4.9 mg, 0.13 mmol) and the resultant reaction mixture was stirred at RT for 3 h. The reaction mixture was concentrated and the residue was neutralized with saturated citric acid and then extracted with dichloromethane (2×20 mL). The combined dichloromethane layer was washed with brine, dried over sodium sulfate and concentrated under reduced pressure. Purification was carried out by prep TLC to afford the title compound as a pale green solid (10 mg). $^1$H NMR (400 MHz, DMSO-d6) δ=11.37 (s, 2H), 7.97-7.71 (m, 2H), 7.38 (br d, J=8.8 Hz, 1H), 4.51 (br s, 2H), 4.21 (q, J=6.8 Hz, 2H), 3.62 (br s, 2H), 3.05-2.71 (m, 6H), 2.49-2.30 (m, 7H), 2.14 (s, 3H), 1.60 (br d, J=6.5 Hz, 2H), 1.33 (br t, J=6.7 Hz, 3H), 0.86 (br d, J=2.3 Hz, 3H), LCMS (M–H)= 560.3, purity=97.8%

Example 16

2-((2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)methoxy)-N-hydroxy-N-methylacetamide (1i)

To a stirring solution of 2-((2-(2-ethoxy-5-((4-methylpiperazin-1-yl)sulfonyl)phenyl)-5-methyl-4-oxo-7-propyl-3,4-dihydropyrrolo[2,1-f][1,2,4]triazin-6-yl)methoxy)acetic acid (1 h) (15 mg, 0.0267 mmol) in dimethylformamide (1 mL), was added HBTU (12 mg, 0.032 mmol) and DIPEA (6.9 mg, 0.05 mmol). The mixture was then added with hydroxylamine hydrochloride (2.7 mg, 0.032 mmol) and the reaction mixture was stirred at RT for 2 h. The reaction mixture was quenched with ice water (5 mL) and extracted with ethyl acetate (2×10 mL). The combined ethyl acetate layer was washed with brine, dried over sodium sulfate and concentrated under reduced pressure. Purification by prep TLC afforded the title compound as a pale brown solid (5 mg). $^1$H NMR (400 MHz, DMSO-d6) δ=11.45 (s, 1H), 9.75 (br s, 1H), 7.94-7.76 (m, 2H), 7.38 (d, J=8.8 Hz, 1H), 4.51 (s, 2H), 4.28-4.05 (m, 4H), 3.10 (s, 3H), 2.91 (br s, 4H), 2.85-2.78 (m, 2H), 2.44 (s, 3H), 2.36 (br s, 4H), 2.14 (s, 3H), 1.60 (br dd, J=7.4, 14.4 Hz, 2H), 1.33 (t, J=7.0 Hz, 3H), 0.87 (t, J=7.4 Hz, 3H), LCMS (M–H)=560.3, purity=98.2%.

SCHEME 7

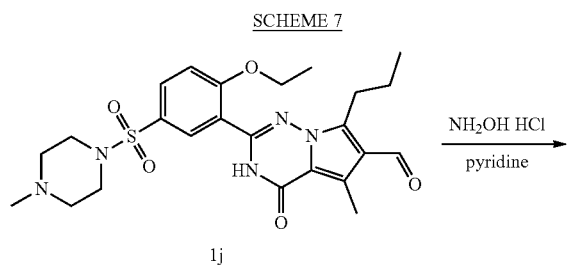

Example 17

(E)-2-(2-ethoxy-5-((4-methylpiperazin-1-yl)sulfonyl)phenyl)-5-methyl-4-oxo-7-propyl-3,4-dihydropyrrolo[2,1-f][1,2,4]triazine-6-carbaldehyde oxime (1a)

To a stirring solution of 2-(2-ethoxy-5-((4-methylpiperazin-1-yl)sulfonyl)phenyl)-5-methyl-4-oxo-7-propyl-3,4-dihydropyrrolo[2,1-f][1,2,4]triazine-6-carbaldehyde (1j) (20 mg, 0.039 mmol) in pyridine (0.3 mL) was added hydroxylamine hydrochloride (3.7 mg, 0.05 mmol) and the reaction mixture was heated to 80° C. for 4 h. Purification was done by prep TLC to afford the title compound as a white solid (10 mg). $^1$H NMR (400 MHz, DMSO-d6) δ=11.57 (s, 1H), 10.95 (s, 1H), 8.21 (s, 1H), 7.93-7.77 (m, 2H), 7.39 (br d, J=8.8 Hz, 1H), 4.31-4.15 (m, 2H), 3.08-2.79 (m, 6H), 2.55 (br s, 3H), 2.37 (br s, 4H), 2.14 (s, 3H), 1.67-1.51 (m, 2H), 1.34 (br t, J=6.7 Hz, 3H), 0.87 (br t, J=7.2 Hz, 3H) LCMS (M−H)=517.1, purity=96.8%.

SCHEME 8

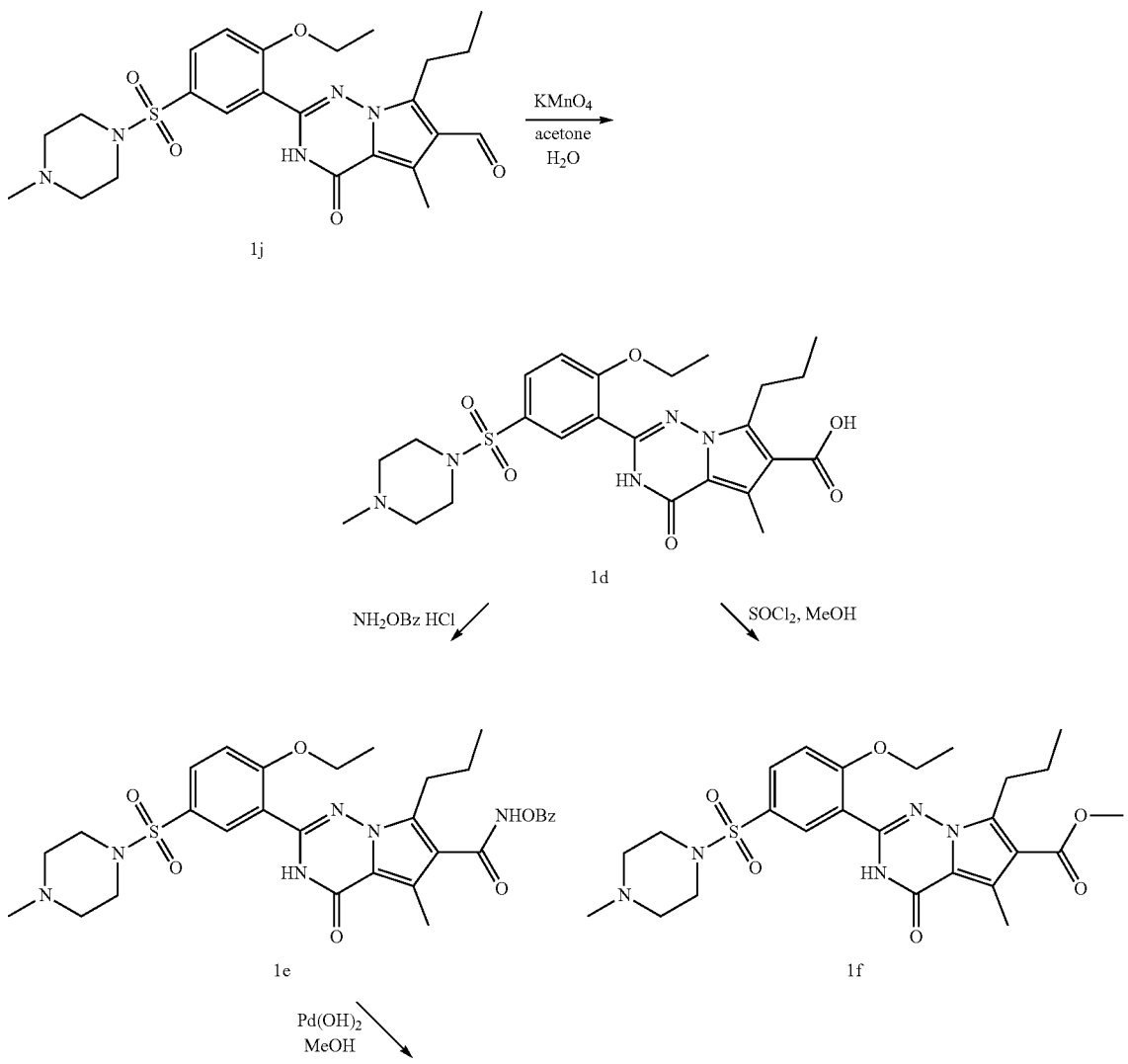

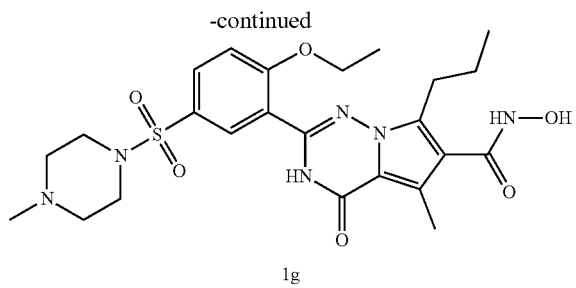

1g

Example 18

2-(2-ethoxy-5-((4-methylpiperazin-1-yl)sulfonyl)phenyl)-5-methyl-4-oxo-7-propyl-3,4-dihydropyrrolo[2,1-f][1,2,4]triazine-6-carboxylic acid (1d)

To a stirred suspension of 1j (200 mg) in acetone and water (1:1, 20 mL) was added a solution of KMnO₄ in acetone and water (1:1, 20 mL) over a period of 30 min, subsequently while addition the pH of the reaction mixture (pH-8) was adjusted to pH-5 by using a buffer solution (1N KH₂PO₄ and 1N HCl, pH-3.5). After completion of the addition the reaction mixture was stirred at RT for 2 h. On completion, the reaction mixture was quenched with 10% aq sodium bisulfate solution and the mixture was concentrated to remove acetone at RT. The obtained aqueous mixture was saturated with NaCl and filtered. The residual solid was stirred with 10% methanol in dichloromethane and filtered through celite. The filtrate was dried over anhydrous Na₂SO₄ and concentrated to afford compound 1d (120 mg) as white solid. ¹H NMR (400 MHz, DMSO-d6+one drop of TFA) δ=7.96-7.88 (m, 2H), 7.43 (d, J=9.4 Hz; 1H), 4.23 (q, J=7.0 Hz; 2H), 3.81 (br d, J=11.8 Hz; 2H), 3.49 (br d, J=11.8 Hz; 2H), 3.25-3.06 (m, 4H), 2.81 (s, 3H), 2.70-2.55 (m, 5H), 1.69-1.57 (m, 2H), 1.35 (t, J=6.9 Hz; 3H), 0.88 (t, J=7.3 Hz; 3H), LCMS (M+H)=518.1, purity=93.5%.

Example 19 methyl 2-(2-ethoxy-5-((4-methylpiperazin-1-yl)sulfonyl)phenyl)-5-methyl-4-oxo-7-propyl-3,4-dihydropyrrolo[2,1-f][1,2,4]triazine-6-carboxylate (1f)

To a stirred solution of compound 1d (80 mg) in methanol, thionyl chloride was added slowly at 0° C. and the reaction mixture was refluxed for 16 h. On completion, the reaction mixture was concentrated and purified by prep-HPLC to afford compound 1f (35 mg) as pale yellow solid. ¹H NMR (400 MHz, CDCl₃) δ=9.62 (s, 1H), 8.53 (d, J=2.4 Hz; 1H), 7.87 (dd, J=2.4, 8.9 Hz; 1H), 7.15 (d, J=8.9 Hz; 1H), 4.34 (q, J=7.1 Hz; 2H), 3.89 (s, 3H), 3.35-3.18 (m, 2H), 3.09 (br s, 3H), 2.76 (s, 2H), 2.50 (br s, 3H), 2.28 (s, 2H), 1.78-1.66 (m, 2H), 1.61 (t, J=7.0 Hz; 3H), 0.98 (t, J=7.4 Hz; 3H), LCMS (M+H)=532.1, purity=96.8%.

Example 20

N-(benzyloxy)-2-(2-ethoxy-5-((4-methylpiperazin-1-yl)sulfonyl)phenyl)-5-methyl-4-oxo-7-propyl-3,4-dihydropyrrolo[2,1-f][1,2,4]triazine-6-carboxamide (1e)

To a stirred solution of compound 1f (100 mg) in DMF, HBTU (110 mg, 0.288 mmol) was added followed by DIPEA (0.2 mL, 1.152 mmol) at RT and stirred for 15 min. To this solution O-benzyl hydroxylamine hydrochloride (1.1 mmol) was added and the reaction mixture was stirred at RT for 6 h. After completion, the reaction mixture was diluted with ice cold water and filtered. The obtained residue was washed with diethyl ether and dried to afford 1e (60 mg) as white solid. LCMS (M+H)=623.3, purity=95.1%.

Example 21

2-(2-ethoxy-5-((4-methylpiperazin-1-yl)sulfonyl)phenyl)-N-hydroxy-5-methyl-4-oxo-7-propyl-3,4-dihydropyrrolo[2,1-f][1,2,4]triazine-6-carboxamide (1g)

To a stirred solution of 1e (70 mg) in methanol (2 mL), Pd(OH)₂ (20% w/w) was added and the reaction mixture was hydrogenated under atmospheric pressure for 1 h. After completion the reaction mixture was filtered through celite and the filtrate was concentrated. The crude material was purified by prep-TLC to afford 1g (14 mg) as pale yellow solid (which develops colored spot on TLC after standing at refrigerator temperature). ¹H NMR (400 MHz, DMSO-d6) δ=11.61 (s, 1H), 10.55 (br s, 1H), 8.99 (d, J=1.9 Hz; 1H), 7.93-7.70 (mi, 2H), 7.39 (d, J=8.9 Hz; 1H), 4.21 (q, J=6.8 Hz; 2H), 3.38 (q, J=7.0 Hz; 2H), 2.99-2.80 (m, 3H), 2.48 (s, 2H), 2.40-2.30 (m, 2H), 2.15 (s, 1H), 1.60 (br dd, J=7.4, 15.2 Hz; 2H), 1.33 (t, J=6.9 Hz; 2H), 1.24 (br s, 1H), 1.09 (t, J=7.0 Hz; 2H), 0.85 (t, J=7.3 Hz; 2H), LCMS (M+H)=533.1, purity=95%.

SCHEME 9

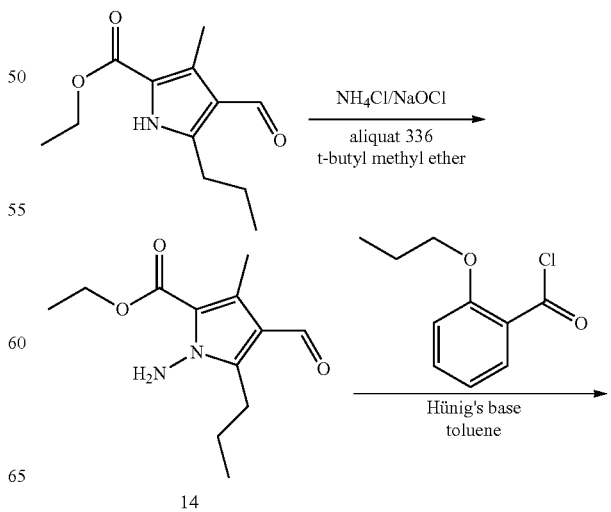

14

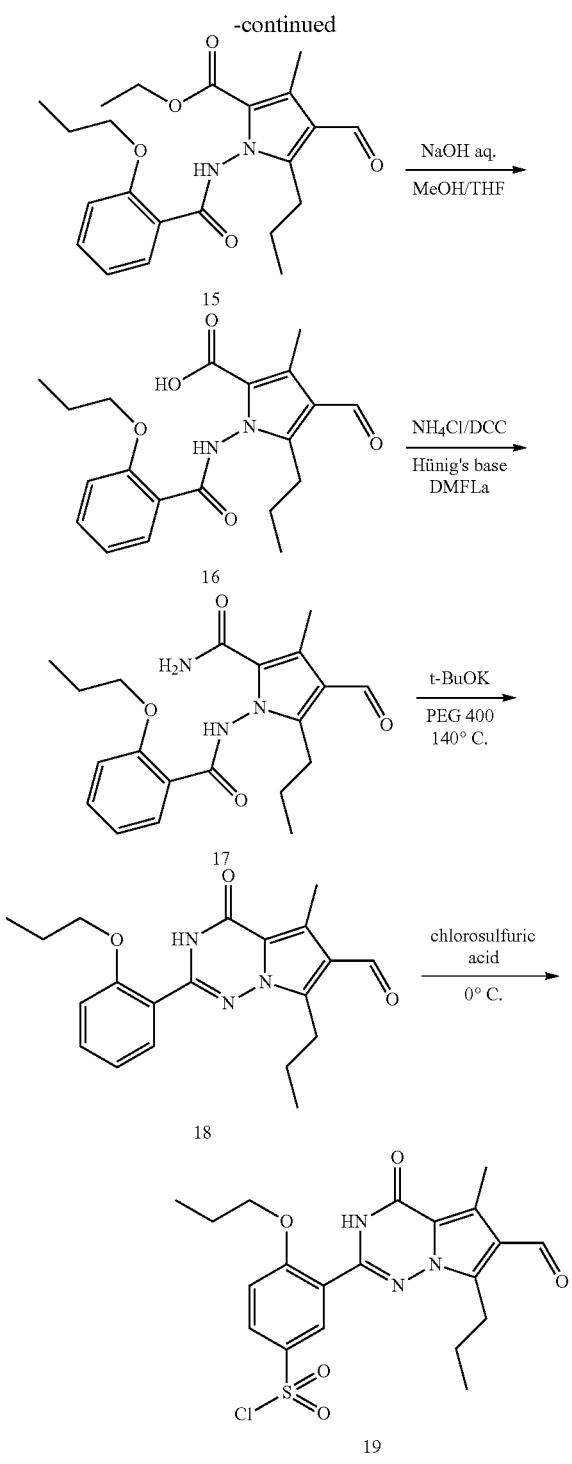

Example 22

Ethyl 1-amino-4-formyl-3-methyl-5-propyl-1H-pyrrole-2-carboxylate (14)

To a stirred solution of 190 mg (0.92 mmol) ethyl 4-formyl-3-methyl-5-propyl-1H-pyrrole-2-carboxylate in 5 mL tert-butyl methyl ether 25 mg aliquot 336, 290 mg (5.3 mmol) NH$_4$Cl, 2.5 mL 30% aqueous NaOH and 2.5 mL 9% aqueous NH$_4$Cl were added. During 20 min. 5.8 mL 9% NaOCl was added under vigorous stirring at room temperature. After 3 hours the reaction mixture was extracted using ethyl acetate and brine, dried with magnesium sulfate and the solvent removed under reduced pressure to afford 210 mg (quantitative) the title compound as a white solid. $^1$H NMR (300 MHz, DMSO-d6) δ=9.89 (s, 1H), 6.11 (s, 2H), 4.27 (q, J=7.2 Hz; 2H), 2.98-2.86 (m, 2H), 2.48 (s, 3H), 1.64-1.48 (m, 2H), 1.36-1.27 (m, 3H), 1.24 (br s, 1H), 0.90 (t, J=7.3 Hz; 3H). LCMS (M+H)=239.1, purity=94%.

Example 23

Ethyl 4-formyl-3-methyl-1-(2-propoxybenzamido)-5-propyl-1H-pyrrole-2-carboxylate (15)

A solution of 200 mg (1 mmol) 2-propoxybenzoyl chloride in 2 mL dimethylformamide were added at 10° C. to 160 mg (1 mmol) Hünig's base in 2 mL dimethyl formamide. A solution of 210 mg (0.92 mmol) ethyl 1-amino-4-formyl-3-methyl-5-propyl-1H-pyrrole-2-carboxylate (14) in 2 mL dimethylformamide was added and the reaction mixture was stirred at room temperature for 3 hours. The reaction mixture was extracted with ethyl acetate and washed with aqueous sodium carbonate, 0.5 N HCl and brine. The organic layer was dried with magnesium sulfate and the solvent removed under reduced pressure to give the crude product as a gum. Chromatography om silica using cyclohexane/ethyl acetate 3/1 afforded 290 mg (79%) of the title compound as a white solid. $^1$H NMR (500 MHz, CDCl$_3$) δ=10.19 (s, 1H), 8.26 (dd, J=2, 7 Hz; 1H), 7.54 (dd, J=8, 7 Hz; 1H), 7.13 (t, J=7 Hz; 1H), 7.07 (d, J=8 Hz, 1H), 4.17 (t, J=7 Hz, 2H), 4.16 (t, J=7 Hz, 2H), 2.79 (s, 3H), 3.18 (m, 2H), 1.81-1.74 (m, 4H), 1.15 (t, J=7 Hz, 3H), 1.00 (t, J=7 Hz, 4H). LCMS (M+H)=401.2, purity=92%.

Example 24

4-formyl-3-methyl-1-(2-propoxybenzamido)-5-propyl-1H-pyrrole-2-carboxylic acid (16)

To a solution of 400 mg (1 mmol) ethyl 4-formyl-3-methyl-1-(2-propoxybenzamido)-5-propyl-1H-pyrrole-2-carboxylate (15) in 1.5 mL water, 1.5 mL methanol and 1.5 mL tetrahydrofuran was added 1.5 mL 1 M sodium hydroxide aqueous solution. The reaction mixture was stirred at 50° C. for 5 hours. Extraction with ethyl acetate, washed with brine, dried with magnesium sulfate afforded after removal of solvent 370 mg (quantitative) the title compound as a white solid. LCMS (M+H)=373.2, purity=96%.

Example 25

4-formyl-3-methyl-1-(2-propoxybenzamido)-5-propyl-1H-pyrrole-2-carboxamide (17)

A solution of 420 mg (1.2 mmol) 4-formyl-3-methyl-1-(2-propoxybenzamido)-5-propyl-1H-pyrrole-2-carboxylic acid (16), 96 mg (1.84 mmol) ammonium chloride, 224 mg (1.46 mmol) HBOT, 640 uL (3.7 mmol) N,N-diisopropylethylamin (Hünig's base) in 16 mL dimethyl-formamide was treated with 2% mg (1.44 mmol) N,N'-dicyclohexylcarbodiimide (DCC). The reaction mixture was stirred for 5 hrs. at 50° C. Work up with ethyl acetate, brine wash and drying of the organic phase with magnesium sulfate afforded 427 mg (96%) title compound as a white solid. LCMS (M+H)=372.2, purity=93%.

Example 26

5-methyl-4-oxo-2-(2-propoxyphenyl)-7-propyl-3,4-dihydropyrrolo[2,1-f] [1,2,4]triazine-6-carbaldehyde (18)

600 mg (1.6 mmol) 4-formyl-3-methyl-1-(2-propoxybenzamido)-5-propyl-1H-pyrrole-2-carboxamide (17) were dissolved in 60 mol polyethylene glycol (PEG 400). The solution was dried for 30 minutes at 90° C. and 8 mbar. 562 mg (5 mmol) potassium tert-butoxide were added and the reaction mixture was heated at 8 mbar for 1 hour at 140° C. Dilution with water and extraction with ethyl acetate afforded the crude product as a white solid. Chromatography on silica using ethyl acetate/cyclohexane 7/3 afforded 490 mg (87%) title compound as a white solid. $^1$H NMR (500 MHz, CDCl$_3$) δ=10.18 (s, 1H), 10.09 (s, 1H), 8.19 (dd, J=2, 7 Hz; 1H), 7.50 (dd, J=8, 7 Hz; 1H), 7.13 (t, J=7 Hz; 1H), 7.06 (d, J=8 Hz, 1H), 4.16 (t, J=7 Hz, 2H), 3.23 (t, J=7 Hz, 2H), 2.79 (s, 3H), 2.04-1.95 (m, 2H), 1.81-1.74 (m, 2H), 1.15 (t, J=7 Hz, 3H), 1.00 (t, J=7 Hz, 4H). LCMS (M+H)=354.2, purity=97%.

Example 27

3-(6-formyl-5-methyl-4-oxo-7-propyl-3,4-dihydropyrrolo[2,1-f][1,2,4] triazin-2-yl)-4-propoxybenzene-1-sulfonyl chloride (19)

44 mg (0.12 mmol) 5-methyl-4-oxo-2-(2-propoxyphenyl)-7-propyl-3,4-dihydropyrrolo[2,1-f][1,2,4] triazine-6-carbaldehyde (18) was treated at 0° C. with 250 uL (3.8 mmol) chlorosulfuric acid. After 2 hours at 0° C. the starting material was completely dissolved resulting in a deep red solution. The reaction mixture was quenched with ice and water and extracted with 20 mL methylene chloride. This extract was directly used for the conversion to the sulfonamide.

Example 28

2-(5-((4-(2-hydroxyethyl)piperidin-1-yl)sulfonyl)-2-propoxyphenyl)-5-methyl-4-oxo-7-propyl-3,4-dihydropyrrolo[2,1-f][1,2,4]triazine-6-carbaldehyde (1p)

A solution of 0.12 mmol 3-(6-formyl-5-methyl-4-oxo-7-propyl-3,4-dihydropyrrolo[2,1-f][1,2,4]triazin-2-yl)-4-propoxybenzene-1-sulfonyl chloride (19) in 20 mL methylene chloride was treated at room temperature with a solution of 32 mg (0.25 mmol) 2-(piperidin-4-yl)ethanol and 64 mg (0.63 mmol) trimethylamine in 2 mL methylene chloride. After two hours at room temperature the reaction mixture was washed with diluted hydrochloric acid, dried with magnesium sulfate and concentrated. Chromatography on silica using cyclohexane/ethyl acetate 1/1 resulted in 61 mg (90%) title compound as a white solid. $^1$H NMR (500 MHz, CDCl$_3$) δ=10.18 (s, 1H), 9.89 (s, 1H), 8.50 (d, J=3 Hz, 1H), 7.86 (dd, J=3, 9 Hz, 1H), 7.16 (d, J=9 Hz, 1H), 4.24 (t, J=7 Hz, 2H), 3.79 (d, J=12 Hz, 1H), 3.65 (t, J=7 Hz, 2H), 3.21 (t, J=8 Hz, 2H), 2.78 (s, 3H), 2.32 (t, J=10 Hz, 2H), 1.80-1.15 (m, 11H), 1.16 (t, J=8 Hz, 3H), 0.99 (t, J=8 Hz, 3H). LCMS (M+H)=545.2, purity=98%.

SCHEME 10

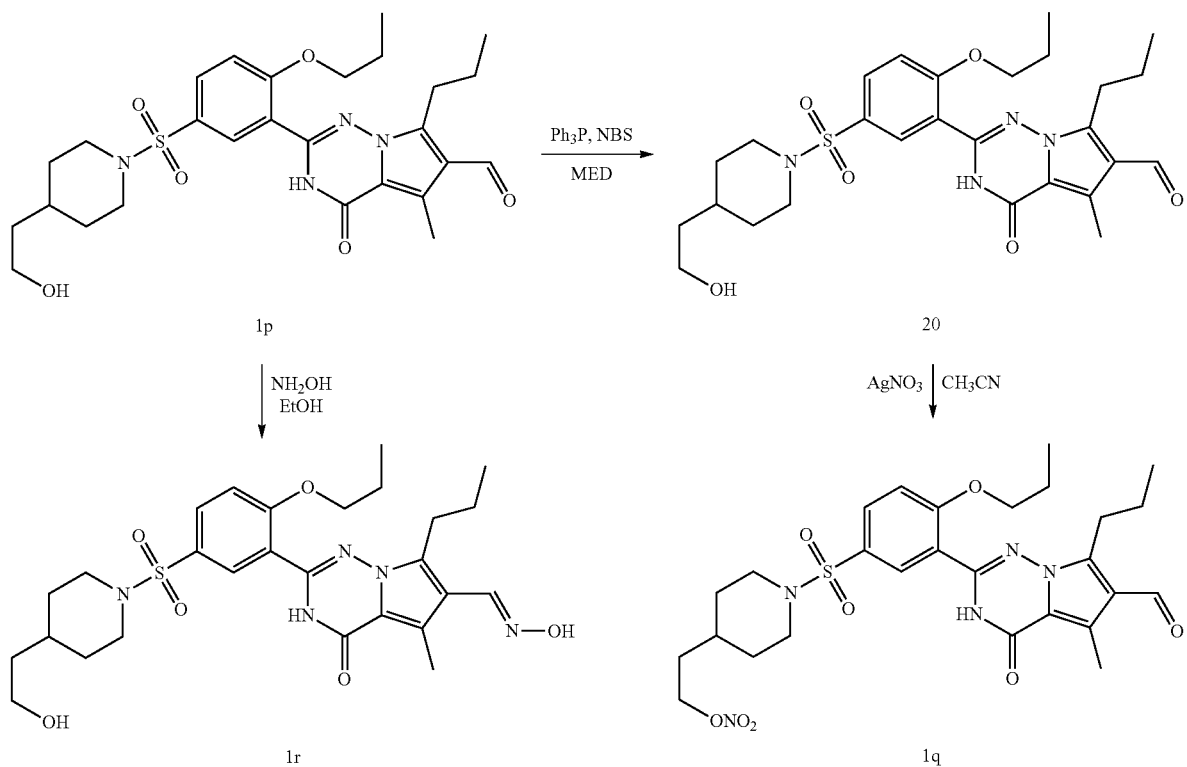

Example 29

2-(1-((3-(6-formyl-5-methyl-4-oxo-7-propyl-3,4-dihydro pyrrolo[2,1-f] [1,2,4]triazin-2-yl)-4-propoxyphenyl) sulfonyl) piperidin-4-yl)ethylnitrate (1q)

68 mg (0.125 mmol) 2-(5-((4-(2-hydroxyethyl)piperidin-1-yl)sulfonyl)-2-propoxyphenyl)-5-methyl-4-oxo-7-propyl-3,4-dihydropyrrolo[2,1-f][1,2,4] triazine-6-carbaldehyde (1p) in 20 mL methylene chloride was treated with 180 mg (0.69 mmol) triphenylphosphine and 125 mg (0.69 mmol) N-bromosuccinimide at room temperature. The reaction mixture was refluxed for 8 hours, after which TLC showed complete conversation to 2-(5-((4-(2-bromoethyl)piperidin-1-yl)sulfonyl)-2-propoxyphenyl)-5-methyl-4-oxo-7-propyl-3,4-dihydropyrrolo[2,1-f][1,2,4]-triazine-6-carbaldehyde (2o). Work-up with methylene chloride, washed with brine, dried with magnesium sulfate and removal of solvent under reduced pressure gave a colorless gum, which was dissolved in 10 mL acetonitrile. 190 mg (1.1 mmol) silver nitrate in 5 mL acetonitrile was added at room temperature. The reaction mixture was stirred for 3 days, worked up with ethyl acetate ad brine washed. The organic phase was dried with magnesium sulfate and the solvent removed under reduced pressure. Chromatography on silica using ethyl acetate/cyclohexane 2/3 gave 45 mg (61%) title compound as a white solid. $^1$H NMR (500 MHz, CDCl$_3$) δ=10.15 (s, 1H), 10.09 (s, 1H), 8.50 (d, J=2 Hz, 1H), 7.85 (dd, J=2, 9 Hz, 1H), 7.16 (d, J=9 Hz, 1H), 4.47 (t, J=7 Hz, 2H), 4.22 (t, J=7 Hz, 2H), 3.83 (d, J=11 Hz, 2H), 3.66 (m, 2H), 3.04 (t, J=8 Hz, 2H), 2.79 (s, 3H), 2.35-1.30 (m, 12H), 1.16 (t, J=7 Hz, 3H), 0.98 (t, J=7 Hz, 3H). LCMS (M+H)=590.2, purity=96%.

Example 30

(E)-2-(5-((4-(2-hydroxyethyl)piperidin-1-yl)sulfonyl)-2-propoxyphenyl-5-methyl-4-oxo-7-propyl-3,4-dihydropyrrolo[2,1-][1,2,4]triazine-6-carbaldehyde oxime (1r)

A solution of 40 mg 1p (0.07 mmol) in 10 mL ethanol was treated with 50% aqueous hydroxylamine. After 4 hours at room temperature the reaction mixture was extracted with ethyl acetate, washed with brine, dried with magnesium sulfate and the solvent removed under reduced pressure. Chromatography on silica using cyclohexane/ethyl acetate 1/1 resulted in 35 mg (85%) title compound as a white solid.

$^1$H NMR (500 MHz, CDCl$_3$) δ=9.98 (s, 1H), 8.42 (d, J=2 Hz, 1H), 8.26 (s, 1H), 7.82 (dd, J=2, 9 Hz, 1H), 7.12 (d, J=9 Hz, 1H), 4.19 (t, J=7 Hz, 2H), 3.77 (d, J=11 Hz, 2H), 3.65 (t, J=7 Hz, 2H), 3.00 (t, J=8 Hz, 2H), 2.57 (s, 3H), 2.31 (t, J=11 Hz, 2H), 2.10-1.30 (m, 11H), 1.23 (t, J=7 Hz, 3H), 0.95 (t, J=8 Hz, 3H). LCMS (M+H)=560.3, purity=98%.

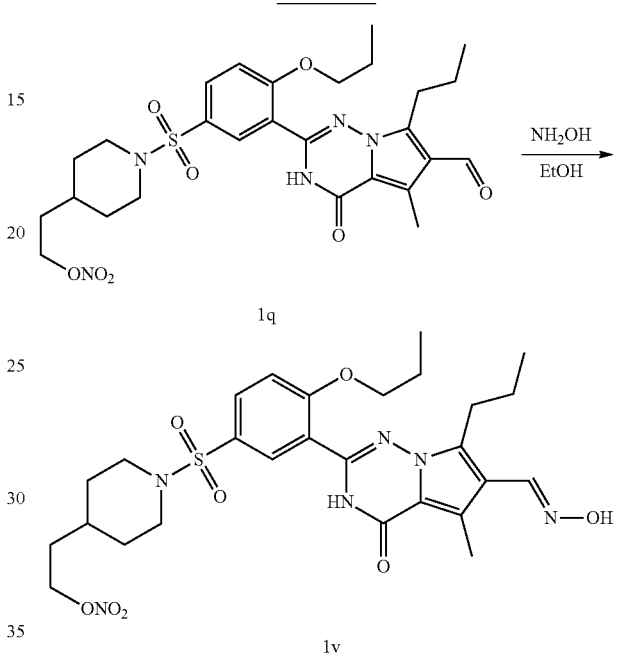

SCHEME 11

Example 31

(E)-2-(1-((3-(6-((hydroxyimino)methyl)-5-methyl-4-oxo-7-propyl-3,4-dihydropyrrolo[2,1-f][1,2,4]triazin-2-yl)-4-propoxyphenyl) sulfonyl) piperidin-4-yl)ethyl nitrate (1v)

25 mg (0.04 mmol) 2-(1-((3-(6-formyl-5-methyl-4-oxo-7-propyl-3,4-dihydropyrrolo[2,1-f][1,2,4]triazin-2-yl)-4-propoxyphenyl)sulfonyl)piperidin-4-yl)ethyl nitrate (1q) was dissolved in 20 mL ethanol. 0.5 mL 50% aqueous hydroxylamine was added at room temperature. After 3 hours at room temperature the reaction mixture was taken up in ethyl acetate and brine washed, dried over magnesium sulfate. The solvent was removed to give 22 mg (86%) title compound.

$^1$H NMR (500 MHz, CDCl$_3$) δ=9.83 (s, 1H), 8.50 (d, J=2 Hz, 1H), 8.29 (s, 1H), 7.85 (dd, J=2, 9 Hz, 1H), 7.16 (d, J=9 Hz, 1H), 4.47 (t, J=7 Hz, 2H), 4.22 (t, J=7 Hz, 2H), 3.83 (d, J=11 Hz, 2H), 3.66 (m, 2H), 3.04 (t, J=8 Hz, 2H), 2.35-1.30 (m, 11H), 1.16 (t, J=7 Hz, 3H), 0.98 (t, J=7 Hz, 3H). LCMS (M+H)=605.2, purity=92%.

SCHEME 12

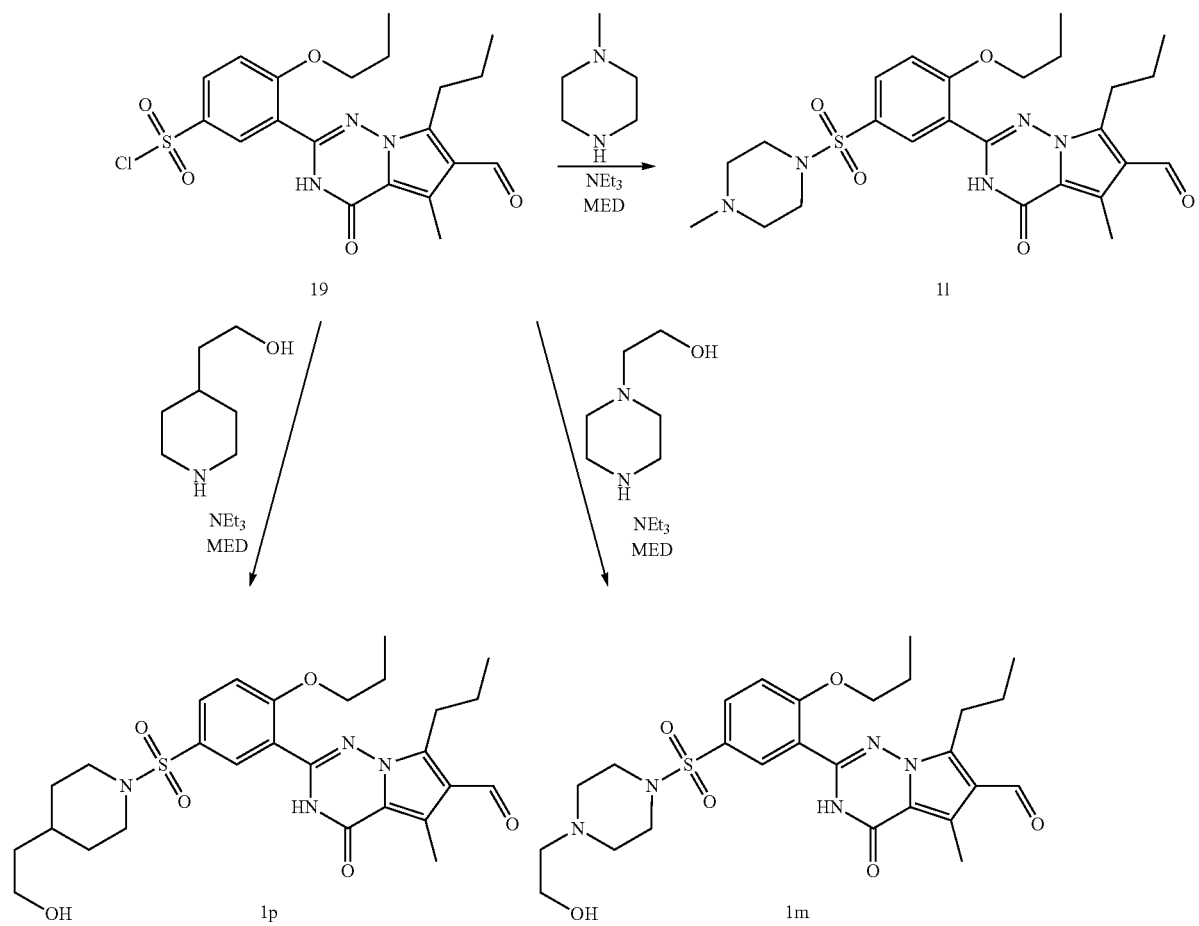

Example 32

5-methyl-2-(5-((4-methylpiperazin-1-yl)sulfonyl)-2-propoxyphenyl)-4-oxo-7-propyl-3,4-dihydropyrrolo[2,1-f][1,2,4]triazine-6-carbaldehyde (1l)

Following the procedure for 1p starting from 40 mg (0.11 mmol) 5-methyl-4-oxo-2-(2-propoxyphenyl)-7-propyl-3,4-dihydropyrrolo[2,1-f][1,2,4]triazine-6-carbaldehyde (19) and using 87 mg (0.75 mmol) 1-methylpiperazine gave after chromatography on silica using ethyl acetate/methanol (98/2) 46 mg (79%) title compound as a white solid. $^1$H NMR (500 MHz, CDCl$_3$) δ=9.68 (s, 1H), 8.51 (d, J=2 Hz, 1H), 7.83 (dd, J=2, 9 Hz, 1H), 7.16 (d, J=9 Hz, 1H), 4.65 (s, 2H), 4.23 (t, J=7 Hz, 2H), 3.64 (s, 2H), 3.20-2.58 (m, 8H), 3.14 (s, 3H), 2.95 (t, J=8 Hz, 2H), 2.58 (s, 3H), 2.00 (m, 2H), 1.72 (m, 2H), 1.16 (t, J=7 Hz, 3H), 0.97 (t, J=7 Hz, 3H). LCMS (M+H)=516.2, purity=96%.

Example 33

2-(5-((4-(2-hydroxyethyl)piperazin-1-yl)sulfonyl)-2-propoxyphenyl)-5-methyl-4-oxo-7-propyl-3,4-dihydropyrrolo[2,1-f][1,2,4]triazine-6-carbaldehyde (1m)

Following the procedure for 1p starting from 275 mg (0.78 mmol) 5-methyl-4-oxo-2-(2-propoxyphenyl)-7-propyl-3,4-dihydropyrrolo[2,1-f][1,2,4]triazine-6-carbaldehyde (18) and using 0.5 mL (4.0 mmol) 2-(piperazin-1-yl)ethanol gave after chromatography on silica using ethyl acetate/cyclohexane/methanol (40/60/3) 383 mg (90%) title compound as a colorless gum. $^1$H NMR (400 MHz, CDCl$_3$) δ=10.19 (s, 1H), 9.68 (s, 1H), 8.52 (d, J=2 Hz, 1H), 7.89 (dd, J=2, 9 Hz, 1H), 7.18 (d, J=9 Hz, 1H), 4.39-4.34 (m, 2H), 3.59 (m, 2H), 3.23 (t, J=7 Hz, 2H), 3.12 (brs, 4H), 2.79 (s, 3H), 2.64-2.58 (m, 6H), 1.79-1.72 (m, 4H), 1.62 (t, J=7 Hz, 3H), 0.99 (t, J=7 Hz, 3H). LCMS (M+H)=546.2, purity=93%.

SCHEME 13

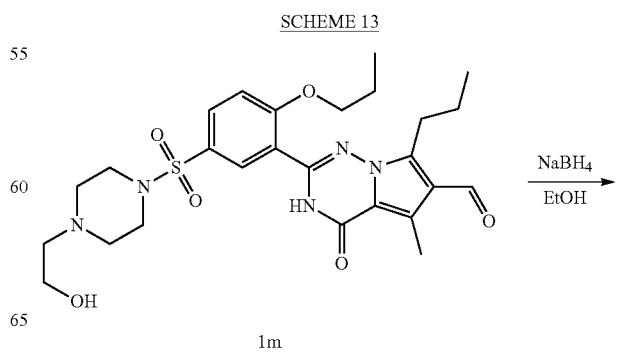

-continued

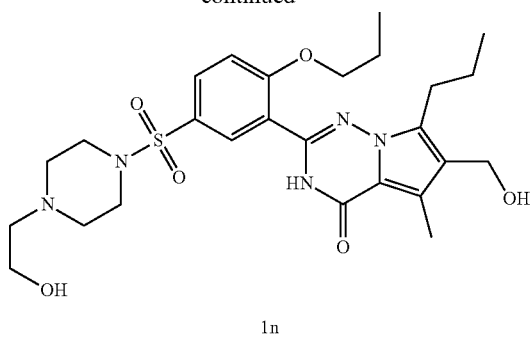

1n

Example 34

2-(5-((4-(2-hydroxyethyl)piperazin-1-yl)sulfonyl)-2-propoxyphenyl)-6-(hydroxymethyl)-5-methyl-7-propylpyrrolo[2,1-f][1,2,4]triazin-4(3H)-one (1n)

To a solution of 310 mg (0.57 mmol) 2-(5-((4-(2-hydroxyethyl)piperazin-1-yl)sulfonyl)-2-propoxyphenyl)-5-methyl-4-oxo-7-propyl-3,4-dihydropyrrolo [2,1-f][1,2,4]triazine-6-carbaldehyde (1 m) in 35 mL ethanol was added 150 mg (4 mmol) sodium borohydride. The reaction mixture was stirred over night at room temperature treated with 5 mL acetone and stirred for one hour. The reaction mixture was concentrated under reduced pressure, the residue taken up in ethyl acetate and the organic phase was washed with brine and dried with magnesium sulfate. Chromatography on silica using ethyl acetate/cyclohexane/methanol (40/60/4) gave 245 mg (79%) title compound as a white solid. $^1$H NMR (400 MHz, CDCl$_3$) δ=9.68 (s, 1H), 8.52 (d, J=2 Hz, 1H), 7.89 (dd, J=2, 9 Hz, 1H), 7.18 (d, J=9 Hz, 1H), 4.79 (s, 2H), 4.39-4.34 (m, 2H), 3.59 (m, 2H), 3.23 (t, J=7 Hz, 2H), 3.12 (brs, 4H), 2.79 (s, 3H), 2.64-2.58 (m, 6H), 1.79-1.72 (m, 4H), 1.62 (t, J=7 Hz, 3H), 0.99 (t, J=7 Hz, 3H). LCMS (M+H)=548.2, purity=97%.

SCHEME 14

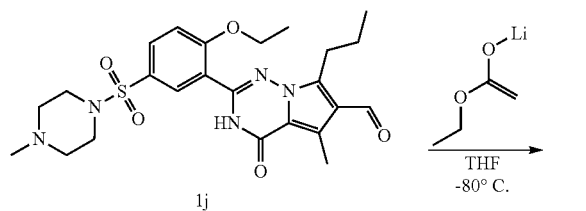

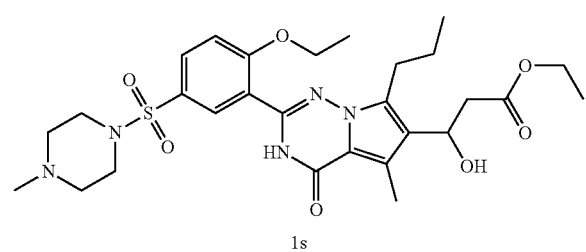

Example 35

Ethyl-3-(2-(2-ethoxy-5-((4-methylpiperazin-1-yl)sulfonyl) phenyl)-5-methyl-4-oxo-7-propyl-3,4-dihydropyrrolo[2,1-f] [1,2,4]triazin-6-yl)-3-hydroxy-propanoate (1s)

To a solution of 420 uL (3 mmol) diisopropylamine in 15 mL tetrahydrofuran at −80° C. was added 1.88 mL butyl-lithium (3 mmol) in hexane. After 10 minutes 390 uL (4 mmol) ethyl acetate was added. 118 mg (0.234 mmol) 2-(2-ethoxy-5-((4-methylpiperazin-1-yl)sulfonyl)phenyl)-5-methyl-4-oxo-7-propyl-3,4-dihydropyrrolo[2,1-f][1,2,4]triazine-6-carbaldehyde (1j) in 5 mL tetrahydrofuran was added after 10 minutes and the reaction mixture was kept at −80° C. for 2 hours. Work up with ethyl acetate and brine, magnesium sulfate drying and removal of the solvent under reduced pressure gave a colorless gum. Chromatography on silica with ethyl acetate/ethanol (5/1) gave 115 mg (83%) of the title compound as a white solid.
$^1$H NMR (500 MHz, CDCl$_3$) δ=9.94 (s, 1H), 8.34 (d, J=2 Hz, 1H), 7.77 (dd, J=2, 8.5 Hz, 1H), 7.12 (d, J=8.5 Hz, 1H), 5.31 (m, 1H), 4.34-4.30 (m, 2H), 4.21 4.16 (m, 2H), 3.05-2.90 (m, 4H), 2.63-2.48 (m, 8H), 2.59 (s, 3H) (s, 3H), 2.26 (s, 3H), 1.57 (t, J=7 Hz, 3H), 1.28 (t, J=7.5 Hz, 3H), 0.98 (t, J=7 Hz, 3H). LCMS (M+H)=590.2, purity=95%.

SCHEME 15

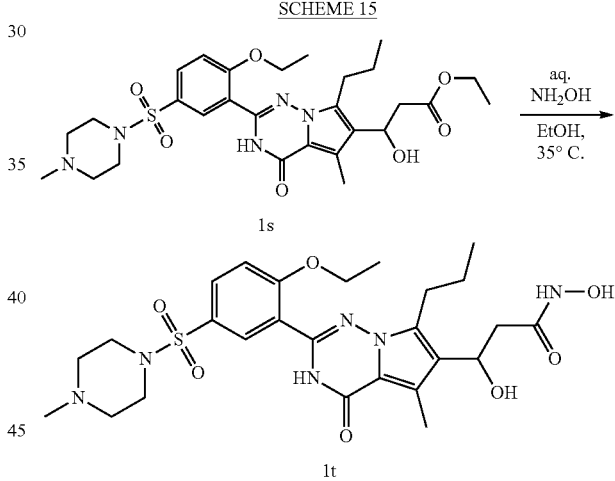

Example 36

3-(2-(2-ethoxy-5-((4-methylpiperazin-1-yl)sulfonyl) phenyl)-5-methyl-4-oxo-7-propyl-3,4-dihydropyrrolo[2,1-f][1,2,4]triazin-6-yl)-N,3-dihydroxy propanamide (1t)

50 mg (0.085 mmol) ethyl 2-(2-(2-ethoxy-5-((4-methylpiperazin-1-yl)sulfonyl)phenyl)-5-methyl-4-oxo-7-propyl-3,4-dihydro pyrrolo[2,1-f][1,2,4]triazin-6-yl)-2-hydroxyacetate (1s) was dissolved in 5 mL ethanol. 1.5 mL aqueous 50% hydrazine hydrate was added at room temperature and the reaction mixture was stirred at 35° C. for four days. Solvent was partially removed under reduced pressure, and worked up using ethyl acetate and brine. The organic phase was dried with magnesium sulfate and the solvent removed under reduced pressure. Chromatography on silica with ethyl acetate/methanol (1/2) gave 20 mg (41%) title compound as a colorless solid. $^1$H NMR (500 MHz, CDCl$_3$) δ=13.2 (s, 1H), 9.73 (s, 1H), 8.49 (s, 1H), 7.53 (m, 1H), 7.15 (m, 1H), 5.30 (m, 1H), 4.00-3.90 (m, 2H), 3.07-2.80 (m, 4H), 2.60-2.40 (m, 8H), 2.60 (s, 3H) (s, 3H), 2.30 (s, 3H), 1.33 (t, J=7 Hz, 3H), 0.88 (t, J=7 Hz, 3H). LCMS (M+H)=577.2, purity=92%.

SCHEME 16

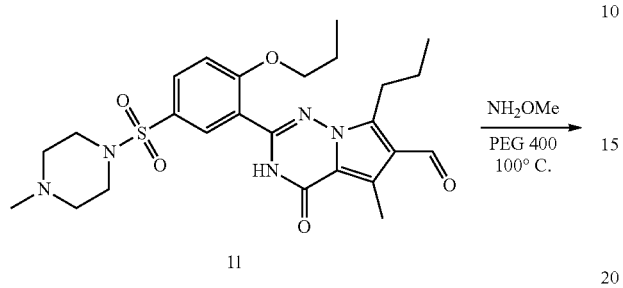

SCHEME 17

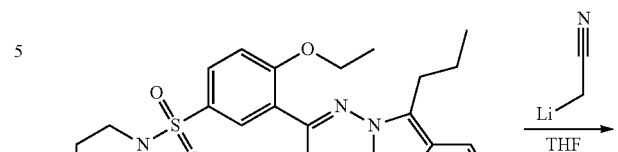

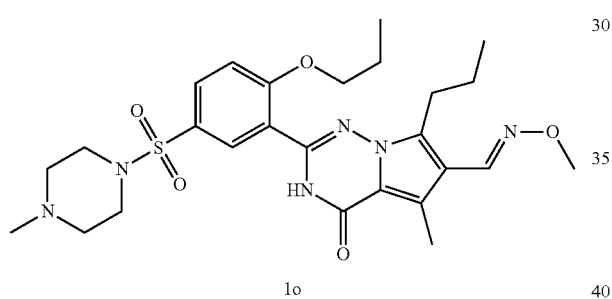

Example 38

3-(2-(2-ethoxy-5-((4-methylpiperazin-1-yl)sulfonyl) phenyl)-5-methyl-4-oxo-7-propyl-3,4-dihydropyr-rolo[2,1-f][1,2,4]triazin-6-yl)-3-hydroxy propanenitrile (1u)

Example 37

(E)-5-methyl-2-(5-((4-methylpiperazin-1-yl)sulfonyl)-2-propoxyphenyl)-4-oxo-7-propyl-3,4-dihydropyrrolo[2,1-f][1,2,4]triazine-6-carbaldehyde O-methyl oxime (1o)

30 mg (0.06 mmol) 5-methyl-2-(5-((4-methylpiperazin-1-yl)sulfonyl)-2-propoxyphenyl)-4-oxo-7-propyl-3,4-dihydropyrrolo[2,1-f][1,2,4]triazine-6-carbaldehyde, 92 mg (1.1 mmol) methylhydroxylamine hydrochloride and 46 mg (1.15 mmol) sodium hydroxide in 4.5 mL PEG-400 were heated for 8 hours to 100° C. Work up with ethyl acetate and aqueous sodium carbonate solution, drying of the organic phase with magnesium carbonate and removal of the solvent under reduced pressure gave 19 mg (60%) title compound. $^1$H NMR (500 MHz, CDCl$_3$) δ=9.81 (s, 1H), 8.45 (d, J=2 Hz, 1H), 8.20 (s, 1H), 7.85 (dd, J=2, 9 Hz, 1H), 7.14 (d, J=9 Hz, 1H), 3.96 (s, 3H), 3.73-3.59 (m, 2H), 3.09-3.00 (m, 4H), 2.63 (s, 3H), 2.53-2.50 (m, 4H), 2.29 (s, 3H), 1.72-1.60 (m, 4H), 0.98 (t, J=7 Hz, 3H), 0.95 (t, J=8 Hz, 3H). LCMS (M+H)=545.2, purity=89%.

To a solution of 420 uL (3 mmol) diisopropylamine in 15 mL tetrahydrofuran 1.88 mL butyllithium was added at −80° C. After 15 minutes 0.5 mL acetonitrile were added and the solution stirred for 15 minutes at −80° C. 90 mg (0.18 mmol) 2-(2-ethoxy-5-((4-methylpiperazin-1-yl)sulfonyl)phenyl)-5-methyl-4-oxo-7-propyl-3,4-dihydropyrrolo[2,1-f][1,2,4]triazine-6-carbaldehyde (1j) was added in 5 mL tetrahydrofuran was added and the reaction mixture was warmed up to 0° C. Work up with ethyl acetate and chromatography on silica using ethyl acetate/aceton (2/1) gave 60 mg (60%) title compound as a white solid. $^1$H NMR (500 MHz, CDCl$_3$) δ=9.90 (s, 1H), 8.32 (d, J=2 Hz; 1H), 7.75 (dd, J=4, 9 Hz; 1H), 7.13 (d, J=9 Hz; 1H), 5.19 (t, J=8 Hz, 1H), 4.35 (m, 2H), 3.00-2.70 (m, 8H), 2.47 (s, 3H), 2.26 (s, 3H), 1.69-1.60 (m, 2H), 1.61 (t, J=7 Hz, 3H), 0.98 (t, J=7 Hz, 3H). LCMS (M+H)=543.2, purity=92%.

SCHEME 18

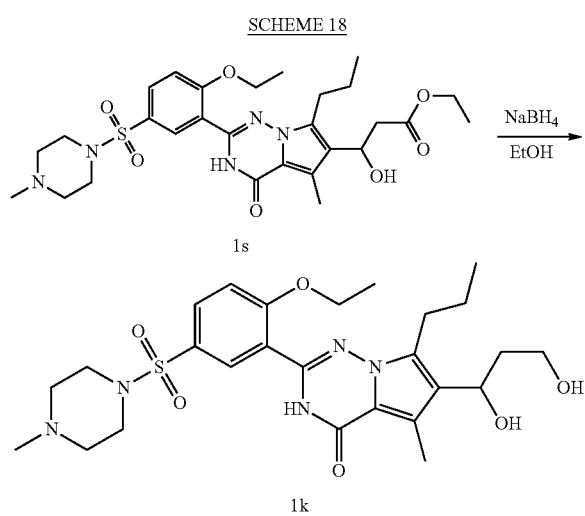

Example 39

6-(1,3-dihydroxypropyl)-2-(2-ethoxy-5-((4-methylpiperazin-1-yl)sulfonyl) phenyl)-5-methyl-7-propylpyrrolo[2.1-][1,2,4]triazin-4(3H)-one (1k)

To a solution of 45 mg (0.08 mmol) ethyl 3-(2-(2-ethoxy-5-((4-methylpiperazin-1-yl)sulfonyl)phenyl)-5-methyl-4-oxo-7-propyl-3,4-dihydropyrrolo[2,1-f][1,2,4] triazin-6-yl)-3-hydroxypropanoate (1s) was added 380 mg (10 mmol) sodium borohydride. The reaction mixture was heated to reflux for 12 hours. At room temperature 3 mL action was added and the reaction mixture was warmed up to 50° C. for 30 minutes. Standard work up using ethyl acetate and aqueous sodium carbonate afforded after chromatography on silica with ethyl acetate/methanol (3/1) 15 mg title compound as a colorless resin. $^1$H NMR (500 MHz, CDCl$_3$) δ=9.73 (s, 1H), 8.41 (d, J=2 Hz, 1H), 7.78 (dd, J=2, 9 Hz, 1H), 7.13 (d, J=9 Hz, 1H), 5.13 (dd, J=4, 10 Hz, 1H), 3.89 (m, 2H), 3.07-2.80 (m, 4H), 2.55 (s, 3H) (s, 3H), 2.27 (s, 3H), 1.70-1.30 (m, 4H), 1.58 (t, J=7 Hz, 3H), 0.98 (t, J=7 Hz, 3H). LCMS (M+H)=548.3, purity=92%.

SCHEME 19

Example 40

5-((4-(2-(Benzoyloxy)ethyl)piperazin-1-yl)sulfonyl)-2-ethoxybenzoic acid (21)

A solution of 5-(chlorosulfonyl)-2-ethoxybenzoic acid (9) (5.66 g, 21.43 mmol) in dichloromethane (50 mL) was added to a cooled solution of 2-(Piperazin-1-yl)ethyl benzoate (5.54 g, 23.67 mmol) and triethylamine (8.8 mL, 64.53 mmol) in dichloromethane (100 mL) at 0° C. The resultant reaction mixture was stirred at RT for 16 h. On completion, the reaction mixture was concentrated. The obtained residue was acidified with 5% aqueous citric acid solution and extracted with ethyl acetate (3×200 mL). The combined ethyl acetate layers was washed with brine (50 mL), dried over anhydrous sodium sulfate and concentrated to afford the title 21 (9.7g) as brown solid. $^1$H NMR (400 MHz, CDCl$_3$) δ=8.48 (br d, J=2.4 Hz, 1H), 7.98 (br d, J=8.3 Hz, 2H), 7.91 (dd, J=2.2, 8.6 Hz, 1H), 7.59-7.53 (m, 1H), 7.47-7.39 (m, 2H), 7.18-7.12 (m, 1H), 4.45 (br t, J=5.6 Hz, 2H), 4.41-4.33 (m, 2H), 3.12 (br s, 4H), 2.89 (br t, J=4.9 Hz, 2H), 2.80 (br s, 4H), 1.59 (dt, J=2.7, 7.0 Hz, 3H). LCMS (M+H)=463.3, purity~78%.

Example 41

Ethyl-1-(5-((4-(2-(benzoyloxy)ethyl)piperazin-1-yl)sulfonyl)-2-ethoxybenzamido)-4-formyl-3-methyl-5-propyl-1H-pyrrole-2-carboxylate (22)

To a stirring solution of 5-((4-(2-(Benzoyloxy)ethyl)piperazin-1-yl)sulfonyl)-2-ethoxybenzoic acid (21) (3.5g, 7.55 mmol) in DMF (35 mL), was added TBTU (4.85 g, 15.11 mmol) and diisopropylethyl amine (3.96 mL, 22.67 mmol) to this 14 (2.15 g, 9.07 mmol) was added and the resultant reaction mixture was stirred at RT for 16 h. The reaction mixture was diluted with water and extracted with ethyl acetate (3×200 mL). The combined ethyl acetate layer was washed with brine, dried over anhydrous sodium sulfate and concentrated under reduced pressure. Purification by column chromatography (100-200 mesh silica gel, 1-3% methanol in dichloromethane as eluent) afforded the title compound 22 (3.8g) as brown gum. $^1$H NMR (300 MHz, DMSO-d6) δ=11.43 (s, 1H), 10.00 (s, 1H), 7.94-7.80 (m, 4H), 7.68-7.59 (m, 1H), 7.54-7.46 (m, 2H), 7.42 (d, J=8.8 Hz, 1H), 4.46-4.24 (m, 4H), 4.17 (q, J=7.2 Hz, 2H), 2.97-2.90 (m, 4H), 2.89 (s, 11H), 2.73 (s, 8H), 2.69 (s, 3H), 2.59 (br s, 2H), 2.54 (s, 3H), 1.58 (br dd, J=7.3, 15.0 Hz, 2H), 1.41 (t, J=7.0 Hz, 3H), 1.16 (t, J=7.2 Hz, 3H), 0.90 (t, J=7.3 Hz, 3H), LC-MS (M+H)=684.0, purity~85%.

Example 42

1-(2-ethoxy-5-((4-(2-hydroxyethyl)piperazin-1-yl)sulfonyl)benzamido)-4-formyl-3-methyl-5-propyl-1H-pyrrole-2-carboxylic acid (23)

To a solution of 22 (10.6g, 15.54 mmol) in MeOH (100 mL) and H$_2$O (100 mL), NaOH (10 g, w/w) was added and stirred at 60° C. for 6 h. On completion, the reaction mixture was concentrated; the obtained aqueous residue was acidified with 1N HCl. The obtained solid was filtered, dried and washed with Et$_2$O (3×20 mL) to afford 23 (4.1 g) as white solid. $^1$H NMR (300 MHz, DMSO-d6) δ=11.48 (s, 1H), 10.00 (s, 1H), 7.91-7.78 (m, 2H), 7.41 (d, J=8.8 Hz, 1H), 4.27 (q, J=7.0 Hz, 2H), 3.44 (br s, 2H), 2.88 (br s, 6H), 2.54 (s, 3H), 2.39 (br d, J=12.1 Hz, 2H), 1.68-1.50 (m, 2H), 1.40 (t, J=7.0 Hz, 3H), 0.90 (t, J=7.3 Hz, 3H). LC-MS (M–H)= 551.4, purity~91%.

Example 43

1-(2-ethoxy-5-((4-(2-hydroxyethyl)piperazin-1-yl)sulfonyl)benzamido)-4-formyl-3-methyl-5-propyl-1H-pyrrole-2-carboxamide (24)

To a stirring solution of 23 (1.68g, 3.054 mmol) in DMF (8 mL), TBTU (1.96 g, 6.10 mmol) and DIPEA (2.9 mL, 15.27 mmol) was added and stirred at RT for 30 min. To the obtained reaction mixture NH$_4$Cl (0.5 g, 9.16 mmol) was added and the mixture was stirred at RT for 16 h. On completion, the reaction mixture was quenched with water (130 mL) and extracted with EtOAc (2×100 mL). The combined organic layer was washed with water (2×40 mL), brine (30 mL), dried over anhydrous Na$_2$SO$_4$ and concentrated. The obtained crude was purified by silica gel (230-400 mesh) column chromatography using 10% Methanol in dichloromethane as eluent to afford the title compound 24 (2 g) as white solid. $^1$H NMR (400 MHz, CDCl$_3$) δ=10.80 (br s, 1H), 10.04 (s, 1H), 8.50 (d, J=2.4 Hz, 1H), 7.89 (dd, J=2.4, 8.8 Hz, 1H), 7.15 (d, J=8.8 Hz, 1H), 5.73 (br s, 2H), 4.40 (q, J=7.2 Hz, 2H), 3.64 (t, J=5.4 Hz, 2H), 3.10 (br s, 4H), 2.70 (br t, J=4.6 Hz, 4H), 2.67-2.61 (m, 2H), 2.56 (s, 3H), 1.65 (t, J=6.8 Hz, 3H), 0.97 (t, J=7.3 Hz, 3H). LCMS (M+H)= 550.4, purity~96.5%.

Example 44

2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde (1w)

A solution of 24 (200 mg, 0.36 mmol) in absolute ethanol (5 mL) was added 1M aqueous KOH solution (5 mL) and stirred at 95° C. in a sealed tube for 72 h. The reaction mixture was concentrated completely under reduced pressure. The crude was added water (5 mL) and stirred at RT for 10 min; the resulted solid was filtered, washed with diethyl ether (3×5 mL) and dried to afford the title 1w (110 mg) as brown solid. $^1$H NMR (400 MHz, CDCl$_3$) δ=10.19 (s, 1H), 9.69 (s, 1H), 8.53 (d, J=2.4 Hz, 1H), 7.89 (dd, J=2.4 Hz, 8.8 Hz; 1H), 7.18 (d, J=8.8 Hz, 1H), 4.39-4.34 (m, 2H), 3.59 (m, 1H), 3.22 (t, J=7.2 Hz, 2H), 3.11 (brs, 4H), 2.64-2.57 (m, 6H), 1.79-1.73 (m, 2H), 1.62 (t t, J=7.2 Hz, 3H), 0.99 (t, J=7.2 Hz, 3H), LCMS (M+H)=532.4, purity~99%.

SCHEME 20

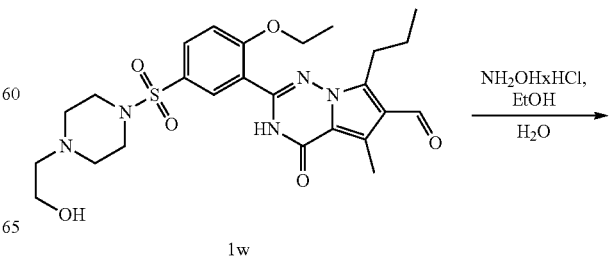

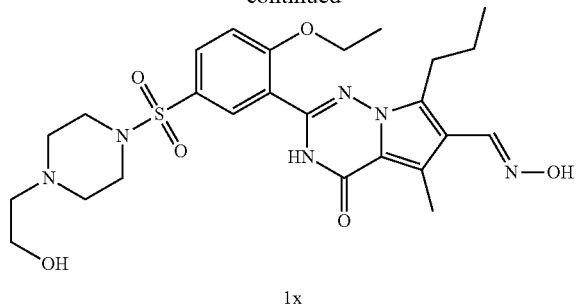

1x

Example 45

(E)-2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde oxime (1x)

To a stirring solution of 2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde (1w) (80 mg, 0.15 mmol) in Ethanol (3 mL) and water (0.5 mL) was added hydroxylamine hydrochloride (26.17 mg, 0.376 mmol) and the reaction mixture was heated to 85° C. for 5 h. On completion, the reaction mixture was concentrated under reduced pressure. The obtained residue was stirred in water (1 mL), filtered, washed with diethyl ether (2×3 mL) and dried to afford 1x (60 mg) as a white solid. $^1$H NMR (400 MHz, DMSO-d6) δ=11.62 (s, 1H), 10.95 (s, 1H), 9.72 (brs, 1H), 8.21 (s, 1H), 7.91-7.89 (m, 2H), 7.44 (d, J=8.8 Hz; 1H), 5.31 (br, 1H), 4.26-4.21 (m, 2H), 3.77-3.69 (m, 4H), 3.54 (br, 2H), 3.19 (m, 4H), 2.96-2.92 (m, 2H), 2.79-2.73 (m, 2H), 2.55 (s, 3H), 1.63-1.56 (m, 2H), 1.35 (t, J=6.8 Hz, 3H), 0.88 (t, J=7.6 Hz, 3H), LCMS (M+H)=547.8, purity~93.6% (mixture of syn & anti isomers).

SCHEME 21

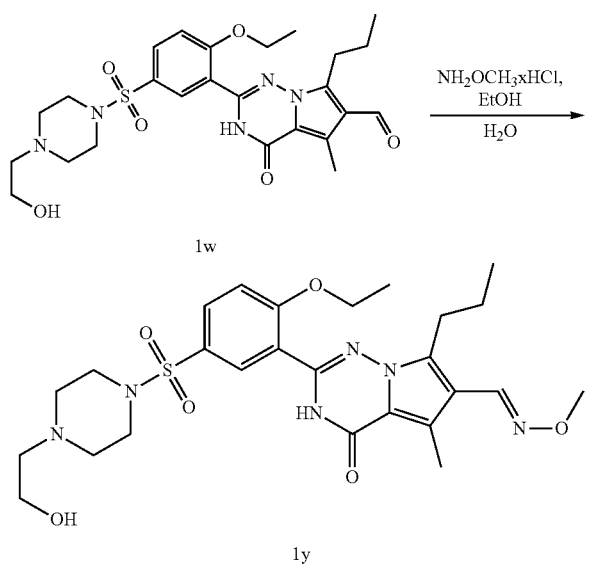

Example 46

2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde O-methyloxime (1y)

To a stirring solution of 2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde (1w) (80 mg, 0.15 mmol) in ethanol (3 mL) and water (0.5 mL) was added methoxylamine hydrochloride (31.5 mg, 0.376 mmol) and the reaction mixture was heated to 85° C. for 4 h. On completion, the reaction mixture was concentrated under reduced pressure. The obtained residue was stirred in water (1 mL), filtered, washed with diethyl ether (2×3 mL) and dried to afford the title compound 1y (58 mg) as a white solid. $^1$H NMR (400 MHz, CDCl$_3$) δ=8.23 (s, 1H), 8.06 (dd, J=2, 8.8 Hz, 1H), 7.18 (d, J=8.8 Hz, 1H), 4.30 (q, J=6.8 Hz, 2H), 3.67-3.64 (m, 2H), 3.12-3.03 (m, 5H), 2.76 (br, 4H), 2.66-2.64 (m, 2H, 2.61 (s, 3H), 1.73-1.67 (m, 2H), 1.48 (t, J=6.8 Hz, 3H), 0.95 (t, J=7.2 Hz, 3H), LCMS (M+H)=561.37, purity~96%.

SCHEME 22

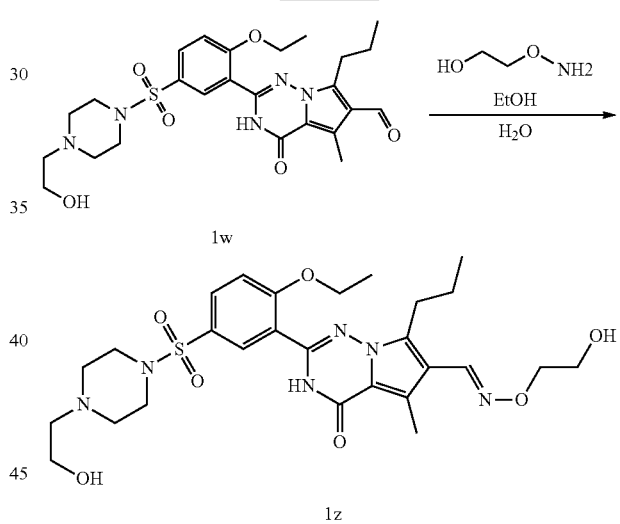

Example 47

(E)-2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde O-(2-hydroxyethyl) oxime (1z)

To a stirring solution of 2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde (1w) (50 mg, 0.094 mmol) in ethanol (2 mL) and water (0.5 mL) was added 2-Aminoxyethanol (25.4 mg, 0.33 mmol) and the reaction mixture was heated to 85° C. for 16 h. On completion, the reaction mixture was concentrated under reduced pressure. The obtained residue was stirred in water (1 mL), filtered, washed with diethyl ether (2×3 mL). The obtained crude was further purified by PREP TLC using 25% Acetone in dichloromethane as eluent to afford the title 1z (33 mg) as a white solid $^1$H NMR (400 MHz, CDCl$_3$) δ=11.62 (s, 1H), 8.30 (s, 1H), 7.86-7.82 (m, 2H), 7.39 (d, J=8.8 Hz, 1H), 4.70-4.67 (m, 1H), 4.36-4.35 (m, 1H), 4.24-4.19 (m, 2H), 4.09-4.07 (m, 2H), 3.68-3.67 (m, 2H), 3.44-3.41 (m, 2H), 2.96-2.88 (m, 6H), 2.55 (s, 3H), 2.37-2.34 (m, 2H), 1.62-1.56 (m, 2H), 1.33 (t, J=7.2 Hz, 3H), 0.88 (t, J=7.6 Hz, 3H), LCMS (M+H)=591.37, purity~95.7%.

The reaction mixture was filtered and the filtrate was concentrated under reduced pressure. Purification of the crude by column chromatography (100-200 mesh silica gel, 5% methanol in dichloromethane as eluent) afforded the title compound 26 (7.5 g) as solid. [SM was recovered by eluting with 5% ethyl acetate in pet ether as eluent]. $^1$H NMR (400 MHz, CDCl$_3$) δ=10.01 (s, 1H), 9.00 (br s, 1H), 3.88 (s, 3H),

SCHEME 23

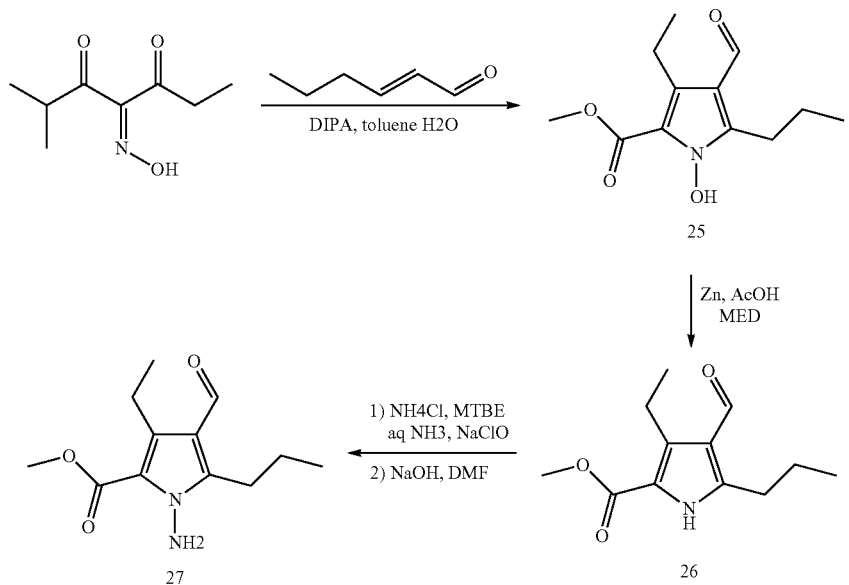

Example 48

Methyl-3-ethyl-4-formyl-1-hydroxy-5-propyl-1H-pyrrole-2-carboxylate (25)

(Z)-ethyl 2-(hydroxyimino)-3-oxopentanoate (35 g, 219.99 mmol), (E)-hex-2-enal (50.9 mL, 439.9 mmol) in toluene, was added di-isopropylamine (6.2 mL, 43.99 mmol) and the resultant reaction mixture was stirred at RT for 16 h. The reaction mixture was quenched with aqueous Ammonium chloride solution (300 mL) and extracted with dichloromethane (2×300 mL). The combined dichloromethane layer was washed with brine and dried over anhydrous sodium sulfate and concentrated under reduced pressure. Purification by column chromatography (100-200 mesh silica gel, 0-5% ethyl acetate in pet ether as eluent) afforded the title compound 25 (31 g) as gum. $^1$H NMR (400 MHz, CDCl$_3$) δ=12.27 (br s, 1H), 9.94 (s, 1H), 3.97 (s, 3H), 3.02 (q, J=7.3 Hz, 2H), 2.98-2.92 (m, 2H), 1.77-1.63 (m, 2H), 1.19 (t, J=7.3 Hz, 3H), 0.97 (t, J=7.3 Hz, 3H), Mass (M+H)=240.2.

Example 49

Methyl-3-ethyl-4-formyl-5-propyl-1H-pyrrole-2-carboxylate (26)

To a stirring solution of ethyl 4-formyl-1-hydroxy-3-ethyl-5-propyl-1H-pyrrole-2-carboxylate (25) (10g, 41.84 mmol) in dichloromethane (800 mL) and acetic acid (40 mL), zinc dust (27.4 g, 418.41 mmol) was added in portions and the resultant reaction mixture was stirred at RT for 8 h.

3.07 (q, J=7.7 Hz, 2H), 2.91 (t, J=7.6 Hz, 2H), 1.76-1.65 (m, 2H), 1.20 (t, J=7.3 Hz, 3H), 0.99 (t, J=7.3 Hz, 3H), LCMS (M+H)=224.3, purity~96%.

Example 50

Methyl-1-amino-3-ethyl-4-formyl-5-propyl-1H-pyrrole-2-carboxylate (27)

To a stirring solution of 26 (5 g, 22.42 mmol), in DMF (50 mL) at 0° C., NaOH (4.48g, 112.1 mmol) was added in portions. After addition the mixture was stirred at 0° C. for 1 h before cooled it to −20° C. The obtained mixture was treated with chloramine solution in MTBE (freshly prepared from NH$_4$Cl (15 g) in MTBE (400 mL) added 30% aqueous ammonia (30 mL) and cooled to −20° C. To the mixture sodium hypochlorite solution (120 mL, commercial grade in water) was added drop wise. After addition the reaction mixture was stirred at −20° C. for 1 h. The MTBE layer was separated from the biphasic mixture) was added slowly for 20 min. After addition, the reaction mixture was allowed to stir at RT for 3 h. On completion, the reaction mixture was quenched with water and separated the organic layer. The MTBE layer was washed with 5% sodium thiosulfate solution and water (100 mL), dried over anhydrous sodium sulfate and concentrated under reduced pressure to afford the title compound 27 (5.2 g) as brown solid.

$^1$H NMR (400 MHz, CDCl$_3$) δ=9.97 (s, 1H), 5.39 (s, 2H), 3.89 (s, 3H), 3.09-2.96 (m, 4H), 1.68-1.60 (m, 2H), 1.21-1.12 (m, 3H), 0.98 (t, J=7.3 Hz, 3H), LCMS (M+H)=239.1, purity~81%.

SCHEME 24

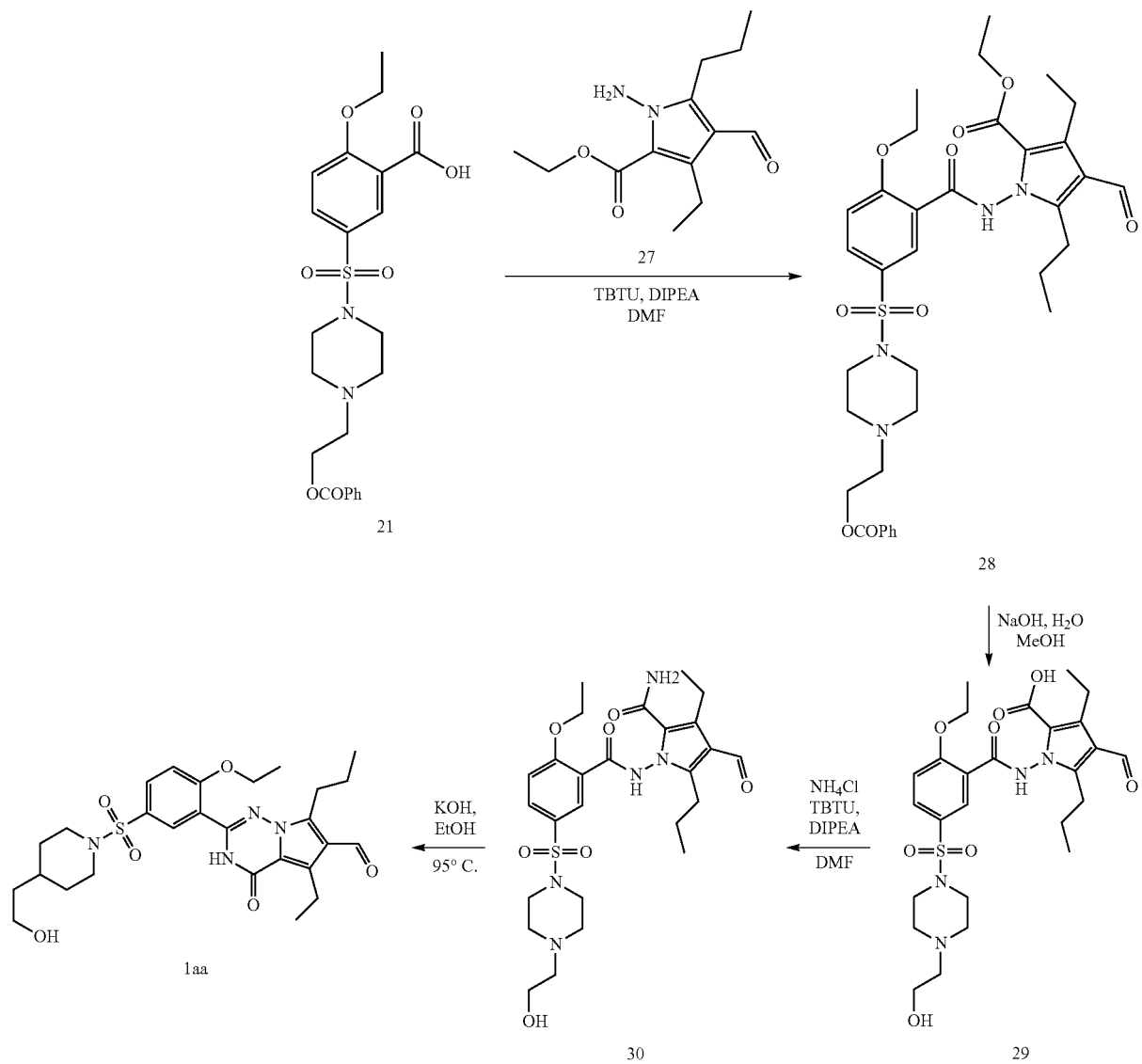

Example 51

Methyl-1-(5-((4-(2-(benzoyloxy)ethyl)piperazin-1-yl)sulfonyl)-2-ethoxybenzamido)-3-ethyl-4-formyl-5-propyl-1H-pyrrole-2-carboxylate (28)

To a stirring solution of 5-((4-(2-(Benzoyloxy)ethyl)piperazin-1-yl)sulfonyl)-2-ethoxybenzoic acid (21) (9.7g, 20.99 mmol) in DMF (90 mL), was added HBTU (13.42 g, 41.9 mmol) and diisopropyl ethyl amine (10.8 mL, 62.9 mmol) to this 27 (5.86 g, 24.77 mmol) was added and the resultant reaction mixture was stirred at RT for 16 h. The reaction mixture was diluted with water and extracted with ethyl acetate (2×200 mL). The combined ethyl acetate layer was washed with brine, dried over anhydrous sodium sulfate and concentrated under reduced pressure. Purification by column chromatography (100-200 mesh silica gel, 0.5% methanol in dichloromethane as eluent) afforded the title compound 28 (9.5g) as brown solid. $^1$H NMR (400 MHz, CDCl$_3$) δ=10.41 (s, 1H), 10.06 (s, 1H), 8.57 (d, J=2.4 Hz, 1H), 8.01-7.97 (m, 2H), 7.93 (dd, J=2.4, 8.3 Hz, 1H), 7.60-7.52 (m, 1H), 7.47-7.38 (m, 2H), 7.18 (d, J=8.8 Hz, 1H), 4.49-4.33 (m, 4H), 3.77 (s, 3H), 3.06 (br s, 5H), 2.78 (br t, J=5.6 Hz, 1H), 2.67 (br s, 4H), 1.71-1.59 (m, 4H), 1.22 (t, J=7.6 Hz, 2H), 0.96 (t, J=7.3 Hz, 3H), LCMS (M+H) =685.3, purity~80%.

Example 52

1-(2-ethoxy-5-((4-(2-hydroxyethyl)piperazin-1-yl)sulfonyl)benzamido)-3-ethyl-4-formyl-5-propyl-1H-pyrrole-2-carboxylic acid (29)

To a solution of 28 (9.5g, 13.9 mmol) in MeOH (100 mL) and H$_2$O (100 mL), NaOH (9.5g, w/w) was added and stirred at 60° C. for 3 h. On completion, the reaction mixture was concentrated; the obtained aqueous residue was acidified with 1N HCl. The obtained solid was filtered, dried and washed with Et₂O (3×10 mL) to afford 29 (6 g) as white solid. ¹H NMR (400 MHz, DMSO-d6) δ=9.96 (s, 1H), 7.91 (d, J=2.4 Hz, 1H), 7.82 (dd, J=2.4, 8.8 Hz, 1H), 7.39 (d, J=8.8 Hz, 1H), 4.27 (q, J=6.8 Hz, 2H), 3.42 (br t, J=6.1 Hz, 4H), 3.06 (q, J=7.2 Hz, 2H), 2.93-2.75 (m, 6H), 2.36 (t, J=6.1 Hz, 2H), 1.58 (qd, J=7.5, 15.1 Hz, 2H), 1.40 (t, J=7.1 Hz, 3H), 1.10 (t, J=7.3 Hz, 3H), 0.89 (t, J=7.3 Hz, 3H), LC-MS (M+H)=565.5, purity~88.2%.

Example 53

1-(2-ethoxy-5-((4-(2-hydroxyethyl)piperazin-1-yl)sulfonyl)benzamido)-3-ethyl-4-formyl-5-propyl-1H-pyrrole-2-carboxamide (30)

To a stirring solution of 29 (6g, 10.65 mmol) in DMF (60 mL), TBTU (6.84 g, 21.31 mmol) and DIPEA (9.46 mL, 31.95 mmol) was added and stirred at RT for 30 min. To the obtained reaction mixture NH₄Cl (1.14g, 21.31 mmol) was added and the mixture was stirred at RT for 16 h. On completion, the reaction mixture was quenched with water (200 mL) and extracted with EtoAc (2×100 mL). The combined organic layer was washed with water 2×50 mL), brine (30 mL), dried over anhydrous Na₂SO₄ and concentrated. The obtained crude was purified by silica gel (230-400 mesh) column chromatography using 10% Methanol in dichloromethane as eluent to afford the title compound 30 (3 g) as white solid. ¹H NMR (400 MHz, DMSO-d6) δ=10.70 (s, 1H), 10.04 (s, 1H), 8.54 (d, J=2.0 Hz, 1H), 7.92 (dd, J=2.4, 8.8 Hz, 1H), 7.18 (d, J=8.8 Hz, 1H), 5.59 (br s, 2H), 4.43 (q, J=7.0 Hz, 2H), 3.59 (t, J=5.4 Hz, 2H), 3.15-2.89 (m, 6H), 2.72-2.51 (m, 6H), 1.72-1.58 (m, 5H), 1.28 (t, J=7.3 Hz, 3H), 0.97 (t, J=7.3 Hz, 3H), LCMS (M+H)=564.9, purity~95.5%.

Example 54

2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde (1aa)

A solution of 30 (300 mg, 0.53 mmol) in absolute ethanol (8 mL) was added 1M aqueous KOH solution (8 mL) and stirred at 95° C. in a sealed tube for 72 h. The reaction mixture was concentrated completely under reduced pressure. The crude was added water (8 mL) and stirred at RT for 10 min, the resulted solid was filtered, washed with diethyl ether (3×4 mL) and dried to afford the title 1aa (220 mg) as brown solid. ¹H NMR (300 MHz, CDCl₃) δ=10.19 (s, 1H), 9.72 (brs, 1H), 8.55 (d, J=2.4 Hz, 1H), 7.89 (dd, J=2.4, 8.8 Hz; 1H), 7.18 (d, J=8.7 Hz, 1H), 4.40-4.33 (m, 2H), 3.58 (brs, 2H), 3.31-3.20 (m, 4H), 3.09 (brm, 4H), 2.63-2.54 (m, 6H), 1.80-1.73 (m, 2H), 1.63 (t, J=7.2 Hz, 3H), 1.30 (t, J=7.4 Hz, 3H), 1.00 (t, J=7.2 Hz, 3H), LCMS (M+H)=544.5, purity~95%.

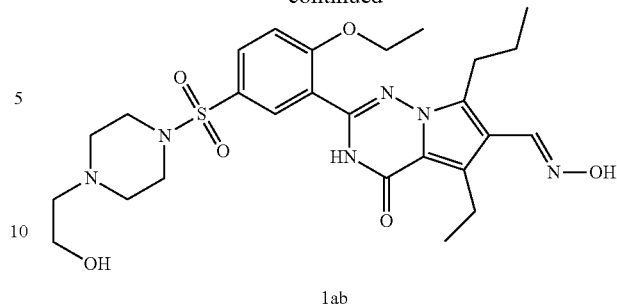

1ab

Example 55

(E)-2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde oxime (1ab)

To a stirring solution of 2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde (1aa) (100 mg, 0.183 mmol) in ethanol (3 mL) and water (0.5 mL) was added hydroxylamine hydrochloride (70 mg, 0.458 mmol) and the reaction mixture was heated to 85° C. for 4 h. On completion, the reaction mixture was concentrated under reduced pressure. The obtained residue was stirred in water (1 mL), filtered, washed with diethyl ether (2×3 mL) and dried to afford the title 1ab (24 mg) as white solid. ¹H NMR (400 MHz, DMSO-d6) δ=11.64 (s, 1H), 10.95 (brs, 1H), 8.21 (s, 1H), 7.90 (brs, 1H), 7.43 (br, 1H), 5.32 (br, 1H), 4.24-4.23 (m, 2H), 3.74-3.69 (m, 3H), 3.53-3.36 (m, 2H), 3.19 (brn, 3H), 3.09-3.03 (m, 2H), 2.96-2.66 (m, 5H), 1.63-1.57 (m, 2H), 1.36-1.33 (m, 3H), 1.14 (t, J=7.4 Hz, 3H), 0.88 (t, J=7.4 Hz, 3H), LCMS (M+H)=561.3, purity~94%+2.7% (mixture of syn & anti isomers).

SCHEME 26

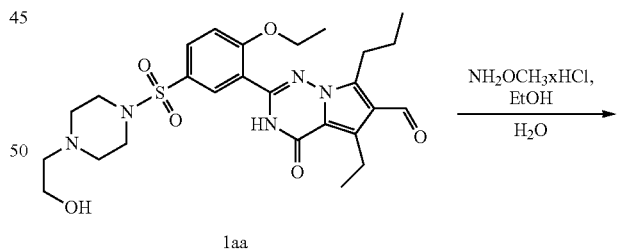

1aa

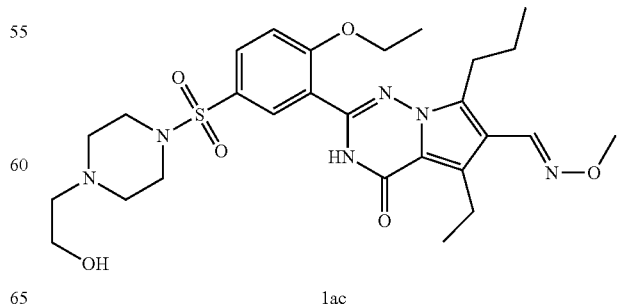

1ac

SCHEME 25

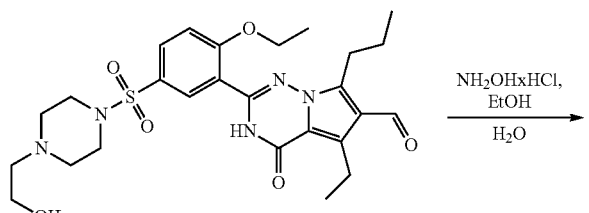

1aa

Example 56

2-(2-Ethoxy-5-((4-(2-hydroxyethyl)piperazin-1-yl)sulfonyl)phenyl)-5-ethyl-4-oxo-7-propyl-3,4-dihydropyrrolo[2,1-J][1,2,4]triazine-6-carbaldehyde O-methyloxime (1ac)

To a stirring solution of 2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde (1aa) (100 mg, 0.183 mmol) in ethanol (2 mL) and water (0.5 mL) was added methoxylamine hydrochloride (38.3 mg, 0.458 mmol) and the reaction mixture was heated to 85° C. for 4 h. On completion, the reaction mixture was concentrated; the obtained crude was dissolved in 10% methanol and dichloromethane (10 mL) mixture and washed with water (3 mL). The organic layer was dried over anhydrous $Na_2SO_4$ and concentrated under reduced pressure to afford the title 1ac (32 mg) as brown solid. $^1$H NMR (400 MHz, $CD_3OD$) δ=8.22 (s, 1H), 8.06 (d, J=2.4 Hz, 1H), 7.93 (dd, J=2.4 Hz, 8.8 Hz; 1H), 7.37 (d, J=8.8 Hz, 1H), 4.30 (q, J=6.8 Hz, 2H), 3.91 (s, 3H), 3.66-3.63 (m, 2H), 3.15-3.04 (m, 8H), 2.72-2.62 (m, 6H), 1.73-1.67 (m, 2H), 1.48 (t, J=7.4 Hz, 3H), 1.21 (t, J=7.2 Hz, 3H), 0.96 (t, J=7.2 Hz, 3H), LCMS (M+H)=575.3, purity~94.7%+4.7% (mixture of syn & anti isomers).

SCHEME 27

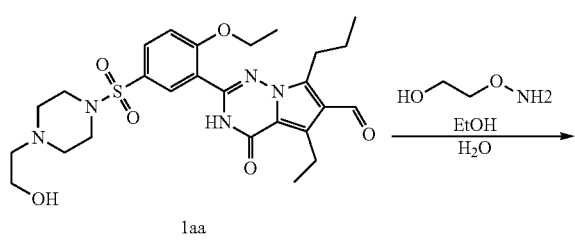

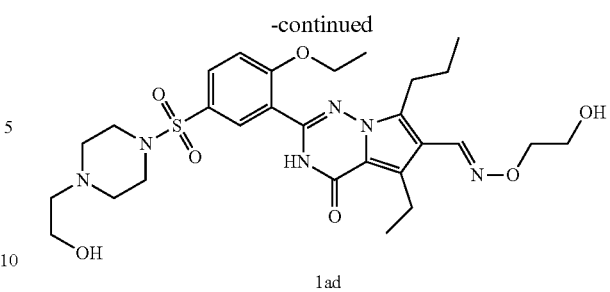

1ad

Example 57

(E)-2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde O-(2-hydroxyethyl) oxime (1ad)

To a stirring solution of 2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde (1aa) (80 mg, 0.146 mmol) in ethanol (3 mL) and water (0.5 mL) was added 2-Aminoxyethanol (39.6 mg, 0.51 mmol) and the reaction mixture was heated to 85° C. for 16 h. On completion, the reaction mixture was concentrated; the obtained crude was purified by PREP HPLC using 4% methanol in dichloromethane to afford the title 1ad (20 mg) as a brown solid. $^1$H NMR (400 MHz, $CD_3OD$) δ=8.30 (s, 1H), 8.05 (d, J=2.4 Hz, 1H), 7.92 (dd, J=2.4 Hz, 8.8 Hz; 1H), 7.36 (d, J=8.8 Hz, 1H), 4.30 (q, J=7.6 Hz, 2H), 4.20-4.17 (m, 2H), 3.84-3.82 (m, 2H), 3.62-3.60 (m, 2H), 3.15-3.04 (m, 6H), 2.62-2.61 (m, 4H), 2.53-2.50 (m, 2H), 1.73-1.68 (m, 2H), 1.48 (t, J=6.8 Hz, 3H), 1.21 (t, J=7.2 Hz, 3H), 0.96 (t, J=7.4 Hz, 3H), LCMS (M+H)=605.8, purity~93.6%.

SCHEME 28

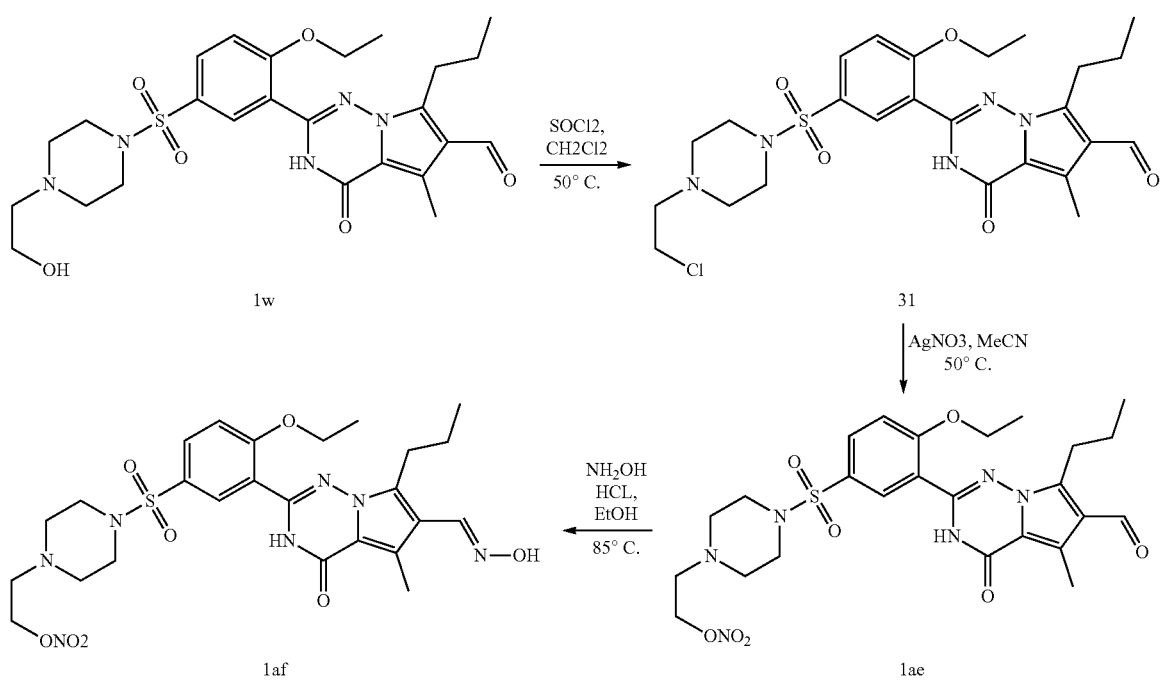

Example 58

2-(5-((4-(2-chloroethyl)piperazin-1-yl)sulfonyl)-2-ethoxyphenyl)-5-methyl-4-oxo-7-propyl-3,4-dihydropyrrolo[2,1-f][1,2,4]triazine-6-carbaldehyde (31)

To a stirred solution of 2-(2-ethoxy-5-((4-(2-hydroxyethyl)piperazin-1-yl)sulfonyl)phenyl)-5-methyl-4-oxo-7-propyl-3,4-dihydropyrrolo[2,1-f][1,2,4]triazine-6-carbaldehyde (1w) (200 mg, 0.376 mmol) in dichloromethane (5 mL), was added SOCl$_2$ (0.054 mL, 0.753 mmol) at 0° C. The reaction mixture was heated to 50° C. and stirred for 12 h. On completion, the reaction mixture was concentrated under reduced pressure. The obtained residue was diluted with water (10 mL) and extracted with dichloromethane (2×15 mL). The combined organic layers were dried over anhydrous sodium sulfate and concentrated under reduced pressure to afford the title compound 31 (200 mg) as a brown solid, which was directly taken for next reaction without further purification. MS (M+H)=550.2.

Example 59

2-(4-((4-ethoxy-3-(6-formyl-5-methyl-4-oxo-7-propyl-3,4-dihydropyrrolo[2,1-f][1,2,4]triazin-2-yl)phenyl)sulfonyl)piperazin-1-yl)ethyl nitrate (1ae)

To a stirred solution of 2-(5-((4-(2-chloroethyl)piperazin-1-yl)sulfonyl)-2-ethoxyphenyl)-5-methyl-4-oxo-7-propyl-3,4-dihydropyrrolo[2,1-f][1,2,4]triazine-6-carbaldehyde (31) (200 mg, 0.364 mmol) in acetonitrile (5 mL), was added AgNO$_3$ (247.5 mg, 1.457 mmol) at RT. The reaction was then heated to 50° C. and stirred for 16 h. On completion, the reaction mixture was cooled to RT and filtered through a celite bed. The filtrate was concentrated under reduced pressure, diluted with water (15 mL) and extracted with ethyl acetate (2×20 mL). The combined organic layers were dried over anhydrous sodium sulfate and concentrated under reduced pressure to afford the crude product (260 mg; LCMS-82%) as an pale yellow solid. A portion of the crude product (160 mg) was purified by reverse phase preparative HPLC using 0.1% formic acid in water and acetonitrile to afford the title compound 1ae (23 mg) as an off-white solid. $^1$H NMR (400 MHz, CDCl$_3$) δ=10.19 (s, 1H), 9.69 (br s, 1H; D$_2$O exchangeable), 8.52 (d, J=2.4 Hz, 1H), 7.87 (dd, J=2.4, 8.8 Hz, 1H), 7.17 (d, J=8.8 Hz, 1H), 4.50 (t, J=5.4 Hz, 2H), 4.36 (q, J=7.1 Hz, 2H), 3.22 (t, J=7.3 Hz, 2H), 3.09-3.06 (m, 4H), 2.79 (s, 3H), 2.72 (t, J=5.4 Hz, 2H), 2.64-2.61 (m, 4H), 1.78-1.75 (m, 2H), 1.63 (t, J=7.1 Hz, 3H), 0.99 (t, J=7.3 Hz, 3H). LCMS (M+H)=577.7, purity~94.2%.

Example 60

(E)-2-(4-((4-ethoxy-3-(6-((hydroxyimino)methyl)-5-methyl-4-oxo-7-propyl-3,4-dihydropyrrolo[2,1-f][1,2,4]triazin-2-yl)phenyl)sulfonyl)piperazin-1-yl)ethyl nitrate (1a)

To a stirred solution of –2-(4-((4-ethoxy-3-(6-formyl-5-methyl-4-oxo-7-propyl-3,4-dihydropyrrolo[2,1-f][1,2,4]triazin-2-yl)phenyl)sulfonyl)piperazin-1-yl)ethyl nitrate (1ae) (100 mg, 0.173 mmol) in ethanol (2 mL) and water (0.5 mL), was added hydroxylamine hydrochloride (30.14 mg, 0.433 mmol) and the reaction mixture was heated to 85° C. for 8 h. On completion, the reaction mixture was concentrated under reduced pressure. The obtained residue was dissolved in water (5 mL) and extracted with ethyl acetate (2×15 mL). The combined organic layer was dried over anhydrous Na$_2$SO$_4$ and concentrated under reduced pressure. The obtained crude product was purified by reverse phase preparative HPLC using 0.1% formic acid in water and acetonitrile to afford the title compound 1ae (20 mg) as an off-white solid. $^1$H NMR (300 MHz, CD$_3$OD) δ=8.23 (s, 1H), 8.05 (d, J=1.8 Hz, 1H), 7.91 (dd, J=1.8, 8.8 Hz, 1H), 7.37 (d, J=8.8 Hz, 1H), 4.57 (t, J=5.3 Hz, 2H), 4.30 (q, J=6.9 Hz, 2H), 3.18-2.92 (m, 6H), 2.73 (t, J=5.3 Hz, 2H), 2.64-2.60 (m, 7H), 1.73-1.70 (m, 2H), 1.48 (t, J=6.9 Hz, 3H), 0.96 (t, J=7.5 Hz, 3H). LCMS (M+H)=592.4, purity~92.3%+1.3% (mixture of syn & anti isomers).

SCHEME 29

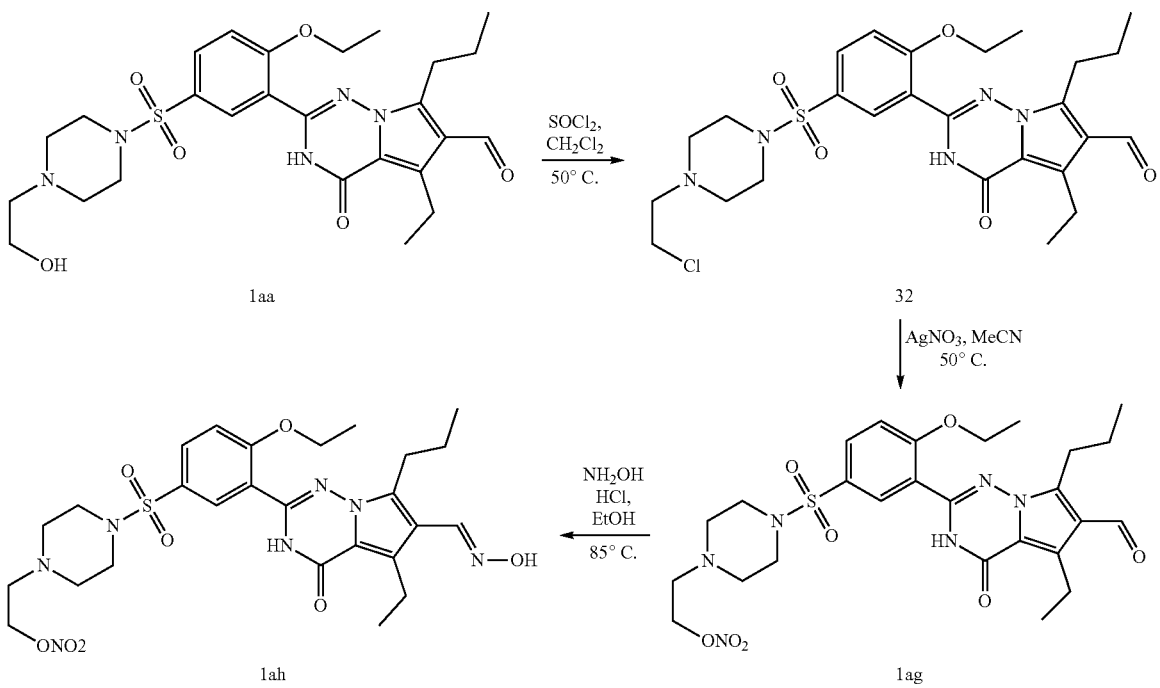

Example 61

2-(5-((4-(2-chloroethyl)piperazin-1-yl)sulfonyl)-2-ethoxyphenyl)-5-ethyl-4-oxo-7-propyl-3,4-dihydropyrrolo[2,1-f][1,2,4]triazine-6-carbaldehyde (32)

To a stirred solution of 2-(2-ethoxy-5-((4-(2-hydroxyethyl)piperazin-1-yl)sulfonyl)phenyl)-5-ethyl-4-oxo-7-propyl-3,4-dihydropyrrolo[2,1-f][1,2,4]triazine-6-carbaldehyde (1aa) (200 mg, 0.366 mmol) in dichloromethane (5 mL), was added SOCl$_2$ (0.053 mL, 0.733 mmol) at 0° C. The reaction mixture was heated to 50° C. and stirred for 12 h. On completion, the reaction mixture was concentrated under reduced pressure. The obtained residue was diluted with water (10 mL) and extracted with dichloromethane (2×15 mL). The combined organic layers were dried over anhydrous sodium sulfate and concentrated under reduced pressure to afford the title compound 32 (200 mg) as a brown solid, which was directly taken for next reaction without further purification. LCMS (M+H)=564.2, purity~86.6%.

Example 62

2-(4-((4-ethoxy-3-(5-ethyl-6-formyl-4-oxo-7-propyl-3,4-dihydropyrrolo[2,1-f][1,2,4]triazin-2-yl)phenyl)sulfonyl)piperazin-1-yl)ethyl nitrate (1ag)

To a stirred solution of 2-(5-((4-(2-chloroethyl)piperazin-1-yl)sulfonyl)-2-ethoxyphenyl)-5-ethyl-4-oxo-7-propyl-3,4-dihydropyrrolo[2,1-f][1,2,4]triazine-6-carbaldehyde (32) (200 mg, 0.355 mmol) in acetonitrile (5 mL), was added AgNO$_3$ (241 mg, 1.420 mmol) at RT. The reaction was then heated to 50° C. and stirred for 16 h. On completion, the reaction mixture was cooled to RT and filtered through a celite bed. The filtrate was concentrated under reduced pressure, diluted with water (15 mL) and extracted with ethyl acetate (2×20 mL). The combined organic layers were dried over anhydrous sodium sulfate and concentrated under reduced pressure. The crude product was purified by reverse phase preparative HPLC using 0.1% formic acid in water and acetonitrile to afford the title compound 1ag (30 mg) as a brown solid. $^1$H NMR (400 MHz, CDCl$_3$) δ=10.19 (s, 1H), 9.74 (br s, 1H; D$_2$O exchangeable), 8.53 (d, J=2.2 Hz, 1H), 7.87 (dd, J=2.2, 8.8 Hz, 1H), 7.18 (d, J=8.8 Hz, 1H), 4.51 (t, J=5.3 Hz, 2H), 4.37 (q, J=7.2 Hz, 2H), 3.35-3.18 (m, 4H), 3.09-3.06 (m, 4H), 2.73 (t, J=5.3 Hz, 2H), 2.63-2.61 (m, 4H), 1.78-1.75 (m, 2H), 1.63 (t, J=7.2 Hz, 3H), 1.30 (t, J=7.6 Hz, 3H), 1.00 (t, J=7.3 Hz, 3H). LCMS (M+H)=591.3, purity~96.5%.

Example 63

(E)-2-(4-((4-ethoxy-3-(5-ethyl-6-((hydroxyimino)methyl)-4-oxo-7-propyl-3,4-dihydropyrrolo[2,1-f][1,2,4]triazin-2-yl)phenyl)sulfonyl)piperazin-1-yl)ethyl nitrate (1ah)

To a stirred solution of –2-(4-((4-ethoxy-3-(5-ethyl-6-formyl-4-oxo-7-propyl-3,4-dihydropyrrolo[2,1-f][1,2,4]triazin-2-yl)phenyl)sulfonyl)piperazin-1-yl)ethyl nitrate (1ag) (90 mg, 0.152 mmol) in ethanol (3 mL) and water (0.5 mL), was added hydroxylamine hydrochloride (26.4 mg, 0.380 mmol) and the reaction mixture was heated to 85° C. for 16 h. On completion, the reaction mixture was concentrated under reduced pressure. The obtained residue was dissolved in water (5 mL) and extracted with ethyl acetate (2×15 mL). The combined organic layer was dried over anhydrous Na$_2$SO$_4$ and concentrated under reduced pressure. The obtained crude product was purified by reverse phase preparative HPLC using 0.1% formic acid in water and acetonitrile to afford the title compound 1ah (23 mg) as a brown solid. $^1$H NMR (300 MHz, CD$_3$OD) δ=8.22 (s, 1H), 8.05 (d, J=2.2 Hz, 1H), 7.91 (dd, J=2.2, 8.8 Hz, 1H), 7.37 (d, J=8.8 Hz, 1H), 4.57 (t, J=5.3 Hz, 2H), 4.31 (q, J=6.9 Hz, 2H), 3.20-2.92 (m, 8H), 2.73 (t, J=5.3 Hz, 2H), 2.63-2.61 (m, 4H), 1.73-1.70 (m, 2H), 1.49 (t, J=6.9 Hz, 3H), 1.22 (t, J=7.3 Hz, 3H), 0.96 (t, J=7.3 Hz, 3H). LCMS (M+H)=606.3, purity~92.3%+3.4% (mixture of syn & anti isomers).

SCHEME 30

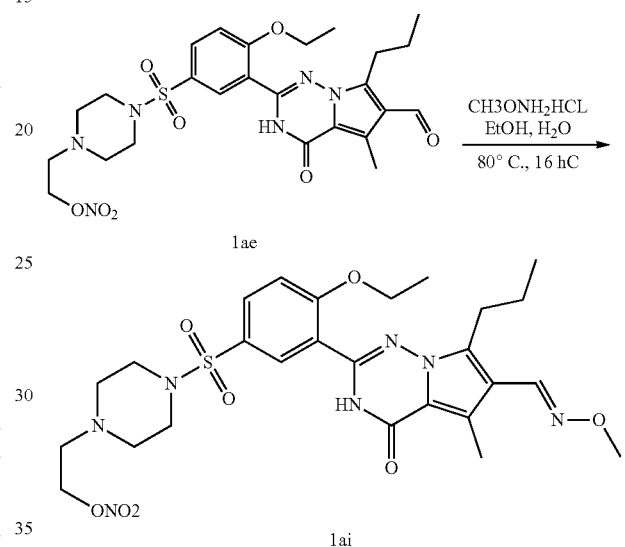

Example 64

(E)-2-(4-(4-ethoxy-3-(6-((methoxyimino)methyl)-5-methyl-4-oxo-7-popyl-3,4-dihydropyrrolo [1,2-f][1,2,4]triazin-2-yl)phenylsulfonyl)piperazin-1-yl)ethyl nitrate (1ai)

To a stirred solution of –2-(4-(4-ethoxy-3-(6-formyl-5-methyl-4-oxo-7-propyl-3,4-dihydropyrrolo[1,2-f][1,2,4]triazin-2-yl)phenylsulfonyl)piperazin-1-yl)ethyl nitrate (1ae) (90 mg, 0.164 mmol) in ethanol (5 mL) and water (0.5 mL), was added O-methoxylamine hydrochloride (34.4 mg, 0.412 mmol) and the reaction mixture was heated to 85° C. for 8 h. The reaction was monitored by LCMS. The reaction mixture was then cooled to room temperature and concentrated under reduced pressure. The obtained residue was dissolved in water (5 mL) and extracted with ethyl acetate (3×25 mL). The combined organic layer was dried over sodium sulphate and concentrated under reduced pressure. The crude LCMS analysis showed 45% of desired oxime along with 18% of chloro substituted oxime. The obtained crude product was dissolved in acetonitrile (10 mL), added AgNO$_3$ (80 mg) and stirred 50° C. for 12 h. The reaction mixture was then cooled to room temperature and concentrated under reduced pressure. The obtained residue was dissolved in water (5 mL) and extracted with ethyl acetate (3×25 mL).

The combined organic layer was dried over sodium sulphate and concentrated under reduced pressure. The crude product was purified by reverse phase preparative HPLC using 0.1% formic acid in water and acetonitrile to afford the title compound 1ai (18 mg) as an off-white solid. $^1$H NMR (400 MHz, CD$_3$OD): δ 8.24 (s, 1H), 8.04 (d, J=2.4 Hz, 1H), 7.91 (dd, J=2.4, 8.8 Hz, 1H), 7.37 (d, J=8.8 Hz, 1H), 4.56 (t, J=5.1 Hz, 2H), 4.34-4.24 (m, 2H), 3.91 (s, 3H), 3.17-2.94 (m, 6H), 2.77-2.68 (m, 2H), 2.67-2.49 (m, 7H), 1.70 (dd, J=7.3, 14.7 Hz, 2H), 1.48 (t, J=7.1 Hz, 3H), 0.95 (t, J=7.3 Hz, 3H); LCMS (ES): m/z 606.3 [M+H$^+$]; purity~95.1%+ 4.2% (mixture of anti & syn isomers).

SCHEME 31

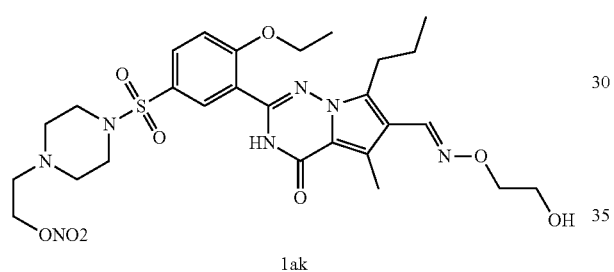

1ae

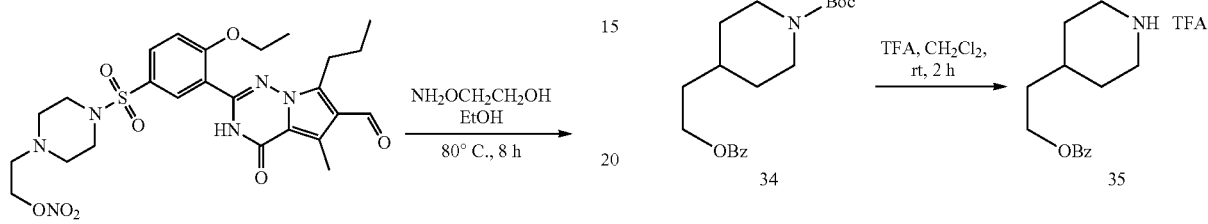

1ak

Example 65

(E)-2-(4-(4-ethoxy-3-(6-((2-hydroxyethoxyimino) methyl)-5-methyl-4-oxo-7-propyl-3,4-dihydropyr-rolo[1,2-f][1,2,4]triazin-2-yl)phenylsulfonyl)piper-azin-1-yl)ethyl nitrate (1ak)

To a stirred solution of –2-(4-(4-ethoxy-3-(6-formyl-5-methyl-4-oxo-7-propyl-3,4-dihydropyrrolo[1,2-f][1,2,4]tri-azin-2-yl)phenylsulfonyl)piperazin-1-yl)ethyl nitrate (1ae) (105 mg, 0.182 mmol) in ethanol (5 mL) was added 2-(ami-noxy)ethanol (35.13 mg, 0.455 mmol) at room temperature and stirred at 80° C. for 8 h. After completion of reaction (monitored by TLC), the reaction mixture was concentrated under reduced pressure. The obtained residue was purified by reverse phase preparative HPLC using 0.1% formic acid in water and acetonitrile to afford the title compound 1ak (28 mg) as a white solid. $^1$H NMR (400 MHz, CD$_3$OD): δ 8.28 (s, 1H), 8.03 (d, J=2.4 Hz, 1H), 7.90 (dd, J=2.4, 8.8 Hz, 1H), 7.37 (d, J=8.8 Hz, 1H), 4.57 (t, J=5.1 Hz, 2H), 4.29 (q, J=7.0 Hz, 2H), 4.20-4.17 (m, 2H), 3.83-3.81 (m, 2H), 3.03-3.01 (m, 6H), 2.74-2.71 (m, 2H), 2.61-2.59 (m, 6H), 1.72-1.68 (m, 2H), 1.43 (t, J=7.0 Hz, 3H), 0.95 (t, J=7.2 Hz, 3H); LCMS (ES): m/z 636.3 [M+H$^+$]; purity~94.4%+2.2% (mix-ture of anti & syn isomers).

SCHEME 32

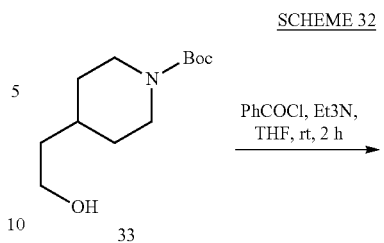

33

PhCOCl, Et3N,
THF, rt, 2 h
→

34 TFA, CH$_2$Cl$_2$, rt, 2 h → 35

Example 66 tert-butyl 4-(2-(benzoyloxy)ethyl)piperidine-1-car-boxylate (34)

To a stirred solution of tert-butyl 4-(2-hydroxyethyl) piperidine-1-carboxylate (33) (8.5 g, 37.06 mmol) in THF (160 mL), was added triethylamine (10.2 mL, 74.12 mmol) at room temperature. After 5 min, benzoyl chloride (4.73 mL, 40.77 mmol) was added dropwise at 0° C. under inert atmosphere. After addition, the resultant reaction mixture was stirred at room temperature for 2 h. After completion of reaction (monitored by TLC), the reaction was quenched with water (75 mL) and extracted with ethyl acetate (2×100 mL). The combined organic layer was dried over anhydrous sodium sulphate and concentrated under reduced pressure to afford 34 (10 g) as a brown liquid, which was directly taken for next reaction without further purification. $^1$H NMR (300 MHz, CDCl$_3$): δ 8.04 (d, J=7.3 Hz, 2H), 7.58-7.50 (m, 1H), 7.49-7.41 (m, 2H), 4.38 (t, J=6.6 Hz, 2H), 4.12-4.08 (m, 2H), 2.72-2.68 (m, 2H), 1.81-1.68 (m, 5H), 1.46 (s, 9H), 1.28-1.10 (m, 2H).

SCHEME 33

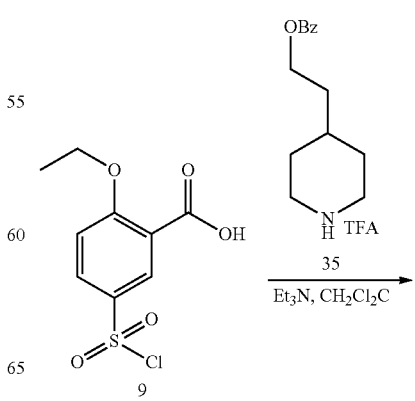

9

35

Et$_3$N, CH$_2$Cl$_2$C

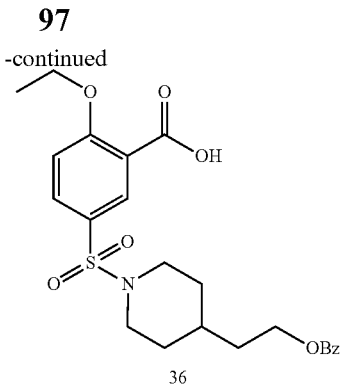

36

Example 67

2-(piperidin-4-yl)ethyl benzoate. TFA salt (35)

To a stirred solution of compound 34 (10 g) in $CH_2Cl_2$ (100 mL), was added trifluoroacetic acid (6.89 mL, 90.09 mmol) dropwise at 0° C. under inert atmosphere. After addition, the resultant reaction mixture was stirred at room temperature for 2 h. After completion of reaction (monitored by TLC), the reaction solution was concentrated under reduced pressure. The residue was co-distilled with $CH_2Cl_2$ (3×50 mL). The solid obtained was triturated with diethyl ether (50 mL), filtered and dried under vacuum to afford title 35 (4 g, 33% in two steps) as a brown solid. $^1$H NMR (400 MHz, DMSO-$d_6$): δ 8.93 (br s, 1H; $D_2O$ exchangeable), 8.85 (br s, 1H; $D_2O$ exchangeable), 8.01-7.92 (m, 2H), 7.72-7.62 (m, 1H), 7.59-7.48 (m, 2H), 4.34 (t, J=6.2 Hz, 2H), 3.23- 3.21 (m, 2H), 2.86-2.81 (m, 2H), 1.87 (br d, J=13.9 Hz, 2H), 1.81-1.63 (m, 3H), 1.43-1.26 (m, 2H); LCMS (ES): m/z 234.1 [M+H$^+$]; purity~99%.

Example 68

5-(4-(2-(benzoyloxy)ethyl)piperidin-1-ylsulfonyl)-2-ethoxybenzoic add (36)

To a stirred solution of 35 (4.07 g, 17.49 mmol) in $CH_2Cl_2$ (40 mL) was added triethylamine (11.10 mL, 79.54 mmol) at room temperature. After addition, a solution of 9 (4.2 g, 15.90 mmol) in $CH_2Cl_2$ (20 mL) was added dropwise at 0° C. under inert atmosphere. The resultant reaction mixture was stirred at room temperature for 12 h. After completion of reaction (monitored by TLC), the reaction mixture was concentrated and diluted with saturated $NaHCO_3$ solution (50 mL). The resultant solution was then neutralized with saturated citric acid solution (50 mL) and extracted with ethyl acetate (3×200 mL). The combined organic layer was dried over anhydrous sodium sulphate and concentrated under reduced pressure to afford Compound 36 (5.78 g, 78%) as a brown solid. $^1$H NMR (300 MHz, DMSO-$d_6$): δ 13.02 (br s, 1H; $D_2O$ exchangeable), 7.97-7.88 (m, 3H), 7.81 (dd, J=2.4, 8.8 Hz, 1H), 7.68-7.60 (m, 1H), 7.55-7.46 (m, 2H), 7.33 (d, J=8.8 Hz, 1H), 4.27 (t, J=6.4 Hz, 2H), 4.20 (q, J=7.0 Hz, 2H), 3.61 (br d, J=11.7 Hz, 2H), 2.20 (br t, J=10.8 Hz, 2H), 1.79 (br d, J=11.7 Hz, 2H), 1.63 (q, J=6.4 Hz, 2H), 1.46-1 41 (m, 1H), 1.35 (t, J=7.0 Hz, 3H), 1.30-1.17 (m, 2H); LCMS (ES): m/z 462.2 [M+H$^+$]; purity~95%.

SCHEME 34

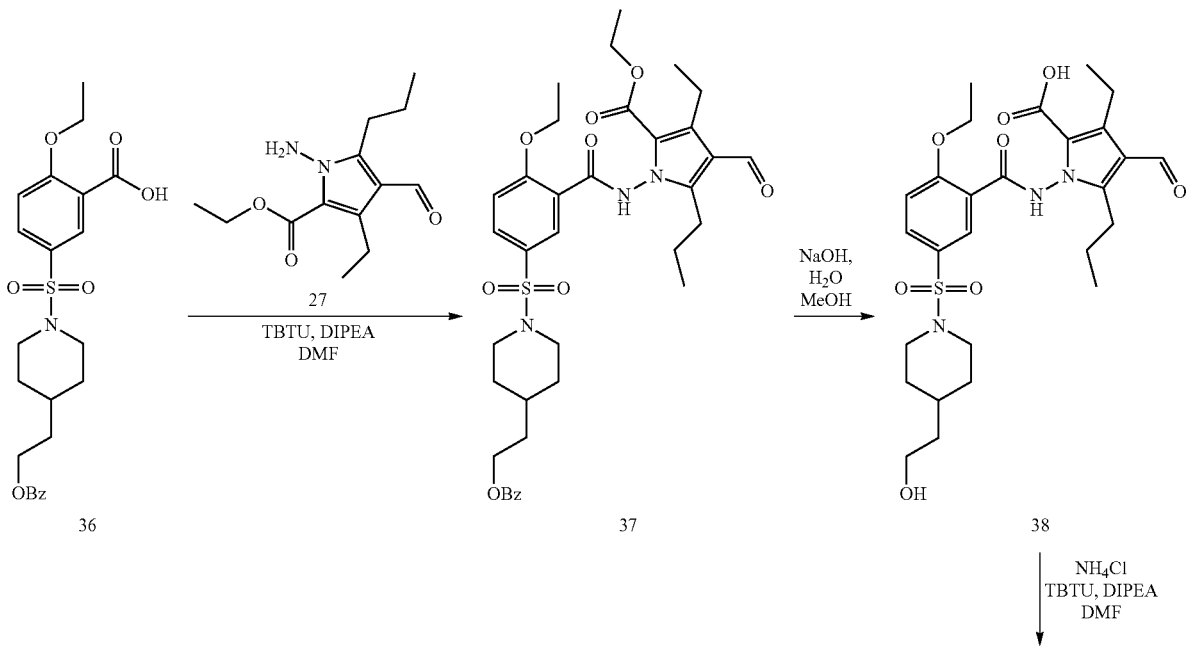

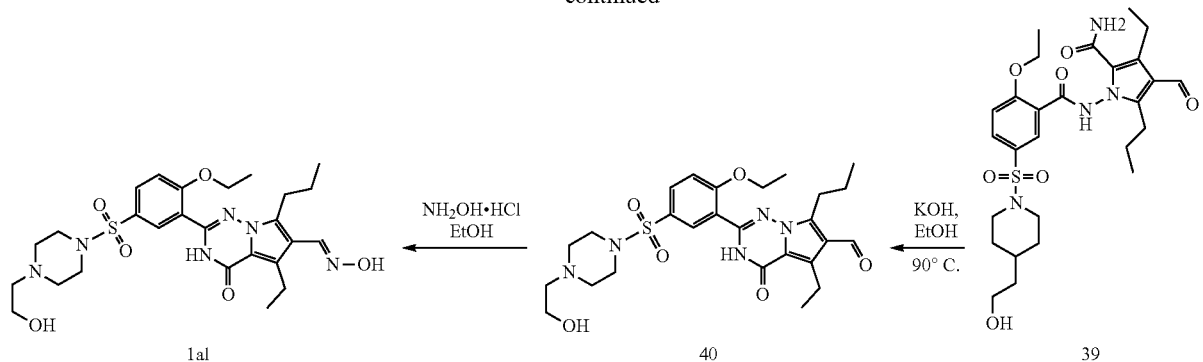

Example 69

Ethyl 1-(5-(4-(2-(benzoyloxy)ethyl)piperidin-1-ylsulfonyl)-2-ethoxybenzamido)-4-formyl-3-methyl-5-propyl-1H-pyrrole-2-carboxylate (37)

To a stirred solution of −5-(4-(2-(benzoyloxy)ethyl)piperidin-1-ylsulfonyl)-2-ethoxybenzoic acid (36) (4.2 g, 9.11 mmol) in DMF (30 mL), was added TBTU (5.85 g, 18.22 mmol) and diisopropylethyl amine (4.7 mL, 27.33 mmol) at room temperature and stirred for 20 min. To this, ethyl 1-amino-4-formyl-3-methyl-5-propyl-1H-pyrrole-2-carboxylate (27) (2.168 g, 9.11 mmol) was added and stirred the reaction mixture at room temperature for 16 h. After completion of reaction (monitored by TLC), the reaction was quenched with ice-cold water (100 mL) and extracted with ethyl acetate (3×300 mL). The combined organic layer was dried over anhydrous sodium sulphate and concentrated under reduced pressure. The crude product was purified by silica gel column chromatography using 10-50% ethyl acetate gradient in petroleum ether to afford the title compound 37 (3.0 g, 48%) as a white solid. $^1$H NMR (300 MHz, CDCl$_3$): δ 10.38 (s, 1H), 10.07 (s, 1H), 8.56 (d, J=2.2 Hz, 1H), 7.99 (d, J=7.3 Hz, 2H), 7.93 (dd, J=2.4, 8.6 Hz, 1H), 7.59-7.50 (m, 1H), 7.48-7.36 (m, 2H), 7.17 (d, J=8.8 Hz, 1H), 4.41 (q, J=7.0 Hz, 2H), 4.33 (t, J=6.4 Hz, 2H), 4.28-4.13 (m, 2H), 3.81 (br d, J=10.8 Hz, 2H), 2.61 (s, 3H), 2.30 (br t, J=10.8 Hz, 2H), 1.84-1.81 (m, 2H), 1.76-1.52 (m, 9H), 1.47-1.33 (m, 3H), 1.27 (t, J=7.0 Hz, 3H), 0.95 (t, J=7.3 Hz, 3H); LCMS (ES): m/z 682.3 [M+H$^+$]; purity~98%.

Example 70

1-(2-ethoxy-5-(4-(2-hydroxyethyl)piperidin-1-ylsulfonyl)benzamido)-4-formyl-3-methyl-5-propyl-1H-pyrrole-2-carboxylic acid (38)

To a stirred solution of 37 (3.1 g, 4.55 mmol) in methanol (15 mL) and water (15 mL), was added NaOH (3.1 g, w/w) at room temperature. The reaction mixture was heated to 65° C. and stirred for 16 h. After completion of reaction (monitored by TLC), methanol was concentrated under reduced pressure. The obtained aqueous reaction solution was neutralized (pH-7) with aqueous 1N HCl solution (10 mL). The solid precipitated was filtered and dried under vacuum to afford 38 (2.6 g, 87%) as an off-white solid. $^1$H NMR (300 MHz, DMSO-d$_6$): δ 12.89 (s, 1H; D$_2$O exchangeable), 11.45 (br s, 1H; D$_2$O exchangeable), 7.90 (d, J=2.2 Hz, 1H), 7.83 (dd, J=2.2, 8.8 Hz, 1H), 7.39 (d, J=8.8 Hz, 1H), 4.42 (br s, 1H; D$_2$O exchangeable), 4.26 (q, J=7.0 Hz, 2H), 3.60 (br d, J=11.4 Hz, 2H), 3.43-3.37 (m, 2H), 2.86-2.83 (m, 2H), 2.54 (s, 3H), 2.19 (br t, J=10.8 Hz, 2H), 1.71 (br d, J=11.7 Hz, 2H), 1.64-1.51 (m, 2H), 1.40 (t, J=7.0 Hz, 3H), 1.36-1.26 (m, 3H), 1.25-1.03 (m, 3H), 0.90 (t, J=7.3 Hz, 3H); LCMS (ES): m/z 550.3 [M+H$^+$]; purity~94%.

Example 71

1-(2-ethoxy-5-(4-(2-hydroxyethyl)piperidin-1-ylsulfonyl)benzamido)-4-formyl-3-methyl-5-propyl-1H-pyrrole-2-carboxamide (39)

To a stirred solution of 38 (2.4 g, 4.37 mmol) in DMF (25 mL), TBTU (2.80 g, 8.74 mmol) and diisopropylethylamine (2.3 mL, 13.11 mmol) were added and stirred at room temperature for 20 minutes. To this, ammonium chloride (468 mg, 8.74 mmol) was added and the reaction mixture was stirred at room temperature for 16 h. After completion of reaction (monitored by TLC), the reaction was quenched with ice-cold water (75 mL) and extracted with 5% methanol in CH$_2$Cl$_2$ (2×100 mL). The combined organic layer was dried over anhydrous sodium sulphate and concentrated under reduced pressure. The obtained crude product was purified by silica gel column chromatography using 2-8% gradient methanol in dichloromethane as eluent to afford the title compound 39 (2 g, 83%) as a pale yellow solid. $^1$H NMR (300 MHz, DMSO-d$_6$): δ 11.36 (s, 1H; D$_2$O exchangeable), 9.96 (s, 1H), 7.88 (d, J=2.6 Hz, 1H), 7.86-7.81 (m, 1H), 7.48 (br s, 1H; D$_2$O exchangeable), 7.39 (br d, J=8.8 Hz, 1H), 7.31 (br s, 1H; D$_2$O exchangeable), 4.35-4.19 (m, 2H+OH), 3.67-3.53 (m, 2H), 3.43-3.34 (m, 2H), 2.93-2.72 (m, 2H), 2.41 (s, 3H), 2.31-2.13 (m, 2H), 1.72 (br d, J=11.7 Hz, 2H), 1.62-1.50 (m, 2H), 1.40 (t, J=7.0 Hz, 3H), 1.36-1.21 (m, 5H), 0.89 (t, J=7.2 Hz, 3H); LCMS (ES): m/z 549.3 [M+H$^+$]; purity~91%.

Example 72

2-(2-ethoxy-5-(4-(2-hydroxyethyl)piperidin-1-ylsulfonyl)phenyl)-5-methyl-4-oxo-7-propyl-3,4-dihydropyrrolo[1,2-f][1,2,4]triazine-6-carbaldehyde (40)

To a stirred solution of 39 (400 mg, 0.72 mmol) in absolute ethanol (6 mL) was added 1M aqueous KOH solution (5 mL) and stirred at 100° C. in a sealed tube for 96 h. The reaction mixture was concentrated completely under reduced pressure. The obtained residue was diluted with water (5 mL) and stirred at room temperature for 10 min. The solid precipitated was filtered and dried to afford the title compound 40 (280 mg, 72%) as a brown solid. $^1$H NMR (400 MHz, CDCl$_3$): δ 10.19 (s, 1H), 9.68 (br s, 1H; D$_2$O exchangeable), 8.53 (d, J=2.0 Hz, 1H), 7.89 (dd, J=2.4, 8.8 Hz, 1H), 7.16 (d, J=8.8 Hz, 1H), 4.36 (q, J=6.8 Hz, 2H), 3.81 (br d, J=11.7 Hz, 2H), 3.68-3.64 (m, 2H), 3.22 (t, J=7.3 Hz, 2H), 2.79 (s, 3H), 2.40-2.27 (m, 2H), 1.81-1.72 (m, 4H), 1.62 (t, J=6.8 Hz, 3H), 1.52-1.47 (m, 3H), 1.42-1.33 (m, 3H), 0.99 (t, J=7.3 Hz, 3H); LCMS (ES): m/z 531.3 [M+H$^+$]; purity~92%.

Example 73

(E)-2-(2-ethoxy-5-(4-(2-hydroxyethyl)piperidin-1-ylsulfonyl)phenyl)-5-methyl-4-oxo-7-propyl-3,4-dihydropyrrolo[1,2-f][1,2,4]triazine-6-carbaldehyde oxime (1al)

To a stirred solution of compound 40 (140 mg, 0.264 mmol) in ethanol (3 mL) and water (0.5 mL), was added hydroxylamine hydrochloride (45.88 mg, 0.66 mmol) and the reaction mixture was heated to 90° C. for 16 h. After completion of reaction (monitored by TLC), the reaction mixture was concentrated under reduced pressure. The obtained residue was dissolved in water (5 mL) and extracted with ethyl acetate (3×25 mL). The combined organic layer was dried over anhydrous Na$_2$SO$_4$ and concentrated under reduced pressure.

The obtained crude product was purified by reverse phase preparative HPLC using 0.1% formic acid in water and acetonitrile to afford the title compound 1al (80 mg, 55%) as an off-white solid. $^1$H NMR (300 MHz, DMSO-d$_6$) δ 11.55 (br s, 1H; D$_2$O exchangeable), 10.95 (s, 1H; D$_2$O exchangeable), 8.21 (s, 1H), 7.92-7.79 (m, 2H), 7.37 (d, J=8.3 Hz, 1H), 4.31 (t, J=5.1 Hz, 1H; D$_2$O exchangeable), 4.21 (q, J=6.8 Hz, 2H), 3.60 (br d, J=11.2 Hz, 2H), 3.39 (q, J=5.9 Hz, 2H), 2.94 (br t, J=7.6 Hz, 2H), 2.55 (s, 3H), 2.24 (br t, J=11.0 Hz, 2H), 1.76-1.52 (m, 4H), 1.39-1.26 (m, 6H), 1.24-1.09 (m, 2H), 0.88 (t, J=7.3 Hz, 3H); LCMS (ES): m/z 546.3 [M+H$^+$]; purity~95.5%.

SCHEME 35

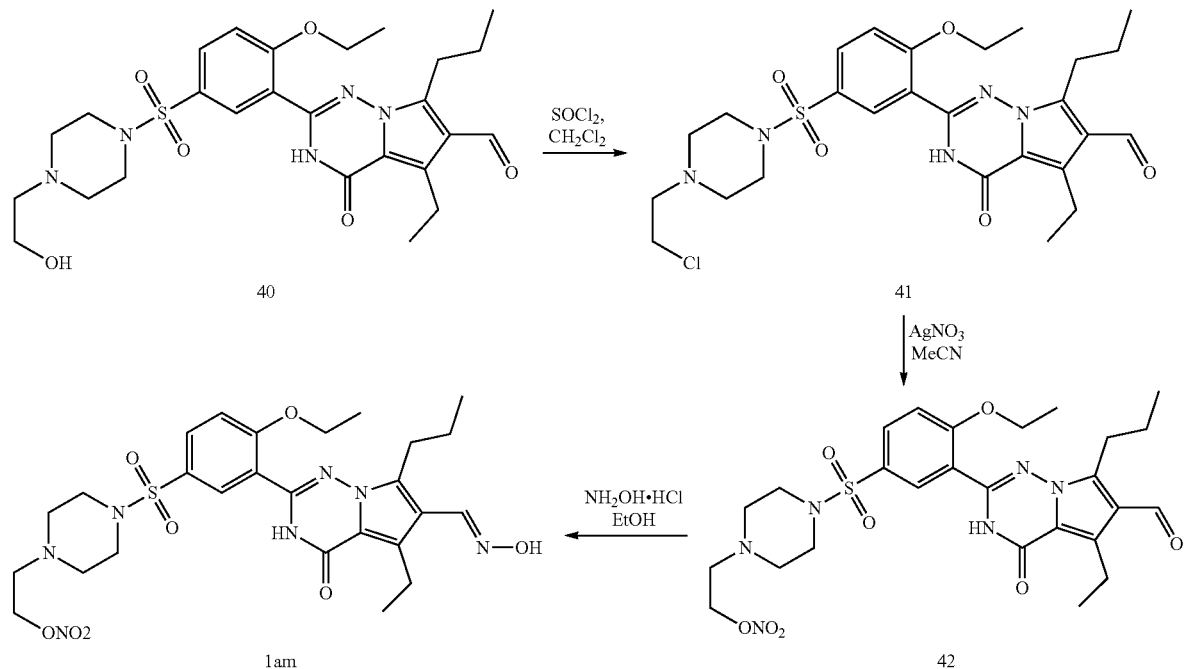

Example 74

2-(5-(4-(2-chloroethyl)piperidin-1-ylsulfonyl)-2-ethoxyphenyl)-5-methyl-4-oxo-7-propyl-3,4-dihydropyrrolo[1,2-f][1,2,4]triazine-6-carbaldehyde (41)

To a stirred solution of 2-(2-ethoxy-5-(4-(2-hydroxyethyl) piperidin-1-ylsulfonyl)phenyl)-5-methyl-4-oxo-7-propyl-3,4-dihydropyrrolo[1,2-f][1,2,4]triazine-6-carbaldehyde (40) (100 mg, 0.188 mmol) in dichloromethane (5 mL), was added SOCl$_2$ (0.06 mL, 0.943 mmol) at room temperature. The reaction mixture was heated to 50° C. and stirred for 72 h. TLC showed product formation along with unreacted 40. The reaction mixture was cooled to room temperature, added SOCl$_2$ (0.12 mL, 1.88 mmol) and the reaction mixture was stirred at 80° C. for additional 48 h. The reaction mixture was then cooled to room temperature and concentrated under reduced pressure. The obtained residue was diluted with water (10 mL) and extracted with dichloromethane (2×20 mL). The combined organic layer was dried over anhydrous sodium sulphate and concentrated under reduced pressure to afford the crude compound 41.

The reaction was repeated on 150 mg scale and both the crude materials were combined and purified by reverse phase purification by Grace instrument to afford the title compound 41 (120 mg) as an off-white solid. $^1$H NMR (300 MHz, CDCl$_3$): δ 10.19 (s, 1H), 9.71 (s, 1H; D$_2$O exchangeable), 8.53 (d, J=2.2 Hz, 1H), 7.89 (dd, J=2.2, 8.8 Hz, 1H), 7.16 (d, J=8.8 Hz, 1H), 4.36 (q, J=7.0 Hz, 2H), 3.84 (br d, J=11.7 Hz, 2H), 3.54 (t, J=6.4 Hz, 2H), 3.22 (br t, J=7.3 Hz, 2H), 2.79 (s, 3H), 2.33 (br t, J=11.4 Hz, 2H), 1.86-1.66 (m, 6H), 1.62 (t, J=7.0 Hz, 3H), 1.45-1.26 (m, 3H), 1.00 (t, J=7.3 Hz, 3H); LCMS (ES): m/z 549.3 [M+H⁺]; purity~90%.

Example 75

2-(1-(4-ethoxy-3-(6-formyl-5-methyl-4-oxo-7-propyl-3,4-dihydropyrrolo[1,2-1][1,2,4]triazin-2-yl)phenylsulfonyl)piperidin-4-yl)ethyl nitrate (42)

To a stirred solution of 41 (140 mg, 0.255 mmol) in acetonitrile (5 mL), was added AgNO₃ (173.5 mg, 1.02 mmol) at room temperature. The reaction was then heated to 60° C. and stirred for 48 h. TLC showed product formation along with unreacted 41. The reaction mixture was cooled to room temperature, added AgNO₃ (260 mg, 1.53 mmol) and the reaction mixture was stirred at 60° C. for additional 48 h. The reaction mixture was then cooled to room temperature and filtered though a celite bed. The filtrate was concentrated under reduced pressure, diluted with water (15 mL) and extracted with ethyl acetate (2×40 mL). The combined organic layers were dried over anhydrous sodium sulphate and concentrated under reduced pressure. The crude product was purified by silica gel purification by Grace instrument (20-50% gradient ethylacetate in petroleum ether as an eluent) to afford the title compound 42 (56 mg) as a pale yellow solid. ¹H NMR (400 MHz, CDCl₃): δ 10.19 (s, 1H), 9.73 (br s, 1H; D₂O exchangeable), 8.52 (d, J=2.2 Hz, 1H), 7.88 (dd, J=2.2, 8.8 Hz, 1H), 7.17 (d, J=8.8 Hz, 1H), 4.46 (t, J=6.2 Hz, 2H), 4.36 (q, J=7.0 Hz, 2H), 3.84 (br d, J=11.0 Hz, 2H), 3.22 (br t, J=7.3 Hz, 2H), 2.79 (s, 3H), 2.44-2.23 (m, 2H), 1.84-1.66 (m, 6H), 1.62 (t, J=7.0 Hz, 3H), 1.44-1.41 (m, 3H), 0.99 (t, J=7.3 Hz, 3H); LCMS (M+H)=m/z 576.3 [M+H⁺]; purity~91.4%.

Example 76

(E)-2-(1-(4-ethoxy-3-(6-((hydroxyimino)methyl)-5-methyl-4-oxo-7-propyl-3,4-dihydro pyrrolo[1,2-f][1,2,4]triazin-2-yl)phenylsulfonyl)piperidin-4-yl)ethyl nitrate (1am)

To a stirred solution of 42 (100 mg, 0.173 mmol) in ethanol (3 mL) and water (0.5 mL), was added hydroxylamine hydrochloride (30.2 mg, 0.434 mmol) and the reaction mixture was heated to 90° C. for 16 h. After completion of reaction (monitored by TLC), the reaction mixture was concentrated under reduced pressure. The obtained residue was dissolved in water (5 mL) and extracted with ethyl acetate (2×15 mL). The combined organic layer was dried over anhydrous Na₂SO₄ and concentrated under reduced pressure. The obtained crude product was purified by reverse phase preparative HPLC using 0.1% formic acid in water and acetonitrile to afford the title compound 1am (56 mg) as a brown solid. ¹H NMR (300 MHz, DMSO-d₆): δ 11.54 (s, 1H; D₂O exchangeable), 10.95 (s, 1H; D₂O exchangeable), 8.21 (s, 1H), 7.95-7.79 (m, 2H), 7.37 (d, J=8.8 Hz, 1H), 4.52 (br t, J=6.6 Hz, 2H), 4.21 (q, J=6.8 Hz, 2H), 3.63 (br d, J=12.2 Hz, 2H), 2.94 (br t, =7.3 Hz, 2H), 2.55 (s, 3H), 2.25 (br t, J=11.0 Hz, 2H), 1.74 (br d, J=10.8 Hz, 2H), 1.67-1.53 (m, 4H), 1.35-1.30 (m, 4H), 1.27-1.13 (m, 2H), 0.87 (t, J=7.3 Hz, 3H); LCMS (M+H)=m/z 591.3 [M+H⁺]; purity~97.3%.

SCHEME 36

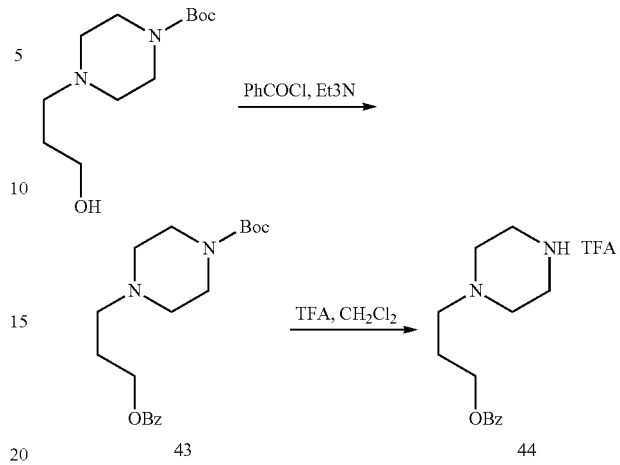

Example 77 tert-butyl 4-(3-(benzoyloxy)propyl)piperazine-1-carboxylate (43)

To a stirred solution of tert-butyl 4-(3-hydroxypropyl)piperazine-1-carboxylate (7.0 g, 28.64 mmol) in THF (50 mL), was added triethylamine (8 mL, 57.29 mmol) at room temperature. After 5 min, benzoyl chloride (3.66 mL, 31.51 mmol) was added dropwise at 0° C. under inert atmosphere. After addition, the resultant reaction mixture was stirred at room temperature for 1 h. After completion of reaction (monitored by TLC), the reaction was quenched with water (100 mL) and extracted with ethyl acetate (3×250 mL). The combined organic layer was dried over anhydrous sodium sulphate and concentrated under reduced pressure to afford 43 (7.8 g) as a off-white solid. ¹H NMR (400 MHz, CDCl₃): δ 8.06-8.00 (m, 2H), 7.59-7.52 (m, 1H), 7.48-7.40 (m, 2H), 4.38 (t, J=6.6 Hz, 2H), 3.50-3.39 (m, 4H), 2.53 (t, J=7.3 Hz, 2H), 2.43 (br t, J=4.9 Hz, 4H), 1.98 (quin, J=6.8 Hz, 2H), 1.46 (s, 9H); LCMS (M+H)=m/z 349.7 [M+H⁺]; purity~83%.

Example 78

3-(piperazin-1-yl)propyl benzoate TFA salt (44)

To a stirred solution of compound 43 (7.8 g) in CH₂Cl₂ (80 mL), was added trifluoroacetic acid (10.3 mL, 134.48 mmol) dropwise at 0° C. under inert atmosphere. After addition, the resultant reaction mixture was stirred at room temperature for 8 h. After completion of reaction (monitored by TLC), the reaction solution was concentrated under reduced pressure. The residue was co-distilled with CH₂Cl₂ (3×100 mL). The solid obtained was triturated with diethyl ether (50 mL), filtered and dried under vacuum to afford title 44 (8.6 g) as a white solid. ¹H NMR (300 MHz, DMSO-d₆): δ 9.13 (br s, 2H), 8.07-7.95 (m, 2H), 7.73-7.64 (m, 1H), 7.60-7.47 (m, 2H), 4.34 (t, J=6.2 Hz, 2H), 3.40-2.94 (m, 10H), 2.16-1.96 (m, 2H); LCMS (M+H)=m/z 249.2 [M+H⁺]; purity~98%.

SCHEME 37

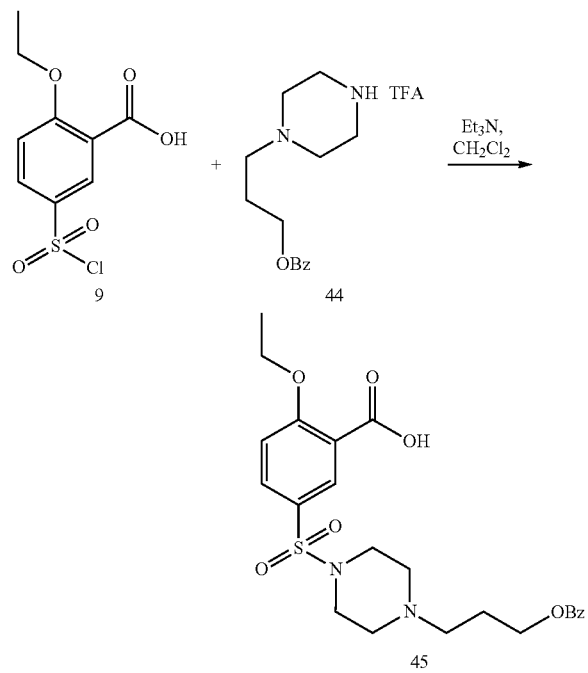

Example 79

5-(4-(3-(benzoyloxy)propyl)piperazin-1-ylsulfonyl)-2-ethoxybenzoic acid (45)

To a stirred solution of Compound 44 (8.3 g, 31.43 mmol) in CH$_2$Cl$_2$ (60 mL) was added triethylamine (26.5 mL, 188.63 mmol) at room temperature. After addition, a solution of 9 (8.57 g, 34.58 mmol) in CH$_2$Cl$_2$ (40 mL) was added dropwise at 0° C. under inert atmosphere. The resultant reaction mixture was stirred at room temperature for 16 h.

After completion of reaction (monitored by TLC), the reaction mixture was concentrated and diluted with saturated NaHCO$_3$ solution (50 mL). The resultant solution was washed with ethyl acetate (100 mL). The aqueous solution was then neutralized with saturated citric acid solution (100 mL) and extracted with ethyl acetate (3×300 mL). The combined organic layer was dried over anhydrous sodium sulphate and concentrated under reduced pressure to afford the title 45 (9.1 g, 60%) as a white solid. $^1$H NMR (400 MHz, CDCl$_3$): δ 12.17 (br s, 1H), 8.35 (d, J=2.4 Hz, 1H), 7.99 (d, J=7.3 Hz, 2H), 7.86 (dd, J=2.4, 8.8 Hz, 1H), 7.61-7.51 (m, 1H), 7.47-7.36 (m, 2H), 7.12 (d, J=8.8 Hz, 1H), 4.43-4.26 (m, 4H), 3.21 (br s, 4H), 2.92 (br s, 4H), 2.86-2.78 (m, 2H), 2.15-2.05 (m, 2H), 1.55 (t, J=6.8 Hz, 3H); LCMS (ES): m/z 477.2 [M+H$^+$]; purity~97%.

SCHEME 38

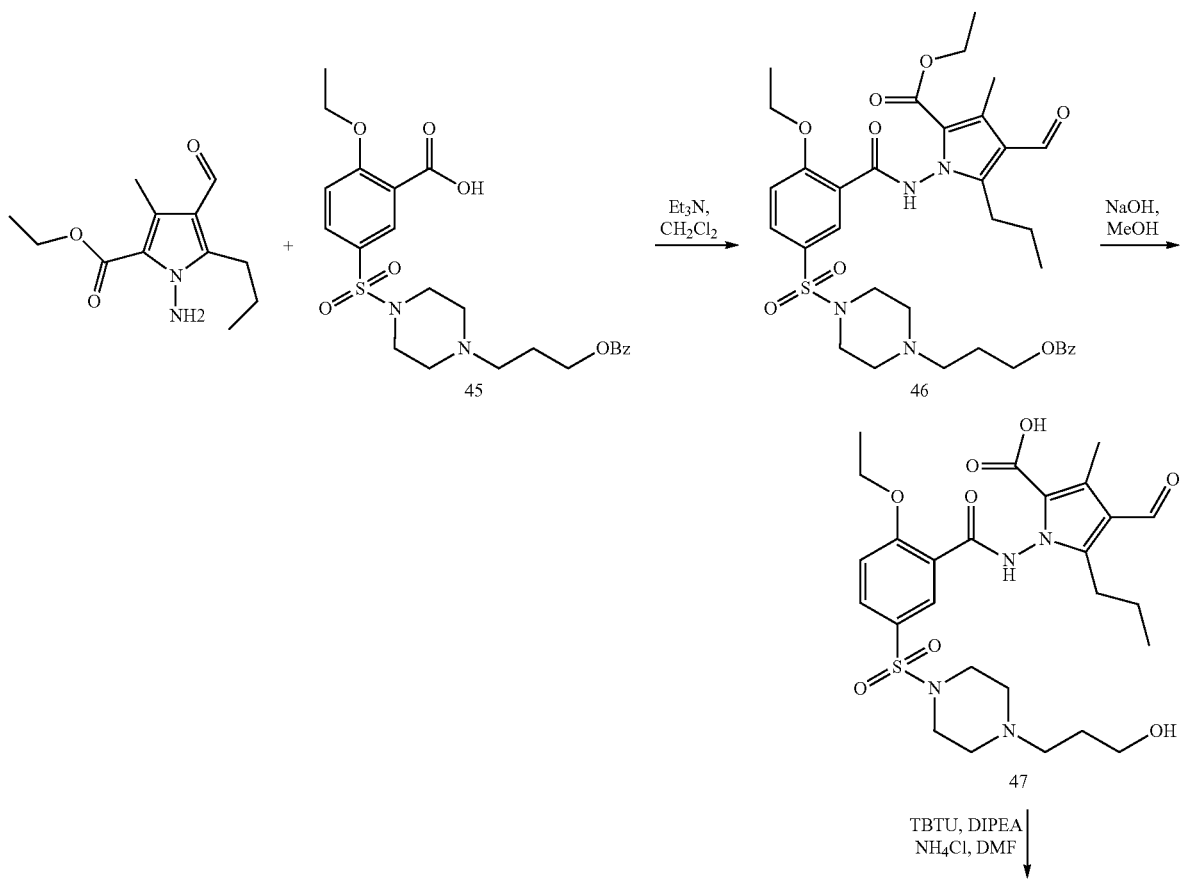

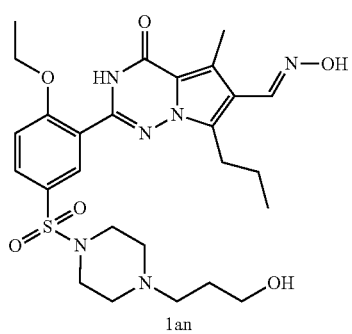 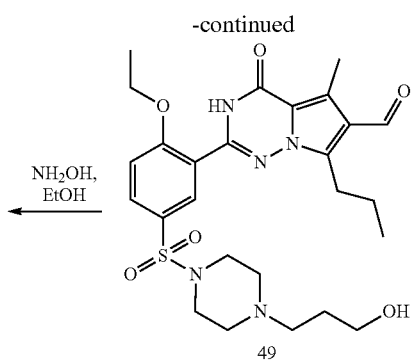 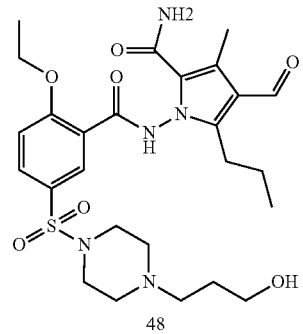

1an  49  48

-continued

NH₂OH, EtOH ← KOH, EtOH ←

Example 80

Ethyl 1-(5-(4-(3-(benzoyloxy)propyl)piperazin-1-ylsulfonyl)-2-ethoxybenzamido)-4-formyl-3-methyl-5-propyl-1H-pyrrole-2-carboxylate (46)

To a stirred solution of 5-(4-(3-(benzoyloxy)propyl)piperazin-1-ylsulfonyl)-2-ethoxybenzoic acid (45) (5.0 g, 10.50 mmol) in DMF (30 mL), was added TBTU (6.74 g, 21.0 mmol) and diisopropylethyl amine (5.5 mL, 31.5 mmol) at room temperature and stirred for 20 min. To this, ethyl 1-amino-4-formyl-3-methyl-5-propyl-1H-pyrrole-2-carboxylate (14) (2.50 g, 10.5 mmol) was added and stirred the reaction mixture at room temperature for 16 h. After completion of reaction (monitored by TLC), the reaction was quenched with ice-cold water (100 mL) and extracted with ethyl acetate (3×250 mL). The combined organic layer was dried over anhydrous sodium sulphate and concentrated under reduced pressure. The crude product was purified by silica gel column chromatography using 30-50% ethyl acetate gradient in petroleum ether to afford the title compound 46 (4.8 g, 65%) as a brown liquid. $^1$H NMR (300 MHz, CDCl$_3$): δ 10.43 (s, 1H; D$_2$O exchangeable), 10.07 (s, 1H), 8.57 (s, 1H), 7.99 (br d, J=7.7 Hz, 2H), 7.92 (br d, J=8.8 Hz, 1H), 7.64-7.50 (m, 1H), 7.49-7.36 (m, 2H), 7.19 (d, J=8.8 Hz, 1H), 4.43 (q, J=6.6 Hz, 2H), 4.31 (br t, J=6.4 Hz, 2H), 4.23 (br d, J=5.5 Hz, 2H), 3.04 (br s, 4H), 2.61 (s, 3H), 2.58-2.43 (m, 6H), 1.89 (td, J=6.6, 13.2 Hz, 2H), 1.73-1.57 (m, 5H), 1.33-1.20 (m, 5H), 0.96 (t, J=7.3 Hz, 3H); LCMS (ES): m/z 697.9 [M+H$^+$]; purity~89%.

Example 81

1-(2-ethoxy-5-(4-(3-hydroxypropyl)piperazin-1-ylsulfonyl)benzamido)-4-formyl-3-methyl-5-propyl-1H-pyrrole-2-carboxylic acid (47)

To a stirred solution of 46 (2.8 g, 4.021 mmol) in methanol (30 mL) and water (30 mL), was added NaOH (2.8 g, w/w) at room temperature. The reaction mixture was heated to 65° C. and stirred for 12 h. After completion of reaction (monitored by TLC), methanol was concentrated under reduced pressure. The obtained aqueous reaction solution was neutralized (pH-7) using aqueous 1N HCl solution (15 mL). The solid precipitated was filtered and dried under vacuum to afford 47 (1.875 g, 82%) as an off-white solid. $^1$H NMR (300 MHz, DMSO-d$_6$): δ 11.63 (br s, 1H), 9.98 (s, 1H), 7.90 (d, J=2.2 Hz, 1H), 7.83 (dd, J=2.2, 8.8 Hz, 1H), 7.40 (d, J=8.8 Hz, 1H), 4.27 (q, J=6.8 Hz, 2H), 3.36 (br t, J=6.2 Hz, 2H+OH), 2.88 (br s, 6H), 2.54 (s, 3H), 2.43 (br s, 4H), 2.31 (br t, J=7.2 Hz, 2H), 1.65-1.46 (m, 4H), 1.40 (t, J=7.0 Hz, 3H), 0.90 (t, J=7.3 Hz, 3H); LCMS (ES): m/z 565.8 [M+H$^+$]; purity~96%.

Example 82

1-(2-ethoxy-5-(4-(3-hydroxypropyl)piperazin-1-ylsulfonyl)benzamido)-4-formyl-3-methyl-5-propyl-1H-pyrrole-2-carboxamide (48)

To a stirred solution of 47 (1.875 g, 3.32 mmol) in DMF (15 mL), TBTU (2.135 g, 6.64 mmol) and diisopropylethylamine (1.7 mL, 9.97 mmol) were added and stirred at room temperature for 20 minutes. To this, ammonium chloride (356 mg, 6.64 mmol) was added and the reaction mixture was stirred at room temperature for 16 h. After completion of reaction (monitored by TLC), the reaction was quenched with water (50 mL) and extracted with ethyl acetate (3×75 mL). The combined organic layer was dried over anhydrous sodium sulphate and concentrated under reduced pressure. The obtained crude product was purified by silica gel column chromatography using 4-8% gradient methanol in dichloromethane as an eluent to afford the title compound 48 (1.4 g, 74%) as a brown solid. $^1$H NMR (400 MHz, CDCl$_3$): δ 10.61 (s, 1H; D$_2$O exchangeable), 10.05 (s, 1H), 8.51 (d, J=2.4 Hz, 1H), 7.89 (dd, J=2.4, 8.8 Hz, 1H), 7.17 (d, J=8.8 Hz, 1H), 5.66 (br s, 2H; D$_2$O exchangeable), 4.42 (q, J=7.2 Hz, 2H), 3.73 (t, J=5.1 Hz, 2H), 3.06-3.02 (m, 4H), 2.64-2.60 (m, 6H), 2.57 (s, 3H), 1.74-1.61 (m, 7H), 0.97 (t, J=7.3 Hz, 3H); LCMS (ES): m/z 564.3 [M+H$^+$]; purity~95%.

Example 83

2-(2-ethoxy-5-(4-(3-hydroxypropyl)piperazin-1-ylsulfonyl)phenyl)-5-methyl-4-oxo-7-propyl-3,4-dihydropyrrolo[1,2-f][1,2,4]triazine-6-carbaldehyde (49)

To a stirred solution of 48 (500 mg, 0.88 mmol) in absolute ethanol (8 mL) was added 1M aqueous KOH solution (8 mL) and stirred at 100° C. in a sealed tube for 96 h. The reaction mixture was concentrated completely under reduced pressure. The obtained residue was diluted with water (10 mL); the solid precipitated was filtered and dried to afford the title compound 49 (350 mg, 72%) as a pale yellow solid. $^1$H NMR (300 MHz, CDCl$_3$): δ 10.18 (s, 1H), 8.47 (br s, 1H), 7.83 (d, J=8.8 Hz, 1H), 7.15 (d, J=8.8 Hz, 1H), 4.37-4.33 (m, 3H), 3.73-3.70 (m, 2H), 3.21 (br t, J=7.2 Hz, 2H), 3.07-3.03 (m, 4H), 2.78 (s, 3H), 2.63-2.58 (m, 6H), 1.89-1.50 (m, 7H), 0.99 (t, J=7.3 Hz, 3H); LCMS (ES): m/z 546.7 [M+H$^+$]; purity~91%.

Example 84

(E)-2-(2-ethoxy-5-(4-(3-hydroxypropyl)piperazin-1-ylsulfonyl)phenyl)-5-methyl-4-oxo-7-propyl-3,4-dihydropyrrolo[1,2-f][1,2,4]triazine-6-carbaldehyde oxime (1an)

To a stirred solution of 49 (150 mg, 0.275 mmol) in ethanol (5 mL) and water (0.5 mL), was added hydroxylamine hydrochloride (47.8 mg, 0.68 mmol) and the reaction mixture was heated to 90° C. for 16 h. After completion of reaction (monitored by TLC), the reaction mixture was concentrated under reduced pressure. The obtained residue was dissolved in water (5 mL) and extracted 10% methanol in dichloromethane solution (3×25 mL). The combined organic layer was dried over anhydrous $Na_2SO_4$ and concentrated under reduced pressure. The obtained crude product was purified by reverse phase preparative HPLC using 0.1% formic acid in water and acetonitrile to afford the title compound 1an (62 mg, 40%) as an off-white solid. $^1$H NMR (400 MHz, DMSO-$d_6$): δ 11.56 (br s, 1H; $D_2O$ exchangeable), 10.95 (br s, 1H; $D_2O$ exchangeable), 8.21 (s, 1H), 7.91-7.80 (m, 2H), 7.39 (d, J=8.8 Hz, 1H), 4.34 (br s, 1H; $D_2O$ exchangeable), 4.22 (q, J=7.0 Hz, 2H), 3.38-3.34 (m, 2H), 3.00-2.81 (m, 6H), 2.55 (s, 3H), 2.43-2.40 (m, 4H), 2.35-2.27 (m, 2H), 1.62-1.58 (m, 2H), 1.54-1.45 (m, 2H), 1.34 (t, J=7.0 Hz, 3H), 0.87 (t, J=7.3 Hz, 3H); LCMS (ES): m/z 561.4 [M+H$^+$]; purity~95%.

SCHEME 39

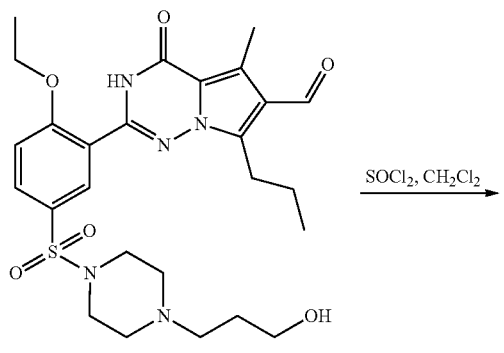

SOCl$_2$, CH$_2$Cl$_2$

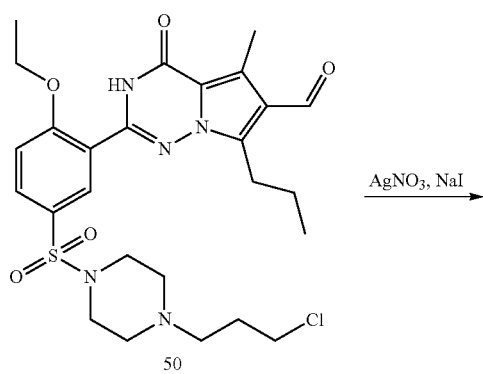

AgNO$_3$, NaI

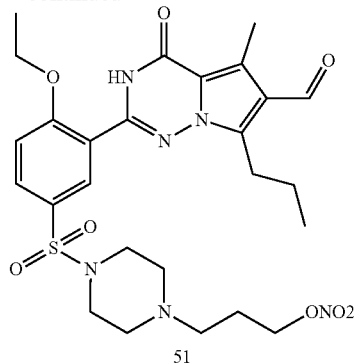

NH$_2$OH, EtOH

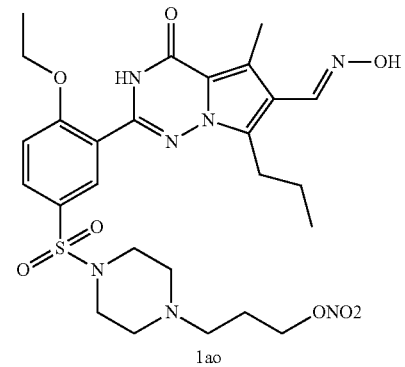

1ao

Example 85

2-(5-(4-(3-chloropropyl)piperazin-1-ylsulfonyl)-2-ethoxyphenyl)-5-methyl-4-oxo-7-propyl-3,4-dihydropyrrolo[1,2-f][1,2,4]triazine-6-carbaldehyde (50)

To a stirred solution of –2-(2-ethoxy-5-(4-(3-hydroxypropyl)piperazin-1-ylsulfonyl)phenyl)-5-methyl-4-oxo-7-propyl-3,4-dihydropyrrolo[1,2-f][1,2,4]triazine-6-carbaldehyde (49) (200 mg, 0.366 mmol) in dichloromethane (10 mL), was added SOCl$_2$ (0.1 mL, 1.83 mmol) at room temperature. The reaction mixture was heated to 70° C. and stirred for 12 h. After completion of reaction (monitored by TLC), the reaction mixture was cooled to room temperature and concentrated under reduced pressure. The obtained residue was diluted with water (10 mL) and extracted with dichloromethane (2×25 mL).

The combined organic layer was dried over anhydrous sodium sulphate and concentrated under reduced pressure to afford the crude compound 50 (235 mg) as a brown solid, which was directly taken for next reaction without further purification. $^1$H NMR (300 MHz, CDCl$_3$): δ 9.64 (s, 1H), 8.48 (d, J=2.0 Hz, 1H), 7.84 (d, J=2.0, 8.8 Hz, 1H), 7.16 (d, J=8.8 Hz, 1H), 4.34 (q, J=6.8 Hz, 2H), 3.58-3.55 (m, 2H), 3.27-2.97 (m, 7H), 2.75 (s, 3H), 2.58-2.54 (m, 4H), 1.82-1.72 (m, 2H), 1.67-1.53 (m, 6H), 1.02 (t, J=7.3 Hz, 3H); LCMS (M+H)=m/z 564.3 [M+H$^+$]; purity~94%.

Example 86

3-(4-(4-ethoxy-3-(6-formyl-5-methyl-4-oxo-7-propyl-3,4-dihydropyrrolo[1,2-1][1,2,4]triazin-2-yl)phenylsulfonyl)piperazin-1-yl)propyl nitrate (51)

To a stirred solution of 8 (220 mg) in DMF (3 mL), AgNO$_3$ (266 mg, 1.56 mmol) and NaI (58.5 mg, 0.39 mmol) were added at room temperature. The reaction was then heated to 60° C. and stirred for 48 h. The reaction mixture was then cooled to room temperature, diluted with water (15 mL) and extracted with ethyl acetate (3×50 mL). The combined organic layers were dried over anhydrous sodium sulphate and concentrated under reduced pressure to afford the crude compound 50.

Note: The same reaction was performed in two batches (100 mg+200 mg) and the obtained crude materials were combined and purified by reverse phase preparative HPLC using 0.1% formic acid in water and acetonitrile to afford the title compound 9 (52 mg) as a brown solid. LCMS (M+H)=m/z 591.4 [M+H$^+$]; purity~97%.

Example 87

(E)-3-(4-(4-ethoxy-3-(6-((hydroxyimino)methyl)-5-methyl-4-oxo-7-propyl-3,4-dihydropyrrolo[1,2-f][1,2,4]triazin-2-yl)phenylsulfonyl)piperazin-1-yl)propyl nitrate (1ao)

To a stirred solution of 51 (50 mg, 0.084 mmol) in ethanol (2 mL) and water (0.5 mL), was added hydroxylamine hydrochloride (15 mg, 0.211 mmol) and the reaction mixture was heated to 90° C. for 12 h. After completion of reaction (monitored by TLC), the reaction mixture was concentrated under reduced pressure. The obtained residue was dissolved in water (2 mL) and extracted with 5% methanol in dichloromethane (3×25 mL). The combined organic layer was dried over anhydrous Na$_2$SO$_4$ and concentrated under reduced pressure. The obtained crude product was purified by reverse phase preparative HPLC using 0.1% formic acid in water and acetonitrile to afford the title compound 1ao (10 mg) as a white solid. $^1$H NMR (400 MHz, DMSO-d$_6$): δ 11.56 (br s, 1H; D$_2$O exchangeable), 10.95 (s, 1H; D$_2$O exchangeable), 8.21 (s, 1H), 7.93-7.78 (m, 2H), 7.39 (br d, J=8.8 Hz, 1H), 4.48 (br t, J=6.6 Hz, 2H), 4.29-4.15 (m, 2H), 3.14-2.77 (m, 6H), 2.55 (s, 3H), 2.47-2.20 (m, 6H), 1.86-1.70 (m, 2H), 1.59 (td, J=7.3, 14.7 Hz, 2H), 1.35 (t, J=7.1 Hz, 3H), 0.87 (t, J=7.3 Hz, 3H); LCMS (M+H)=m/z 606.4 [M+H$^+$]; purity~95.8%.

SCHEME 40

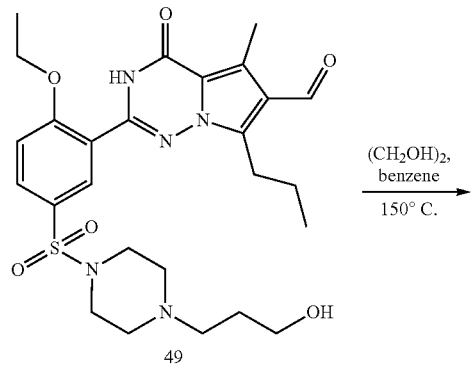

49

(CH$_2$OH)$_2$, benzene
150° C.

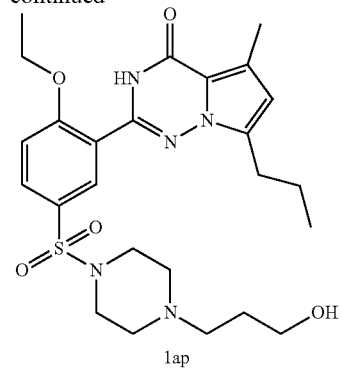

1ap

Example 88

2-(2-ethoxy-5-((4-(3-hydroxypropyl)piperazin-1-yl)sulfonyl)phenyl)-5-methyl-7-propylpyrrolo [2,1-][1,2,4]triazin-4(3H)-one (1ap)

In a reaction tube, 2-(2-ethoxy-5-((4-(3-hydroxypropyl)piperazin-1-yl)sulfonyl) phenyl)-5-methyl-4-oxo-7-propyl-3,4-dihydropyrrolo [2,1-j][1,2,4]triazine-6-carbaldehyde (49) (150 mg, 0.275 mmol), benzene (2.5 mL) and ethylene glycol (2.5 mL) were charged and stirred for 5 min. To this, pTSA.H$_2$O (75 mg, 0.399 mmol) was added and capped the reaction tube. The reaction mixture was dipped in a preheated oil bath at 140° C. and stirred for 16 h. After completion of reaction (monitored by TLC and LCMS analysis), the reaction mixture was cooled to room temperature and diluted with water (20 mL). The resultant solution was extracted with ethyl acetate (2×15 mL). The combined organic layer was dried over anhydrous Na$_2$SO$_4$ and concentrated under reduced pressure. The obtained crude product was purified by reverse phase preparative HPLC using 0.1% formic acid in water and acetonitrile to afford 1ap (50 mg) as a white solid. $^1$H NMR (400 MHz, CDCl$_3$) δ=9.49 (br s, 1H; D$_2$O exchangeable), 8.50 (d, J=2.4 Hz, 1H), 7.80 (dd, J=2.4, 8.8 Hz, 1H), 7.14 (d, J=8.8 Hz, 1H), 6.17 (s, 1H), 4.34 (q, J=7.0 Hz, 2H), 4.26 (br s, 1H; D$_2$O exchangeable), 3.72 (t, J=5.1 Hz, 2H), 3.07 (br s, 4H), 2.85 (t, J=7.6 Hz, 2H), 2.75-2.58 (m, 6H), 2.54 (s, 3H), 1.84-1.65 (m, 4H), 1.61 (t, J=7.0 Hz, 3H), 1.01 (t, J=7.6 Hz, 3H); LCMS (ESI)=m/z 518.27, purity~95.44%.

SCHEME 41

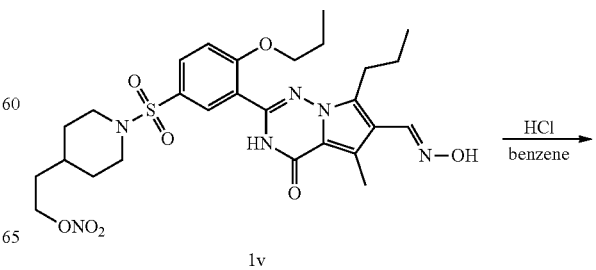

1v

HCl
benzene

-continued

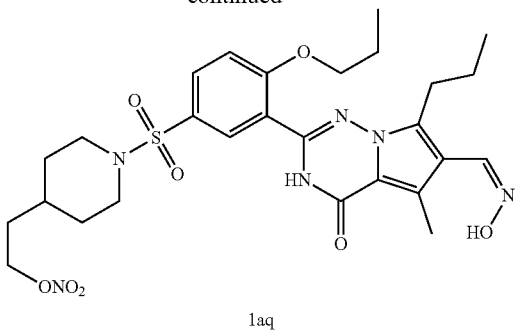

1aq

Example 89

(Z)-2-(1-((3-(6-((hydroxyimino)methyl)-5-methyl-4-oxo-7-propyl-3,4-dihydropyrrolo[2,1-f][1,2,4]triazin-2-yl)-4-propoxyphenyl)sulfonyl)piperidin-4-yl) ethyl nitrate (1aq)

1v (100 mg; 0.164 mmol) was dissolved in benzene (2 mL) at reflux temperature under argon atmosphere. The reaction was then cooled to −50° C. and purged with dry HCl gas until the precipitation started to form (~5 min). After the precipitation was observed, the reaction was cooled to 0° C. and stirred for 15 min. The solid was filtered, washed with benzene (0.5 mL), petroleum ether (0.5 mL) and dried under vacuum. The solid was taken in diethyl ether (8 mL) and added pre-cooled 2.6 M aqueous NaOH solution (~1.0 mL) at 0° C. until the solid was completely dissolved. Saturated $NH_4Cl$ solution (~2.0 mL) was added to it until the precipitate forms and within 1 min, went back in to the solution. The diethyl ether layer was separated and the aqueous layer was extracted with diethyl ether (2×8 mL). The combined organic layer was dried over anhydrous $Na_2SO_4$ and concentrated under vacuum to afford the crude product with LCMS-66% purity. The product was purified by reverse phase Prep HPLC (XBridge $C_{18}$ column; 10 mM aqueous ammonium bicarbonate solution with acetonitrile) to afford 1aq (17.5 mg) as an off-white solid. $^1$H NMR (400 MHz, DMSO-d4) S 11.38 (s, 1H; $D_2O$ exchangeable), 11.18 (br s, 1H, $D_2O$ exchangeable), 7.90-7.78 (m, 2H), 7.51 (s, 1H), 7.36 (br d, J=9.3 Hz, 1H), 4.52 (br t, J=6.6 Hz, 2H), 4.11 (t, J=6.4 Hz, 2H), 3.64-3.61 (m, 2H), 2.89-2.77 (m, 2H), 2.41 (s, 3H), 2.28-2.23 (m, 2H), 1.82-1.66 (m, 4H), 1.65-1.51 (m, 4H), 1.38-1.31 (m, 1H), 1.25-1.19 (m, 2H), 0.94 (t, J=7.3 Hz, 3H), 0.83 (t, J=7.3 Hz, 3H); LCMS (ES): m/z 605.5 [M+H$^+$]; purity~95%.

Example 90

PDE5 assay Purpose: Evaluation of the effects of compounds of the present invention on the activity of the human phosphodiesterase-5 quantified by measuring the formation of 5'GMP from cGMP using PDE5 enzyme isolated from human platelets. The latter was effected in accordance with the method as described by Masaaki I, Nishikawa M, Fujioka M, Miyahara M, Isaka N, Shiku H, Nakano T, Cell Signal (1996), 8(8):575-581.

Experimental protocol: The test compound, i.e the compound of the present invention, reference compound or water (control) are added to a buffer containing 40 mM Tris/HCl (pH 7.8), 3 mM $MgCl_2$, 1.4 mM DTT, 0.21% BSA, 200 mM $NH_4Cl$, 1 µM cGMP and 0.1 µCi [3H]cGMP. Thereafter, the reaction is initiated by addition of the enzyme and the mixture is incubated for 60 min at 22° C.

For basal control measurements, the enzyme is omitted from the reaction mixture. Following incubation SPA beads are added. After 20 min at 22° C. under shaking, the amount of [3H]5'GMP is quantified with a scintillation counter (Topcount, Packard).

The results shown in Table 1 are expressed as a percent inhibition of the control enzyme activity.

The standard inhibitory reference compound is dipyridamole, which is tested in each experiment at several concentrations to obtain an inhibition curve from which its $IC_{50}$ value is calculated.

As shown in Table 1, the compounds of the present invention are potent and selective inhibitors of human cGMP-specific PDE5.

TABLE 1

| Compound | % inhibition at 5.0 E-09 M | IC50 |
|---|---|---|
| sildenafil | 49.9 | $5.4 \times 10^{-9}$ M |
| 1a | 77.6 | $2.5 \times 10^{-10}$ M |
| 1b | 34.0 | $1.2 \times 10^{-8}$ M |
| 1k | 24.5 | |
| 1n | 33.0 | |
| 1o | 83.0 | $5.3 \times 10^{-10}$ M |
| 1r | 74.0 | $1.6 \times 10^{-10}$ M |
| 1s | 46.0 | |
| 1t | 44.9 | |
| 1u | 50.3 | $1.5 \times 10^{-9}$ M |
| 1y | 45.9 | $4.1 \times 10^{-9}$ M |
| 1w | 75.5 | |
| 1y | 6.4 | |
| 1z | 87.0 | |
| 1ab | 86.8 | |
| 1ac | 12.4 | |
| 1ad | 50.5 | |
| 1ae | 44.6 | |
| 1af | 74.5 | |
| 1ag | 18.7 | |
| 1ah | 69.7 | |
| 1ai | 0.3 | |
| 1ak | 8.3 | |
| 1al | 84.9 | $4.8 \times 10^{-10}$ M |
| 1am | 25.1 | $6.6 \times 10^{-8}$ M |
| 1an | 84.9 | $4.2 \times 10^{-10}$ M |
| 1ao | 70.6 | $1.2 \times 10^{-8}$ M |
| 1ap | 69.2 | $2.8 \times 10^{-9}$ M |
| 1aq | 1.3 | |

Example 91

Measurements of cGMP in Human Pulmonary Artery Smooth Muscle Cells (hPASMC)

Human Pulmonary Artery Smooth Muscle Cells (hPASMC) were purchased from Clonetics' Lonza (Lonza, reference number CC-2581) and cultured in Clonetics™ smooth muscle growth medium (Clonetics™ SmGM™-2 with BulletKit™ growth factor supplements (Lonza, reference number CC-3182) at 37° C. in 5% $C_{O2}$. Culture medium was replaced each 48 hours. Cells were grown in 75 cm$^2$ culture plates.

48 h before the experiments, cells were trypsinized (Trypsin kit One ReagentPack™ (CC-5034), Lonza) and plated in 96 well plates precoated with collagen I at 10000 cells per well. 24 h before the experiments culture medium was replaced by serum-reduced (0.5% FBS) medium.

Immediately before the experiments, medium was exchanged and hPASMC incubated in presence of the inventive compound 1v (in concentrations of $1\times10^{-12}$ M (1 pM)-$1\times10^{-7}$ M (100 nM)), the inventive compound 1r (in concentrations of $1\times10^{-16}$ M (0.1 fM)-$1\times10^{-7}$ M (100 nM)), the reference PDE5 inhibitor sildenafil (in concentrations of $1\times10^{-10}$ M (0.1 nM)-$1\times10^{-7}$ M (100 nM)) or vehicle (0.1% DMSO) over 15 or 30 min.

Figure 1B:
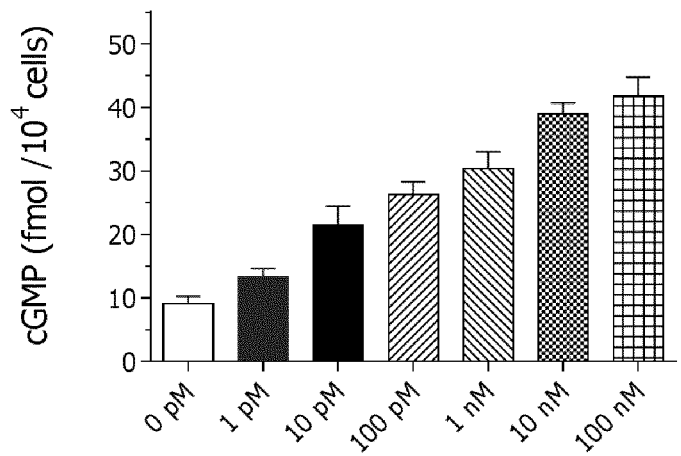
Figure 1C:
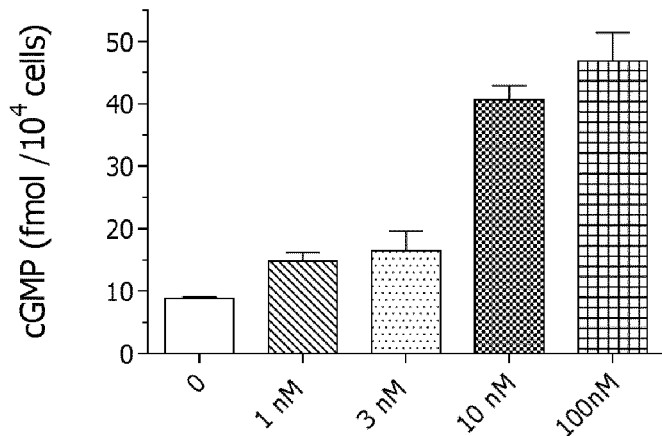

Measurements of intracellular cGMP were performed using the Amersham cGMP EIA System (GE Healthcare, RPN226) following the instructions of the manufacturer. The assay has a sensitivity of 2 fmol cGMP per well. Briefly, incubations were terminated by adding Amersham's lysis buffer 1 and cells left for 10 min under agitation to ensure complete lysis. cGMP in samples was then acetylated using triethylamine and acetic anhydride and determined by a competitive ELISA. The ELISA is based on the competition between acetylated cGMP in cell culture lysates and a peroxidase-labelled cGMP conjugate for limited binding sites on a cGMP specific antiserum immobilized on pre-coated 96 well MTP. cGMP was determined based on a standard curve. Results were expressed as fmol cGMP in $10^4$ cells as means+/−SE from 3 independent experiments in triplicates (FIG. 1A, FIG. 1B, FIG. 1C). Surprisingly, the inventive compounds 1v and 1r, and in particular 1r, show a significantly higher activity as compared to the reference inhibitor sildenafil.

Example 92

Isometric Tension Studies on Rat Aortic Rings

Animals

A total of 131 male 11-week-old Sprague-Dawley rats from Harland (Barcelona) were used. The study was in line with the Guide for the Care and Use of Laboratory Animals (1996). After 1 week of acclimatization, rats were anesthetized. Appropriate depth of anesthesia was determined by the absence of the leg flexor response and the eyelid reflex. Then, the thorax was quickly opened by a midline incision, and the rat was sacrificed by cutting the heart and exsanguination. The aorta was quickly removed without damaging the endothelium and placed in a beaker filled with Krebs's solution and bubbled with 95% O2/5% CO2.

Preparation of the Isolated Organs
Rat Aortic Rings: Intact Endothelium

In brief, 3- to 4-mm thoracic aortic rings were mounted in separate 5-ml organ baths containing Krebs solution with (mM) NaCl 118.0, KCl 4.7, CaCl2) 1.9, KH2PO4 1.2, MgSO4 1.2, NaHCO3 25.0 and glucose 5.0 and maintained at 37° C. and bubbled with 95% O2/5% CO2 (Klein T, Eltze M, Grebe T, Hatzelmann A, Kbmhoff M (2007). Celecoxib dilates guinea-pig coronaries and rat aortic rings and amplifies NO/cGMP signaling by PDE5 inhibition. Cardiovasc Res 75: 390-7). Indomethacin (1 µM) was added to the saline solution.

The tissues were attached to force displacement transducers, stretched to a resting tension of 1-1.5 g. Next, the endothelial integrity of the preparations was determined by verifying the responsiveness to acetylcholine (ACh, 1 µM) in vessels precontracted with phenylephrine (PE, 300 nM, corresponding to 80-90% of its maximum effect). When the relaxation by 1 µM ACh of the tension achieved with 300 nM PE was more than 60%, the preparation was eligible. Eligible rings were then washed several times to restore tension to the baseline level. After this procedure, the preparations were allowed to equilibrate for 60 min before contraction to a new single concentration of phenylephrine (300 nM).

Rat Aortic Rings: Mechanically Removed Endothelium

In some experiments, the entire length of the thoracic aorta was functionally denuded of the endothelial layer by gently scraping the luminal surface with a 1.5 mm glass rod. The tissues were attached to force displacement transducers, stretched to a resting tension of 1-1.5 g. Next, the absence of the endothelium was confirmed by verifying an impaired responsiveness to acetylcholine (1 µM) in vessels precontracted with PE (300 nM). Rings were then washed several times to restore tension to the baseline level. After this response the preparations were allowed to equilibrate for 60 min before contraction to a new single concentration of phenylephrine (300 nM; EC80-90 of its own maximal effect).

Rat Aortic Rings: Endothelial Dysfunction Secondary to High Glucose

In brief, 3- to 4-mm thoracic aortic rings were mounted in separate 5-ml organ baths containing Krebs' solution with (mM) NaCl 118.0, KCl 4.7, CaCl2) 1.9, KH2PO4 1.2, MgSO4 1.2, NaHCO3 25.0 and glucose 5.0, maintained at 37° C. and bubbled with 95% O2/5% CO2 [1]. Indomethacin (1 µM) was added to the saline solution. The tissues were attached to force displacement transducers, stretched to a resting tension of 1-1.5 g. Next, the endothelial integrity of the preparations was determined by verifying the responsiveness to acetylcholine (1 µM) in vessels precontracted with PE (300 nM). Only vessels with at least 60% relaxation to 1 µM ACh from the tension with 300 nM were eligible. Eligible rings were washed and equilibrated several times to restore tension to the baseline level with Krebs solution with (mM) NaCl 118.0, KCl 4.7, CaCl2) 1.9, KH2PO4 1.2, MgSO4 1.2, NaHCO3 25.0 and glucose 25.0 and maintained at 37° C., 95% O2/5% CO2. The preparations were allowed to equilibrate for 60 min in Krebs with high glucose (25 mM) before contraction to a new single concentration of PE (300 nM). The experimental protocol was a previously described (Dhar I, Dhar A, Wu L, Desai K (2012). Arginine attenuates methylglyoxal- and high glucose-induced endothelial dysfunction and oxidative stress by an endothelial nitric-oxide synthase-independent mechanism. J Pharmacol Exp Ther 342: 196-204) with modifications.

Design—Concentration Dependent Relaxation Curves—Cumulative Protocol

In the first set of experiments, concentration-response curves (1 µM-1 µM) for Sildenafil (reference), 1r, or 1v were constructed in endothelium-intact or -denuded preparations, in the presence of N-nitro-L-arginine methyl ester (L-NAME 100 µM) or in Krebs with High Glucose (25 mM). When the influence of NG-nitro-L-arginine methyl ester (L-NAME) on the relaxation induced by test and reference compounds (Sildenafil, 1r or 1v) was evaluated, L-NAME was added to the preparations 30 min prior to PE. On the plateau of PE induced tension the compounds (sildenafil, 1r or 1v) were cumulatively added (30 min per concentration) to the bath until maximum relaxation was achieved. Finally, sodium nitroprusside (0.1 mM) was added, in order to obtain maximum relaxation of arterial rings.

The amount of relaxation (percent values as means±SEM) was quantified as percent relaxation from the tension (plateau) achieved with phenylephrine.

Drugs

Compounds were dissolved in DMSO (100%) at 10 mM concentrations and stored in aliquots at −20° C. Dilutions were performed immediately before each experiment and the DMSO concentration kept at 0.1% in all incubations.

Analysis of Results

Data are presented as mean±SEM. Statistical analysis of results has been performed by analysis of variance (ANOVA) either parametric or non-parametric (Kruskal-Wallis), followed by Bonferroni test or Dunn tests as appropriate (GraphPad Software Inc, San Diego, CA, USA). Significance was accepted when P<0.05. Non-linear regression was conducted with GraphPad Software). Results are related to Vehicle control (0.1% DMSO) for each measurement point.

RESULTS

Figure 2A:
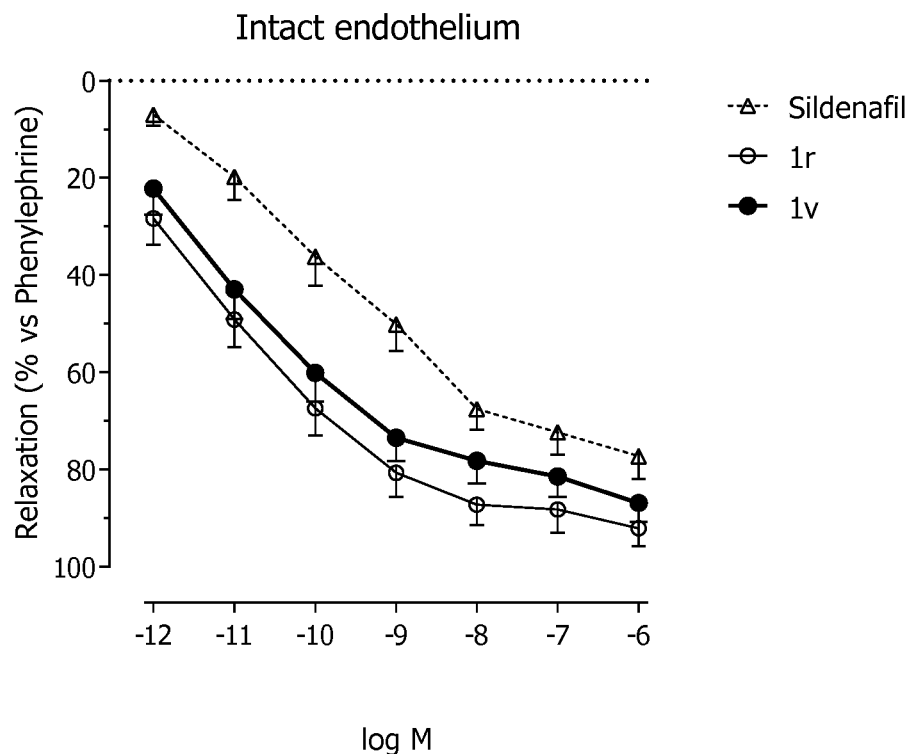
FIGS. 2A-2D: Concentration dependent relaxation by 1v, 1r, sildenafil of phenylephrine-precontracted rat aortic rings with intact endothelium (FIG. 2A), exposed to 25 mM glucose for 1 h (FIG. 2B), in presence of L-NAME (100 μM) (FIG. 2C), following mechanical removal of intact endothelium (FIG. 2D). Results are depicted as the means f SEM from 16-20 preparations.
Figure 2B:
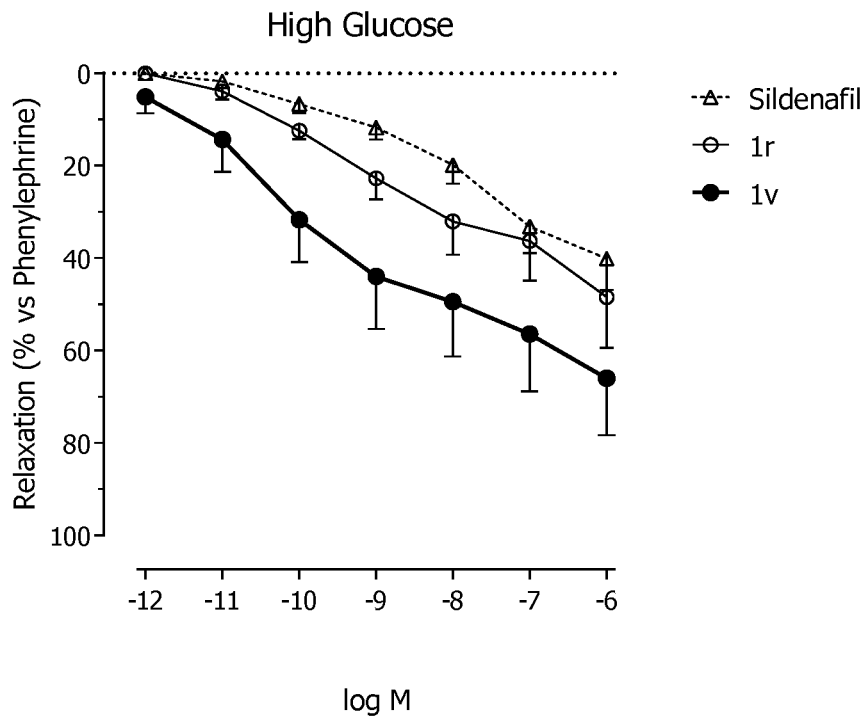
Figure 2C:
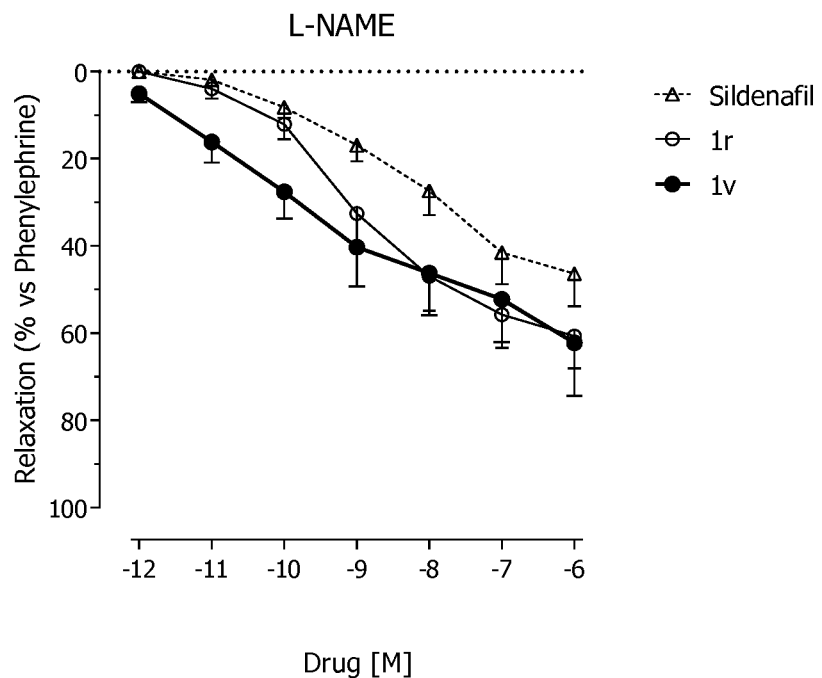
Figure 2D:
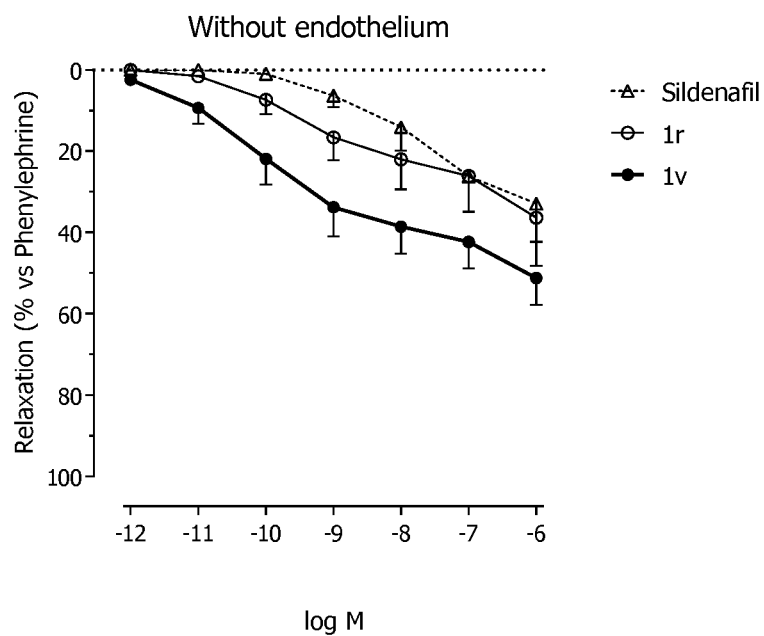
Figure 3A:
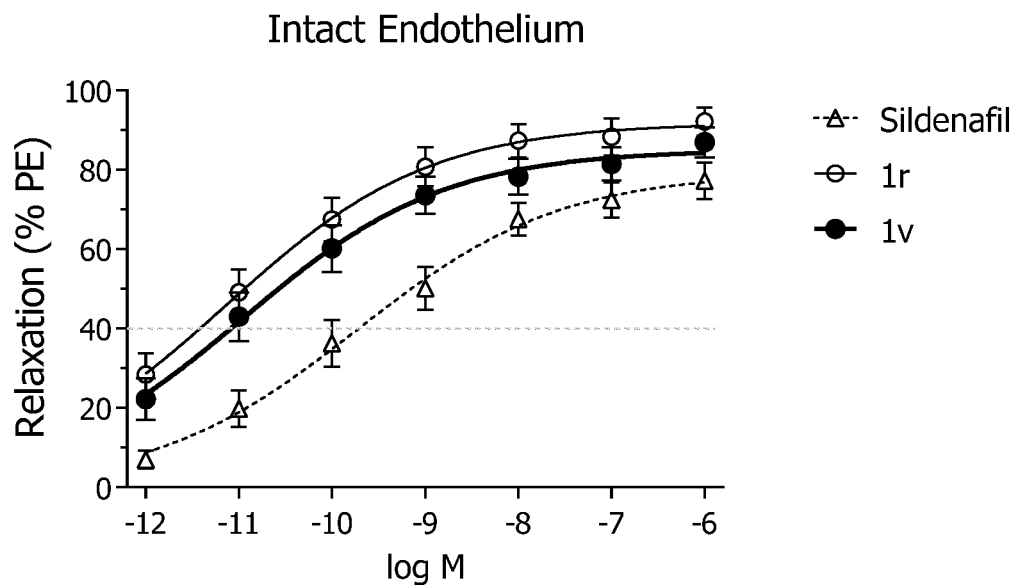
FIGS. 3A-3D: Non-linear regression (Graph Pad Prism 7.01) of the concentration dependent relaxation by 1v, 1r, sildenafil of phenylephrine-precontracted rat aortic rings with intact endothelium (FIG. 3A), exposed to 25 mM glucose for 1 h (FIG. 3B), in presence of L-NAME (100 μM) (FIG. 3C), following mechanical removal of intact endothelium (FIG. 3D) depicted in FIG. 2. Results are shown as the means f SEM from 16-20 preparations. The stippled line indicates the 40% inhibition level.
Figure 3B:
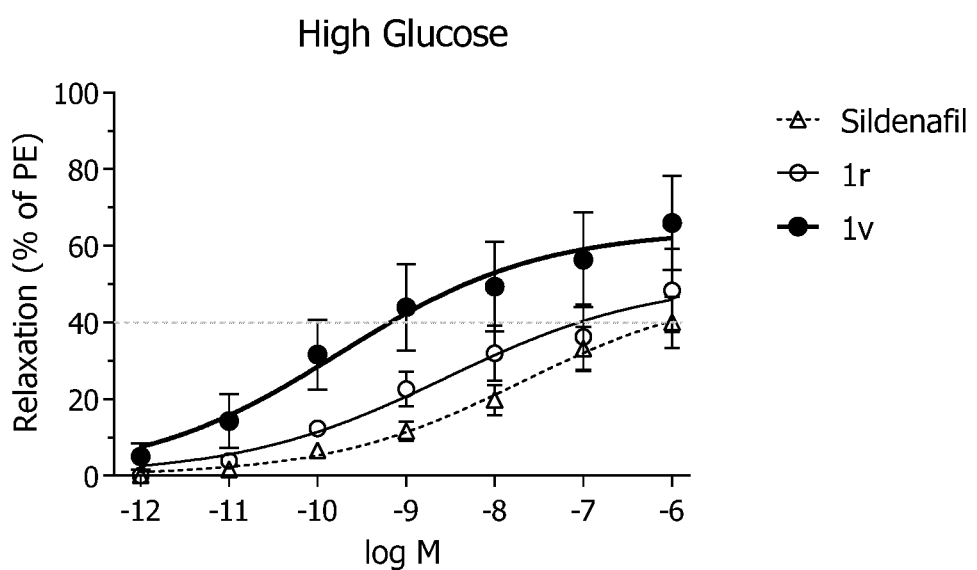
Figure 3C:
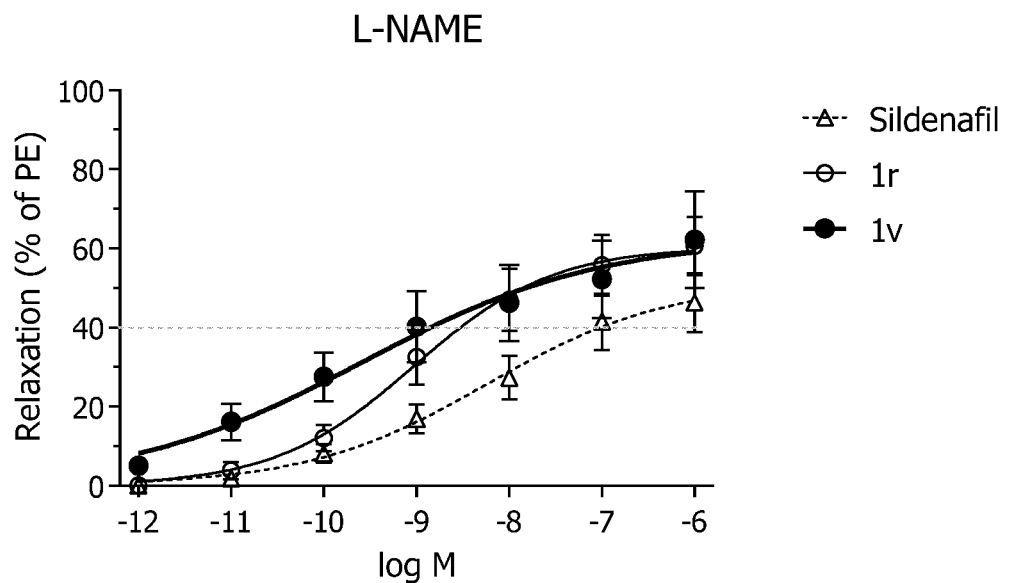
Figure 3D:
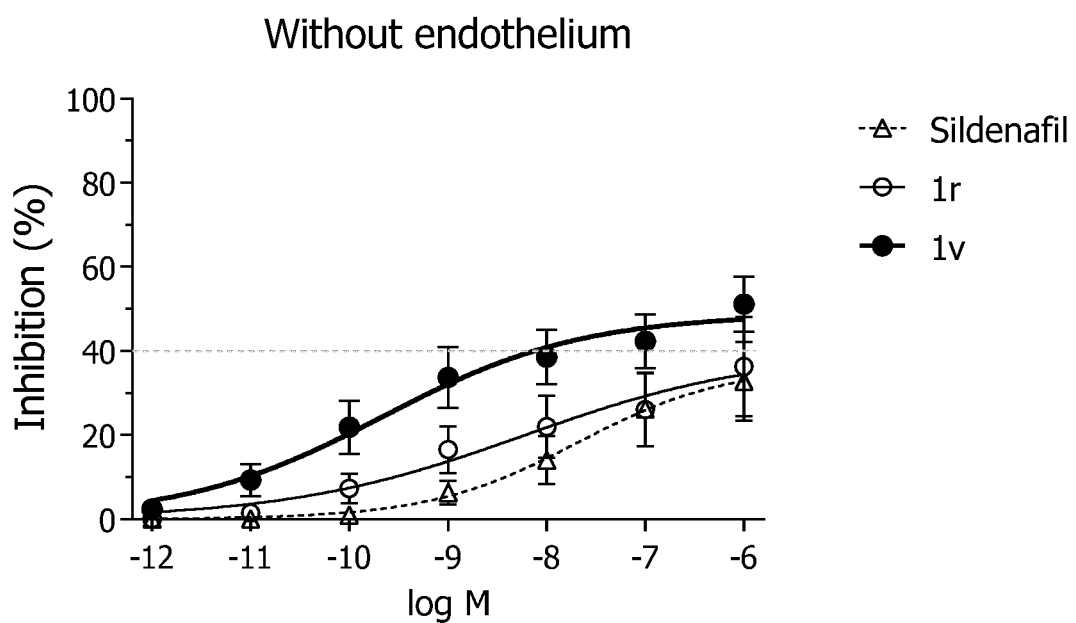

FIG. 2 shows the concentration-dependent relaxation of phenylephrine (PE, 300 nM) precontracted rat aortic rings with intact endothelium (FIG. 2A), when rat aortic rings were pre-exposed to high (25 mM) glucose (FIG. 2B), in presence of the nitric oxide synthase inhibitor L-NAME (FIG. 2C) and in the absence of endothelium (FIG. 2D).

With intact endothelium (FIG. 2A) the inventive compounds 1v and 1r are more potent and effective than Sildenafil. It is noteworthy that 1v was almost as potent and effective as 1r even though the potency to inhibit PDE5 of 1v was 40-fold higher than for 1r as shown in Table 1. These findings may indicate that in the course of the exposure period, 1v was in part converted into 1r secondary of its NO release.

Pre-exposure of rat aortic rings to high glucose (25 mM) is described to imitate a condition of hyperglycemia-induced endothelial dysfunction due to a loss in endothelial nitric oxide generation (Dhar I, Dhar A, Wu L, Desai K (2012). Arginine attenuates methylglyoxal- and high glucose-induced endothelial dysfunction and oxidative stress by an endothelial nitric-oxide synthase-independent mechanism. *J Pharmacol Exp Ther* 342: 196-204). FIG. 2B shows that under these conditions 1v was clearly more potent and efficacious than 1r. In case of the latter, the lower potency and efficacy is most likely secondary to a loss of nitric oxide from endothelial cells resulting in less activation of the cGMP producing soluble guanylate cyclase. In contrast, the superiority of 1v which comprises an additional $ONO_2$ group as compared to 1r is believed to be attributed to the NO release accompanying the PDE5 inhibition. These dual-pharmacology NO-releasing PDE5 inhibitors such as 1v are believed to be highly beneficial for the treatment of diabetic patients. Without being bound by this theory and notion, it is believed that once in the aortic smooth muscle cell, 1v is 'bio-activated' by enzymatic/non-enzymatic processes into the more potent PDE5 inhibitor 1r and nitric oxide. This nitric oxide restores the compromised activity of the soluble guanylate cyclase and interacts with the PDE5 inhibitor in a more than additive fashion. This notion is confirmed under conditions when endothelial nitric oxide generation is blocked by the NOS inhibitor L-NAME (FIG. 2C) or following mechanical removal of the endothelium (FIG. 2D). Compared to intact endothelium the potency and efficacy of the pure PDE5 inhibitors 1r is largely impaired while the NO-releasing PDE5 inhibitor 1v is superior. FIG. 3 shows the non-linear regression analyses of the data presented in FIG. 2.

Potency (EC50), Efficacy (Emax) and concentrations where 40% relaxation was achieved are summarized in Table 2.

TABLE 2

EC50, IC40 and Emax for relaxation of rat aortic rings by 1v, 1r and sildenafil

| Condition Cpd | Intact Endothelium (E+) | | | High Glucose | | |
|---|---|---|---|---|---|---|
| | EC50 pM | IC40 pM | Emax % | EC50 pM | IC40 pM | Emax % |
| sildenafil | 186 | 194 | 79.3 | 20360 | 826989 | 49.1 |
| 1r | 7.4 | 3.8 | 91.9 | 2795 | 89295 | 51 |
| 1v | 11.1 | 8.2 | 85.1 | 181 | 660 | 64.2 |

| Condition Cpd | L-NAME | | | Without Endothelium | | |
|---|---|---|---|---|---|---|
| | EC50 pM | IC40 pM | Emax % | EC50 pM | IC40 pM | Emax % |
| sildenafil | 5804 | 95659 | 51.4 | 20580 | >1000000 | 36.4 |
| 1r | 935 | 2982 | 60.4 | 5942 | >1000000 | 39.8 |
| 1v | 267 | 1412 | 62 | 218 | 7527 | 48.7 |

Based on EC50 and Emax, 1v as compared to sildenafil (i) exerted an about 17-fold more potent relaxation of PE-precontracted rat aortic rings in experiments with intact endothelium, (ii) revealed about 95-fold more potent and more efficacious in relaxation of PE precontracted rat aortic rings in the absence of endothelium, (iii) was about 22-fold more potent and more efficacious in relaxation of PE precontracted rat aortic rings in the presence of L-NAME, (iv) most importantly, revealed about 110-fold more potent and more efficacious to exert relaxation of PE precontracted rat aortic rings with intact endothelium but pre-exposed to high (25 mM) glucose for 60 min prior the experiment was commenced. Thus, related to the reference PDE5 inhibitor sildenafil the inventive NO releasing PDE5 inhibitor 1v achieved 40% relaxation in PE precontracted rat aortic rings (i) with intact endothelium, (ii) without endothelium, (iii) with L-NAME, (iv) with high glucose at about 24-fold, >130-fold, 68-fold, 1250-fold lower concentrations, respectively.

Collectively, these data strongly support the novel and inventive preferred dual pharmacology approach of the present invention as exemplified and designed for 1v, or the corresponding nitrate-ester containing PDE5 inhibitors of the present invention, to activate soluble guanylate cyclase and inhibit PDE5. Such a preferred dual pharmacology approach outperforms PDE5 inhibitors alone, in particular, in conditions of endothelial dysfunction and when endogenous NO generation from endothelial cells is impaired.

The invention claimed is:
1. A compound of the structure:

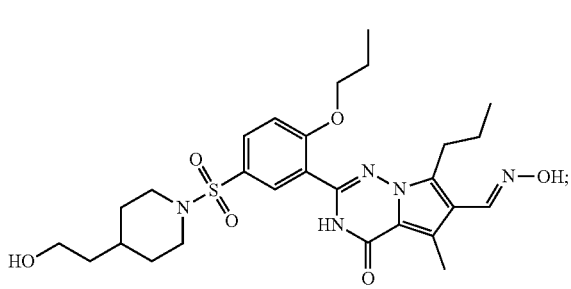

or a pharmaceutically acceptable salt or hydrate thereof.

2. A pharmaceutical composition comprising the compound of claim 1, or a pharmaceutically acceptable salt or hydrate thereof, and a pharmaceutically acceptable excipient, adjuvant, or carrier.

3. A compound of the structure:

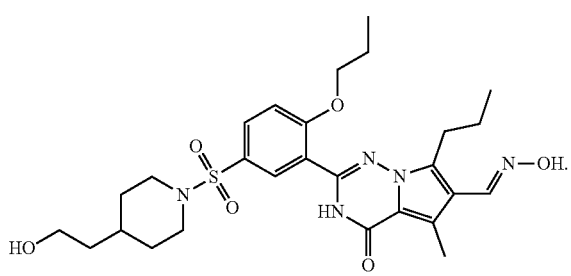 [SMILES: CCCOc1ccc(S(=O)(=O)N2CCC(CCO)CC2)cc1-c1nn2c(CCC)c(/C=N/O)c(C)c2c(=O)[nH]1]

4. A pharmaceutical composition comprising the compound of claim 3, and a pharmaceutically acceptable excipient, adjuvant, or carrier.

5. A compound of the structure:

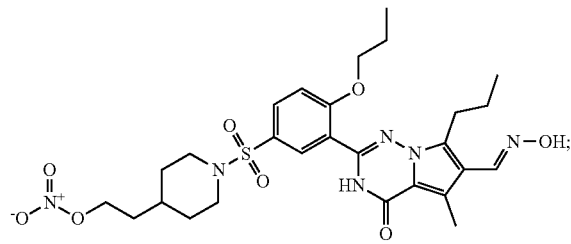

or a pharmaceutically acceptable salt or hydrate thereof.

6. A pharmaceutical composition comprising the compound of claim 5, or a pharmaceutically acceptable salt or hydrate thereof, and a pharmaceutically acceptable excipient, adjuvant, or carrier.

7. A compound of the structure:

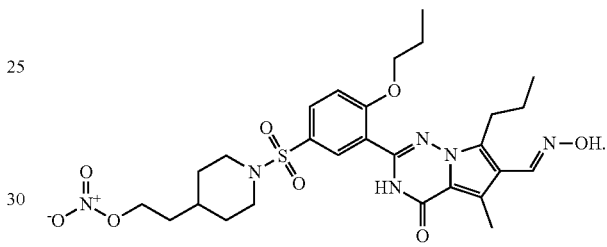

8. A pharmaceutical composition comprising the compound of claim 7, and a pharmaceutically acceptable excipient, adjuvant, or carrier.

* * * * *